(12) United States Patent
Edmondson et al.

(10) Patent No.: US 8,604,038 B2
(45) Date of Patent: Dec. 10, 2013

(54) PYRROLIDINE DERIVED BETA 3 ADRENERGIC RECEPTOR AGONISTS

(75) Inventors: Scott D. Edmondson, Clark, NJ (US); Lehua Chang, Ramsey, NJ (US); Nam Fung Kar, Brooklyn, NY (US); Gergori J. Morriello, Randolph, NJ (US); Christopher R. Moyes, Westfield, NJ (US); Dong-Ming Shen, Edison, NJ (US); Cheng Zhu, Edison, NJ (US); Neville J. Anthony, Northborough, MA (US); Philip Jones, Houston, TX (US); Graham F. Smith, Sudbury, MA (US); Mark E. Scott, Andover, MA (US); Christopher F. Thompson, Arlington, MA (US); Joon Jung, Newton, MA (US); Carolyn Cammarano, Worcester, MA (US); Dawn Marie Hoffman, Boston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 22 days.

(21) Appl. No.: 13/392,282

(22) PCT Filed: Aug. 24, 2010

(86) PCT No.: PCT/US2010/046468
§ 371 (c)(1),
(2), (4) Date: May 14, 2012

(87) PCT Pub. No.: WO2011/025774
PCT Pub. Date: Mar. 3, 2011

(65) Prior Publication Data
US 2012/0225886 A1    Sep. 6, 2012

Related U.S. Application Data

(60) Provisional application No. 61/237,487, filed on Aug. 27, 2009.

(51) Int. Cl.
*A61K 31/50* (2006.01)
*A61K 31/525* (2006.01)

(52) U.S. Cl.
USPC ...... 514/252.05; 514/383; 514/343; 514/256; 514/255.05; 514/370; 514/378; 514/303; 514/428; 548/267.6; 548/199; 548/247; 548/570; 546/276.4; 546/118; 544/335; 544/336; 544/238

(58) Field of Classification Search
USPC ............... 514/252.05, 383, 343, 256, 255.05, 514/370, 378, 303, 428; 548/267.6, 199, 548/247, 570; 546/276.4, 118; 544/335, 544/336, 238
See application file for complete search history.

(56) References Cited

U.S. PATENT DOCUMENTS

| | | | |
|---|---|---|---|
| 6,153,624 A | 11/2000 | Alanine et al. | |
| 6,291,491 B1 | 9/2001 | Weber et al. | |
| 8,354,403 B2 * | 1/2013 | Edmondson et al. | 514/230.5 |
| 8,399,480 B2 * | 3/2013 | Berger et al. | 514/306 |
| 2003/0212063 A1 | 11/2003 | Lafontaine et al. | |

OTHER PUBLICATIONS

Prathipati et al., "Characterization of B3-Adrenergic Receptor", Journal of Computer-Aided Molecular Design, vol. 19, p. 93-110 (2005).

* cited by examiner

*Primary Examiner* — James O Wilson
*Assistant Examiner* — Alexander R Pagano
(74) *Attorney, Agent, or Firm* — Patricia A. Shatynski; Valerie J. Camara

(57) ABSTRACT

The present invention provides compounds of Formula (I), pharmaceutical compositions thereof, and method of using the same in the treatment or prevention of diseases mediated by the activation of β3-adrenoceptor.

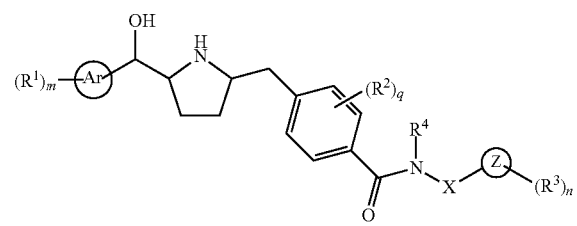

14 Claims, No Drawings

PYRROLIDINE DERIVED BETA 3 ADRENERGIC RECEPTOR AGONISTS

CROSS REFERENCE TO RELATED APPLICATIONS

This application is a U.S. National Phase application under 35 U.S.C. §371 of PCT Application No. PCT/US2010/046468, filed Aug. 24, 2010, which claims priority under 35 U.S.C. §119(e) from U.S. Provisional Application Ser. No. 61/237,487, filed Aug. 27, 2009.

BACKGROUND OF THE INVENTION

The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

β Adrenergic receptors (βAR) are present in detrusor smooth muscle of various species, including human, rat, guinea pig, rabbit, ferret, dog, cat, pig and non-human primate. However, pharmacological studies indicate there are marked species differences in the receptor subtypes mediating relaxation of the isolated detrusor; β1AR predominate in cats and guinea pig, β2AR predominate in rabbit, and β3AR contribute or predominate in dog, rat, ferret, pig, cynomolgus and human detrusor. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97%, cf 1.5% for β1AR mRNA and 1.4% for β2AR mRNA). Moreover, β3AR mRNA expression was equivalent in control and obstructed human bladders. These data suggest that bladder outlet obstruction does not result in downregulation of β3AR, or in alteration of β3AR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states.

Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume.

Overactive bladder is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological condition, bladder outlet obstruction, and other causes. From a pathophysiologic perspective, the overactive bladder symptom complex, especially when associated with urge incontinence, is suggestive of detrusor overactivity. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy). Therefore, there is need for new, well-tolerated therapies that effectively treat urinary frequency, urgency and incontinence, either as monotherapy or in combination with available therapies. Agents that relax bladder smooth muscle, such as β3AR agonists, are expected to be effective for treating such urinary disorders.

SUMMARY OF THE INVENTION

The present invention relates to novel β3AR agonists of Formula I,

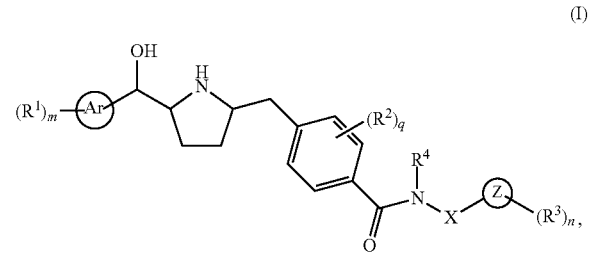

pharmaceutical compositions containing them, as well as methods for the treatment or prophylaxis of disorders mediated through the β3AR using such novel compounds.

DESCRIPTION OF THE INVENTION

Described herein are compounds of structural Formula I:

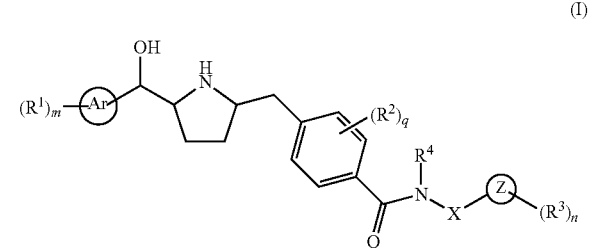

wherein:
m is 0, 1, 2, 3, 4, or 5;
n is 0, 1, 2, 3, 4, or 5;
p is 0, 1, or 2;
q is 0, 1, 2, 3, or 4;
Ar is phenyl or pyridyl;
X is selected from the group consisting of
  (1) a bond, and
  (2) $C_1$-$C_6$ alkanediyl optionally substituted with 1 to 5 groups independently selected from:
    (a) halogen,
    (b) —$OR^a$,
    (c) —$CO_2R^a$,
    (d) —$NR^aR^b$, and
    (e) $C_3$-$C_6$ cycloalkyl;

Z is selected from the group consisting of:
(1) $C_5$-$C_{10}$ carbocyclic ring,
(2) 4 to 6-membered heterocyclic ring with from 1 to 4 heteroatoms selected from oxygen, sulfur and nitrogen,
(3) benzene ring fused to a $C_5$-$C_{10}$ carbocyclic ring,
(4) 5 or 6-membered heterocyclic ring with from 1 to 4 heteroatoms selected from oxygen, sulfur and nitrogen fused to a $C_5$-$C_{10}$ carbocyclic ring, and
(5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;

each occurrence of $R^1$ is independently selected from the group consisting of
(1) $C_1$-$C_6$ alkyl optionally substituted with 1 to 5 halogen atoms,
(2) $C_3$-$C_6$ cycloalkyl,
(3) oxo,
(4) halogen,
(5) nitro,
(6) cyano,
(7) —C(O)$R^a$,
(8) —CO$_2R^a$,
(9) —C(O)N$R^aR^b$,
(10) —O$R^a$,
(11) —N$R^aR^b$, and
(12) Z optionally substituted with 1 to 5 halogen atoms;

each occurrence of $R^2$ is independently selected from the group consisting of:
(1) halogen,
(2) —O$R^a$, and
(3) $C_1$-$C_6$ alkyl optionally substituted with 1 to 5 halogen atoms;

each occurrence of $R^3$ is independently selected from the group consisting of:
(1) $C_1$-$C_6$ alkyl optionally substituted with 1 to 5 groups independently selected from halogen and —O$R^a$,
(2) $C_3$-$C_6$ cycloalkyl, optionally substituted with 1 to 5 halogen atoms,
(3) oxo,
(4) halogen,
(5) cyano,
(6) —O$R^a$,
(7) —C(O)$R^a$,
(8) —CO$_2R^a$,
(9) —C(O)N$R^aR^b$,
(10) —N$R^aR^b$,
(11) —C(O)N$R^aR^b$, and
(12) Z optionally substituted with 1 to 5 groups independently selected from
(a) C1-C6 alkyl optionally substituted with 1 to 5 groups independently selected from halogen, —O$R^a$, oxo, cyano, CO$_2R^a$, and $C_3$-$C_6$ cycloalkyl,
(b) $C_3$-$C_6$ cycloalkyl,
(c) halogen,
(d) oxo,
(e) —O$R^a$,
(f) —N$R^aR^b$,
(g) —C(O)N$R^aR^b$, and
(h) phenyl;

$R^4$ is selected from the group consisting of:
(1) hydrogen, and
(2) $C_1$-$C_6$ alkyl optionally substituted with 1 to 5 groups independently selected from:
(a) halogen,
(b) —O$R^a$,
(c) cyano,
(d) $C_3$-$C_6$ cycloalkyl,
(e) Z optionally substituted with 1 to 5 groups independently selected from halogen, $C_1$-$C_6$ alkyl optionally substituted with 1 to 5 halogen atoms, —O$R^a$, oxo, cyano, CO$_2R^a$, and $C_3$-$C_6$ cycloalkyl,
(g) —S(O)$_p$—N$R^aR^b$, and
(h) —N($R^a$)SO$_2R^b$;

each occurrence of $R^a$ is independently selected from the group consisting of:
(1) hydrogen,
(2) $C_1$-$C_6$ alkyl optionally substituted with 1 to 5 groups independently selected from:
(a) halogen,
(b) —O$R^b$, and
(c) —CO$_2R^b$,
(3) $C_3$-$C_6$ cycloalkyl,
(4) Z optionally substituted with 1 to 5 halogen atoms; and each occurrence of $R^b$ is independently selected from the group consisting of:
(1) hydrogen, and
(2) $C_1$-$C_6$ alkyl optionally substituted with 1 to 5 halogen atoms.

As used herein, the term "alkyl" means both branched- and straight-chain saturated aliphatic hydrocarbon groups having the specified number of carbon atoms. For example, $C_1$-$C_6$ alkyl includes, but is not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tert-butyl (t-Bu), isopentyl, sec-pentyl, tert-pentyl, isohexyl and the like.

The term "cycloalkyl" means a monocyclic saturated carbocyclic ring, having the specified number of carbon atoms, e.g., 3, 4, 5 or 6 carbon atoms. Non-limiting examples of $C_3$-$C_6$ cycloalkyl include cyclopropyl, cyclobutyl, cyclopentyl and cyclohexyl.

The term "alkanediyl" means a straight or branched divalent hydrocarbon radical having the specified number of carbon atoms. Non-limiting examples of $C_1$-$C_4$ "alkanediyl" include, but are not limited to, methylene (—CH$_2$—), ethylene (—CH$_2$CH$_2$—), 1,1-ethanediyl (—CH(CH$_3$)—), 1,2-propanediyl (—CH(CH$_3$)CH$_2$—), 2-methyl-1,1-propanediyl (—CH[C(CH$_3$)$_2$]—), 1,4-butanediyl (—CH$_2$CH$_2$CH$_2$CH$_2$—), 2,3-butanediyl (—CH(CH$_3$)CH(CH$_3$)—), and the like. Example of a halogen substituted alkanediyl is —C(CH$_3$)(F)—.

The term "optionally substituted" means "unsubstituted or substituted," and therefore, the generic structural Formulas described herein encompass compounds containing the specified optional substituent as well as compounds that do not contain the optional substituent. Each variable is independently defined each time it occurs within the generic structural formula definitions.

The tams "halo" or "halogen" are meant to include fluoro, chloro, bromo and iodo, unless otherwise noted.

The terms "carbocycle" or "carbocyclic" refer to saturated, partially unsaturated and aromatic rings having only ring carbon atoms. For examples, $C_1$-$C_4$ carbocyclic ring include, but are not limited to, cyclopentyl, cyclohexyl, cycloheptyl, cyclooctyl, cyclopentenyl, cyclohexenyl, cyclohexadienyl, and phenyl.

The term "aryl" refers to an aromatic carbocycle.

The terms "heterocycle" or "heterocyclic" refer to saturated, partially unsaturated and aromatic rings having at least one ring heteroatom and at least one ring carbon atom; the heterocycle may be attached to the rest of the molecule via a ring carbon atom or a ring hetero atom, for example, a ring nitrogen atom. The terms "heteroaryl" or "heteroaromatic" refer to an aromatic heterocycle. For example, within the definition for Z, the term "a 5- or 6-membered heterocyclic ring with from 1 to 4 heteroatoms selected from oxygen, sulfur and nitrogen" includes, but is not limited to, pyrrolyl, thienyl, (uranyl, imidazolyl, pyrazolyl, oxazolyl, isoxazolyl, thiazolyl, isothiazolyl, triazolyl, tetrazolyl, oxadiazolyl, thiadiazolyl, pyrrolidinyl, tetrahydrofuranyl, pyridinyl, dihydropyridinyl, tetrahydropyridinyl, pyrimidinyl, dihydropyrimidinyl, tetrahydropyrimidinyl, pyrazinyl, dihydropyrazinyl, tetrahydropyrazinyl, pyridazinyl, dihydropyridazinyl, tetrahydropyridazinyl, piperidinyl, piperazinyl, morpholinyl, pyranyl, dihydropyranyl, tetrahydropyranyl, and the like.

Within the definition for Z, the term "a benzene ring fused to a $C_5$-$C_{10}$ carbocyclic ring" includes, but is not limited to, naphthyl, dihydronaphthyl, tetrahydronaphthyl, indenyl, indenyl, benzocycloheptene, tetrahydrobenzocyloheptene, and the like. In one embodiment, a benzene ring is fused to a $C_5$-$C_6$ carbocyclic ring. Such fused ring may be attached to the rest of the molecule via a carbon atom on either ring.

Within the definition for Z, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" includes, but is not limited to, naphthyridinyl, dihydronaphthyridinyl, tetrahydronaphthyridinyl, imidazopyridinyl, pteridinyl, purinyl, quinolizinyl, indolizinyl, tetrahydroquinolizinyl, and tetrahydroindolizinyl. In one embodiment, Z is selected from the group consisting of:

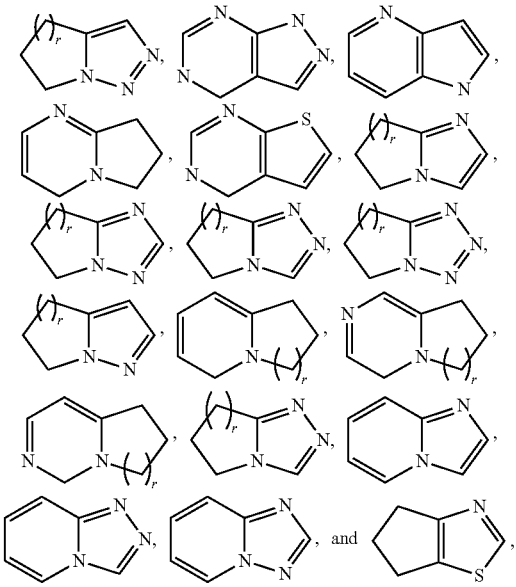

wherein r is 1 or 2. Such fused ring may be attached to the rest of the molecule via a carbon atom or a nitrogen atom on either ring.

To avoid any doubt, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" as used herein includes compounds having only one nitrogen as the sole heteroatom when the nitrogen is located at the bridgehead.

Within the definition for Z, the term "a 5- or 6-membered heterocyclic ring with from 1 to 4 heteroatoms selected from oxygen, sulfur and nitrogen fused to a $C_5$-$C_{10}$ carbocyclic ring" includes, but is not limited to, indolyl, isoindolyl, benzofuranyl, benzothienyl, benzimidazolyl, benzotriazolyl, benzoxazolyl, benzisoxazolyl, benzthiazolyl, benzisothiazolyl, quinolinyl, isoquinolinyl, quinoxalinyl, quinazolinyl, cinnolinyl, indazolyl, tetrahydroquinolinyl, tetrahydroindazolyl, dihydroindazolyl, chromenyl, chromenyl benzthiazolyl,

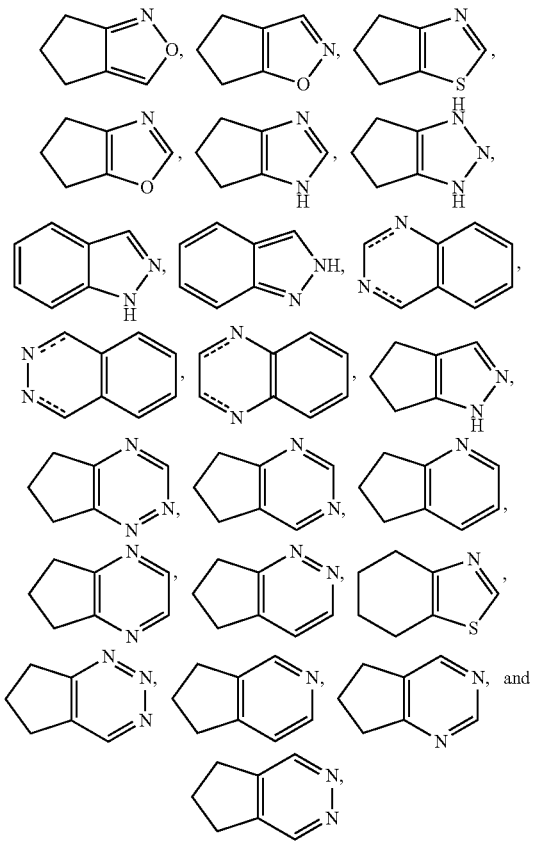

where the dash bond "----" means a single or double bond while conforming to the valency rule for the ring atoms. Such fused ring may be attached to the rest of the molecule via a carbon atom on either ring or a nitrogen atom on the heterocyclic ring.

For the terms $(R^1)_m$, $(R^2)_q$, $(R^3)_n$, as well as other similar notations, when m or q or n is 0, then $R^1$, $R^2$ or $R^3$ is hydrogen; when m, q or n is greater than 1, then each occurrence of $R^1$, $R^2$ or $R^3$ is independently selected from other occurrences of $R^1$, $R^2$ or $R^3$, respectively. For example, when n is 2, the two $R^3$ substituents can be the same or different.

In one embodiment of compounds of Formula I, m is 0, 1, 2, 3 or 4. In another embodiment, m is 0, 1, or 2. In yet another embodiment, m is 0.

In one embodiment, q is 0, 1, or 2. In another embodiment, q is 0.

In one embodiment, each occurrence of $R^1$ is independently selected from the group consisting of:
(1) $C_1$-$C_6$ alkyl optionally substituted with 1 to 5 halogen atoms,
(2) $C_3$-$C_6$ cycloalkyl,
(3) halogen,
(4) —$OR^a$,
(5) —$C(O)R^a$,
(6) —$NR^aR^b$, and
(7) phenyl optionally substituted with 1 to 5 halogen atoms.

In another embodiment, each occurrence of $R^1$ is independently selected from the group consisting of:
(1) $C_1$-$C_4$ alkyl optionally substituted with 1 to 3 halogen atoms,
(2) $C_3$-$C_6$ cycloalkyl,
(3) —$OR^a$,
(4) —$NR^aR^b$, and
(5) halogen.

In yet another embodiment, each occurrence of $R^1$ is independently a $C_1$-$C_4$ alkyl.

In one embodiment, each occurrence of $R^2$ is independently selected from the group consisting of:
(1) halogen,
(2) —$OR^a$, and
(3) $C_1$-$C_6$ alkyl optionally substituted with 1 to 5 halogen atoms.

In another embodiment, each occurrence of $R^2$ is independently a $C_1$-$C_4$ alkyl.

In one embodiment, each occurrence of $R^3$ is independently selected from the group consisting of:
(1) $C_1$-$C_6$ alkyl optionally substituted with 1 to 5 halogen atoms,
(2) $C_3$-$C_6$ cycloalkyl, optionally substituted with 1 to 5 halogen atoms,
(3) oxo,
(4) halogen,
(5) —$OR^a$,
(7) —$C(O)R^a$,
(8) —$CO_2R^a$,
(9) —$NR^aR^b$,
(11) —$C(O)NR^aR^b$, and
(12) Z optionally substituted with 1 to 5 groups independently selected from $C_1$-$C_6$ alkyl and halogen.

In another embodiment, each occurrence of $R^3$ is independently selected from the group consisting of:
(1) $C_1$-$C_4$ alkyl optionally substituted with 1 to 3 halogen atoms,
(2) $C_3$-$C_6$ cycloalkyl, optionally substituted with 1 to 3 halogen atoms,
(3) oxo,
(4) halogen,
(5) —$OR^a$,
(6) —$CO_2R^a$,
(7) —$NR^aR^b$, and
(8) phenyl optionally substituted with 1 to 3 groups independently selected from $C_1$-$C_4$ alkyl and halogen.

In one embodiment, each occurrence of $R^a$ is independently selected from the group consisting of:
(1) hydrogen,
(2) $C_1$-$C_6$ alkyl optionally substituted with 1 to 5 halogen atoms, and
(3) $C_3$-$C_6$ cycloalkyl.

In another embodiment, each occurrence of $R^a$ is independently hydrogen or $C_1$-$C_4$ alkyl. In another embodiment, each occurrence of $R^a$ is independently hydrogen or methyl.

In one embodiment, $R^4$ is hydrogen or $C_1$-$C_4$ alkyl. In another embodiment, $R^4$ is hydrogen or methyl. In yet another embodiment, $R^4$ is hydrogen.

In one embodiment, m is 0, q is 0, and $R^4$ is hydrogen.

In one embodiment, X is a bond or $C_1$-$C_6$ alkanediyl. In another embodiment, X is $C_1$-$C_4$ alkanediyl. In another embodiment, X is —$CH_2$—, —$CH_2CH_2$—, —$CH(CH_3)$—, or —$CH(CH_3)CH_2$—. In another embodiment, X is —$CH_2$—. In yet another embodiment, X is a bond.

In one embodiment, Z is selected from the group consisting of:
(1) phenyl,
(2) 4 to 6-membered heterocyclic ring with from 1 to 4 heteroatoms selected from oxygen, sulfur and nitrogen,
(3) benzene ring fused to a $C_5$-$C_{10}$ carbocyclic ring,
(4) benzene ring fused to a 5 or 6-membered heterocyclic ring with from 1 to 4 heteroatoms selected from oxygen, sulfur and nitrogen, and
(5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen.

In another embodiment, Z is a 5-membered heterocyclic ring having one nitrogen atom and 0 to 3 additional heteroatoms independently selected from N, O and S, or a 6-membered heterocycle having 1, 2 or 3 nitrogen atoms, or 1 nitrogen atom and one oxygen or sulfur atom.

In another embodiment, Z is a 5- or 6-membered heterocyclic ring with from 1 to 4 heteroatoms selected from oxygen, sulfur and nitrogen fused to a $C_5$-$C_6$ carbocyclic ring, and wherein said heterocyclic ring is a 5-membered heterocycle having one nitrogen ring atom and 0 to 3 additional heteroatoms independently selected from N, O and S, or a 6-membered heterocycle having 1, 2 or 3 ring nitrogen atoms, or 1 ring nitrogen atom and a ring oxygen or sulfur atom.

In another embodiment, Z is a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen, wherein said fused ring has 2 to 5 heteroatoms, at least one of which is nitrogen.

In yet another embodiment, Z is selected from the group consisting of thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,2,5-oxadiazolyl,

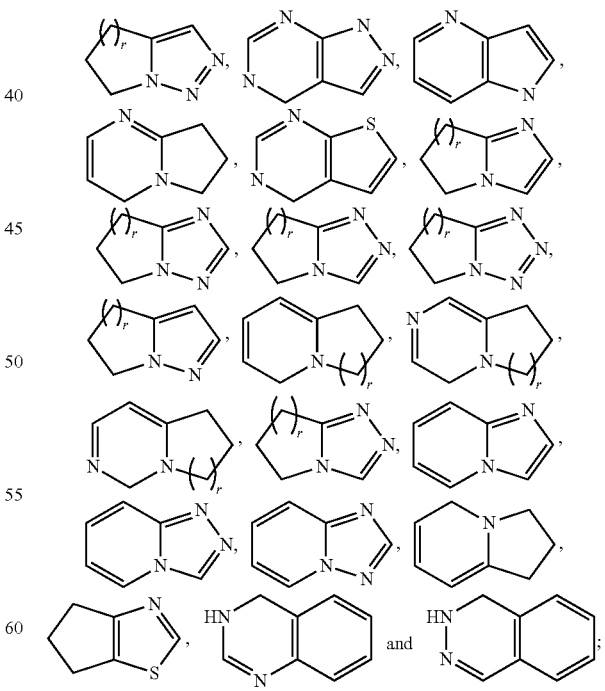

and r is 1 or 2.

In one embodiment, the compounds disclosed herein have Formula Ia, or an N-oxide thereof, or a pharmaceutically acceptable salt thereof, or a stereoisomer thereof, or a pharmaceutically acceptable salt of the stereoisomer thereof:

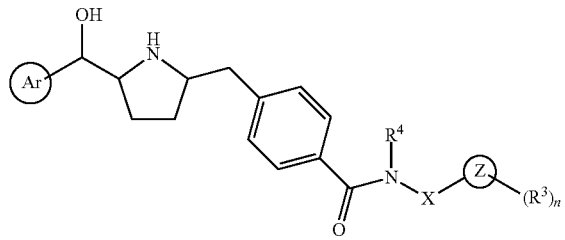

wherein:
n is 0, 1, 2, 3, 4, or 5;
Ar is phenyl or pyridyl;
X is $C_1$-$C_6$ alkanediyl;
Z is selected from the group consisting of:
(1) phenyl,
(2) 4 to 6-membered heterocyclic ring with from 1 to 4 heteroatoms selected from oxygen, sulfur and nitrogen,
(3) benzene ring fused to a $C_5$-$C_{10}$ carbocyclic ring,
(4) 5 or 6-membered heterocyclic ring with from 1 to 4 heteroatoms selected from oxygen, sulfur and nitrogen fused to a $C_5$-$C_{10}$ carbocyclic ring or a benzene ring, and
(5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;
each occurrence of $R^3$ is independently selected from the group consisting of:
(1) $C_1$-$C_6$ alkyl optionally substituted with 1 to 5 groups independently selected from halogen and —$OR^a$,
(2) $C_5$-$C_6$ cycloalkyl, optionally substituted with 1 to 5 halogen atoms,
(3) oxo,
(4) halogen,
(5) —$OR^a$,
(7) —$C(O)R^a$,
(8) —$CO_2R^a$,
(9) —$NR^aR^b$,
(11) —$C(O)NR^aR^b$, and
(12) Z optionally substituted with 1 to 5 groups independently selected from $C_1$-$C_6$ alkyl and halogen;
$R^4$ is hydrogen, methyl or ethyl;
$R^a$ is selected from the group consisting of:
(1) hydrogen,
(2) $C_1$-$C_6$ alkyl optionally substituted with 1 to 5 halogen atoms, and
(3) $C_3$-$C_6$ cycloalkyl; and
$R^b$ is selected from the group consisting of:
(1) hydrogen, and
(2) $C_1$-$C_6$ alkyl optionally substituted with 1 to 5 halogen atoms.

In one embodiment of compounds of Formula Ia, each occurrence of $R^3$ is independently selected from the group consisting of:
(1) $C_1$-$C_4$ alkyl optionally substituted with 1 to 3 halogen atoms,
(2) $C_3$-$C_6$ cycloalkyl, optionally substituted with 1 to 3 halogen atoms,
(3) halogen,
(4) —$OR^a$,
(5) —$CO_2R^a$,
(6) —$NR^aR^b$, and
(7) Z optionally substituted with 1 to 5 groups independently selected from $C_1$-$C_4$ alkyl and halogen.

In one embodiment, compounds described herein have the specified stereo configuration at the indicated chiral center:

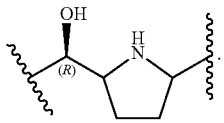

In another embodiment, compounds described herein have the specified stereoconfiguration at the indicated chiral centers, with the chiral center marked with an asterisk being R or S:

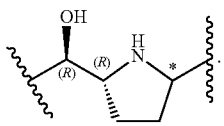

In one subset, the configuration at the chiral center marked with an asterisk is S.

In one embodiment, compounds described herein are as described in the Examples below.

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the fou hulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. The above Formulas I and Ia are shown without a definitive stereochemistry at certain positions. The present invention includes all stereoisomers of Formulas I and Ia and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound described herein may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms).

Both keto and enol forms, individually as well as mixtures thereof, are included within the scope of the present invention.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formulas I and Ia. As used herein, the term "solvate" refers to a complex of variable stoichiometry formed by a solute (i.e., a compound of Formula I or Ia) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrates include, but are not limited to, hemi-, mono, sesqui-, di- and trihydrates.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound described herein or with a compound which may not be a compound described herein, but which converts to a compound described herein in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound described herein. The term "mammal" includes human and non-human animals such as dogs and cats and the like. The diseases, disorders or conditions for which compounds of the present invention are useful in treating or preventing include, but are not limited to, (1) overactive bladder, (2) urinary incontinence, (3) urge urinary incontinence, (4) urinary urgency, (5) diabetes mellitus, (6) hyperglycemia, (7) obesity, (8) hyperlipidemia, (9) hypertriglyceridemia, (10) hypercholesterolemia, (11) atherosclerosis of coronary, cerebrovascular and peripheral arteries, (12) gastrointestinal disorders including peptic ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (13) neurogenic inflammation of airways, including cough, asthma, (14) depression, (15) prostate diseases such as benign prostate hyperplasia, (16) irritable bowel syndrome and other disorders needing decreased gut motility, (17) diabetic retinopathy, (18) preterm labor, and (19) elevated intraocular pressure and glaucoma.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds described herein are administered orally.

The effective dosage of active ingredient employed may vary depending on the particular compound employed, the mode of administration, the condition being treated and the severity of the condition being treated. Such dosage may be ascertained readily by a person skilled in the art.

When treating overactive bladder (OAB) in conjunction with other anti-OAB agents, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg, or more specifically, from about 0.7 mg to about 2000 mg. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg. This dosage regimen may be adjusted to provide the optimal therapeutic response.

When treating diabetes mellitus and/or hyperglycemia, as well as other diseases or disorders for which compounds described herein are useful, generally satisfactory results are obtained when the compounds of the present invention are administered at a daily dosage of from about 0.001 mg to about 100 mg per kg of animal body weight, preferably given in a single dose or in divided doses two to six times a day, or in sustained release form. In the case of a 70 kg adult human, the total daily dose will generally be from about 0.07 mg to about 350 mg. This dosage regimen may be adjusted to provide the optimal therapeutic response.

In one embodiment, a compound of the present invention is used in the manufacture of a medicament for the treatment or prevention of a disease or disorder mediated by the activation of β3-adrenoceptor.

Another aspect of the present invention provides pharmaceutical compositions which comprises a compound described herein and a pharmaceutically acceptable carrier. The pharmaceutical compositions of the present invention comprise a compound described herein as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, intravesical, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds described herein can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds described herein may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds described herein may be used in combination with other drugs that are used in the treatment/prevention/suppression or amelioration of the diseases or conditions for which compounds described herein are useful. Such other drugs may be administered, by a route and in an amount commonly used therefor, contemporaneously or sequentially with a compound described herein. When a compound described herein is used contemporaneously with one or more other drugs, a pharmaceutical unit dosage form containing such other drugs in addition to the compound described herein is preferred. Accordingly, the pharmaceutical compositions of the present invention include those that also contain one or more other active ingredients, in addition to a compound described herein. Examples of other active ingredients that may be combined with a compound described herein, either administered separately or in the same pharmaceutical compositions, include, but are not limited to:

(a) overactive bladder medicines including (i) muscarinic receptor antagonists (e.g. tolterodine, oxybutynin including S-oxybutynin, hyoscyamine, propantheline, propiverine, trospium including trospium chloride, solifenacin, darifenacin, imidafenacin, fesoterodine, temiverine, SVT-40776, 202405 by GlaxoSmithKline, TD6301, RBX9841, DDP200, PLD179, and other anticholinergics. See, for example, U.S. Pat. Nos. 5,382,600; 3,176,019; 3,480,626; 4,564,621; 5,096,890; 6,017,927; 6,174,896; 5,036,098; 5,932,60; 6,713,464; 6,858,650; and DD 106643. See also, U.S. Pat. Nos. 6,103,747; 6,630,162; 6,770,295; 6,911,217; 5,164,190; 5,601,839; 5,834,010; 6,743,441; WO2002000652; WO200400414853. As will be appreciated by those of skill in the art, these drugs may be administered orally or topically in standard or extended release forms, such as extended release tolterodine, extended release oxybutynin and transdermal oxybutynin), (ii) NK-1 or NK-2 antagonists (e.g. aprepitant, cizolirtine, compounds disclosed in WO2005/073191, WO2005/032464, and other reported NK-1 antagonists), (iii) alpha adrenergic receptor antagonists (e.g. alfuzosin, doxazosin, prazosin, tamsulosin, terazosin, and others), (iv) potassium channel openers (e.g. cromakalim, pinacidil, and others), (v) vanilloids and other afferent-nerve modulators—agonists and antagonists (e.g. capsaicin, resiniferatoxin, and others), (vi) dopamine D1 receptor agonists (e.g. pergolinde), (vii) serotonergic and/or norepinephrine reuptake inhibitors (e.g. duloxetine), (viii) neuromuscular junction inhibition of acetylcholine release (e.g. botulinum toxin), (ix) calcium channel blockers (e.g. diltiazem, nifedipine, verapamil, and others), (x) inhibitors of prostaglandin synthesis (e.g. flurbiprofen), (xi) gamma aminobutyric acid receptor antagonists (e.g. baclofen), (xii) vaginal estrogen preparations (xiii) selective norepinephrine reuptake inhibitors, (xiv) 5-HT2C agonists, (xv) voltage gated sodium channel blocker, (xvi) P2X purinergic receptor antagonists (e.g. P2X1 or P2X3 antagonists), (xvii) PAR2 inhibitors, (xviii) phosphodiesterase inhibitors (e.g. PDE1, PDE4, and PDE5 inhibitors); and (xix) ATP sensitive potassium channel openers.

(b) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(c) insulin or insulin mimetics;

(d) sulfonylureas such as tolbutamide and glipizide;

(e) α-glucosidase inhibitors (such as acarbose), (f) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrat, fenofibrate and benzafibrate), (iv) inhibitors of cholesterol absorption for example beta-sitosterol and ezetimibe, and (acyl CoA:cholesterol acyltransferase) inhibitors for example melinamide, (v) probucol, (vi) vitamin E, and (vii) thyromimetics;

(g) PPARδ agonists such as those disclosed in WO97/28149;

(h) antiobesity compounds such as fenfluramine, dexfenfluramine, phentermine, sibutramine, orlistat, and other β3 adrenergic receptor agonists;

(i) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(j) PPARα agonists such as described in WO 97/36579 by Glaxo;

(k) PPARγ antagonists as described in WO97/10813; and (l) serotonin reuptake inhibitors such as fluoxetine and sertraline.

In one embodiment, a compound of the present invention and a second active agent as described above are used in the manufacture of a medicament for the treatment or prevention of a disease or disorder mediated by the activation of β3-adrenoceptor.

The compounds of disclosed herein can be prepared according to the procedures of the following Schemes and Examples using appropriate materials, and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the faun of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

A variety of chromatographic techniques may be employed in the preparation of the compounds. These techniques include, but are not limited to: High Performance Liquid Chromatography (HPLC) including normal phase, reversed phase, and chiral phase HPLC; Medium Pressure Liquid Chromatography (MPLC), Super Critical Fluid Chromatography; preparative Thin Layer Chromatography (prep TLC); flash chromatography with silica gel or reversed-phase silica gel; ion-exchange chromatography; and radial chromatography. All temperatures are degrees Celsius unless otherwise noted.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented, Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Throughout the application, the following terms have the indicated meanings unless noted otherwise:

| Term | Meaning |
| --- | --- |
| Ac | Acyl (CH$_3$C(O)—) |
| Aq. | Aqueous |
| Bn | Benzyl |
| BOC (Boc) | t-Butyloxycarbonyl |

| Term | Meaning |
| --- | --- |
| BOP | Benzotriazol-1-yloxytris(dimethylamino)-phosphonium hexafluorophosphate |
| °C. | Degree Celsius |
| Calc. or calc'd | Calculated |
| Celite | Celite ™ diatomaceous earth |
| DCC | Dicyclohexylcarbodiimide |
| DCM | Dichloromethane |
| DIEA | N,N-diisopropyl-ethylamine |
| DMAP | 4-Dimethylaminopyridine |
| DMF | N,N-dimethylformamide |
| EDC | 1-Ethyl-3-(3-dimethylaminopropyl) carbodiimide |
| Eq. or equiv. | Equivalent(s) |
| ES-MS and ESI-MS | Electron spray ion-mass spectroscopy |
| Et | Ethyl |
| EtOAc | Ethyl acetate |
| g | Gram(s) |
| h or hr | Hour(s) |
| HATU | O-(7-azabenzotriazol-1-yl)-N,N,N',N'-tetramethyluronium hexafluorophosphate |
| HCl | Hydrogen chloride |
| HOAc | Acetic acid |
| HOAT | 1-Hydroxy-7-azabenzotriazole |
| HOBT | 1-Hydroxybenzotriazole |
| HPLC | High performance liquid chromatography |
| IPA | Isopropyl alcohol |
| kg | Kilogram(s) |
| LC/MS or LC-MASS | Liquid chromatography mass spectrum |
| L | Liter(s) |
| LDA | Lithium diisopropylamide |
| LiOH | Lithium hydroxide |
| LiHMDS | Lithium bis(trimethylsilyl)amide |
| M | Molar(s) |
| Me | Methyl |
| MeOH | Methanol |
| MF | Molecular formula |
| min | Minute(s) |
| mg | Milligram(s) |
| mL | Milliliter(s) |
| mmol | Millimole(s) |
| MOZ (Moz) | p-Methoxybenzyloxycarbonyl |
| MP | Melting point |
| MS | Mass spectrum |
| NaH | Sodium hydride |
| nM | Nanomolar |
| OTf | Trifluoromethanesulfonyl |
| 10% Pd/C | Palladium, 10 weight percent on activated carbon |
| Ph | Phenyl |
| Prep. | Preparative |
| Ref. | Reference |
| r.t. or rt or RT | RT |
| Sat. | Saturated |
| SCF $CO_2S$ | Super critical fluid carbon dioxide |
| TBAF | Tetrabutylammonium fluoride |
| TBAI | Tetrabutylammonium iodide |
| TBDPS | Tert-butyl diphenylsilyl |
| TBS, TBDMS | Tert-butyl dimethylsilyl |
| TEA or $Et_3N$ | Triethylamine |
| Tf | Triflate or trifluoromethanesulfonate |
| TFA | Trifluoroacetic acid |
| THF | Tetrahydrofuran |
| TLC | Thin-layer chromatography |
| TMS | Trimethylsilyl |
| TMSOK | Potassium trimethylsilanolate |

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Reaction Schemes below illustrate the methods employed in the synthesis of the compounds described herein. All substituents are as defined above unless indicated otherwise. The synthesis of the novel compounds described herein may be accomplished by one or more of several similar routes. The Examples further illustrate details for the preparation of the compounds described herein. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless noted otherwise. Mass spectra (MS) were measured by electron-spray ion-mass spectroscopy.

In Scheme I, amino diol (I-1) is treated with acetone in toluene and the reaction mixture is refluxed under a Dean-Stark trap to remove water. After removal of the solvent, the unpurified acetonide compound is treated with di-tert-butyl dicarbonate ($Boc_2O$) at ambient temperature to afford Boc protected compound I-2. Conversion of alcohol I-2 to aldehyde I-3 can be achieved by oxidation such as a Swern oxidation (Jayaraman, M.; Deshmukh, A. R.; Bhawal. B. M. Tetrahedron, 1996, 52, 8989-9004). Treatment of I-3 with (triphenylphosphoranylidene)acetaldehyde for a period of 24-40 h in an inert organic solvent, such as dichloromethane, affords unsaturated aldehyde I-4. The carbon-carbon double bond in I-4 is then reduced via catalytic hydrogenation with 10% palladium on carbon under hydrogen atmosphere in a solvent such as acetone to afford the saturated aldehyde I-5. Treatment of aldehyde I-5 with a Wittig reagent derived from a phosphonium salt such as (4-methoxycarbonylbenzyl)triphenylphosphoniurn chloride in the presence of a base such as N,N-diisopropylethylamine or sodium tert-butoxide affords I-6. The product is a mixture of cis and trans alkene. The reaction is usually performed in an inert organic solvent such as tetrahydrofuran or dimethyl sulfoxide and under an inert atmosphere such as nitrogen.

After both the acetonide and Boc groups are removed under acid conditions such as via treatment with a hydrochloride methanol solution, amino alcohol I-7 is converted to I-8 via treatment with tert-butyldimethylsilyl chloride (TBSCl) and benzyl chloroformate (CbzCl) in the presence of an anhydrous organic base, such as N,N-diisopropylethylamine. Oxidation of the olefin with 3-chloroperbenzoic acid (mCPBA) at ambient temperature affords expoide I-9 which contains a mixture of diastereomers.

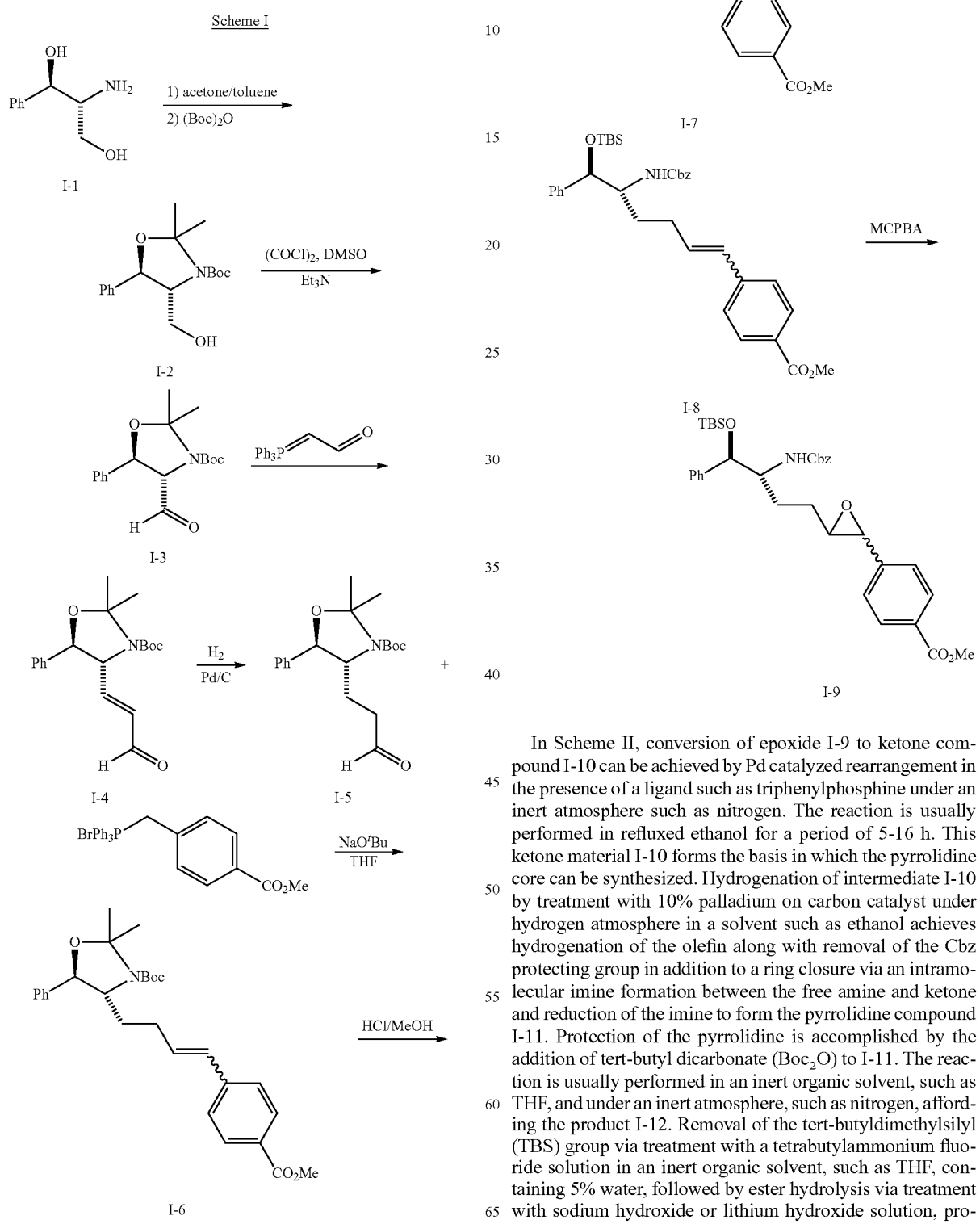

In Scheme II, conversion of epoxide I-9 to ketone compound I-10 can be achieved by Pd catalyzed rearrangement in the presence of a ligand such as triphenylphosphine under an inert atmosphere such as nitrogen. The reaction is usually performed in refluxed ethanol for a period of 5-16 h. This ketone material I-10 forms the basis in which the pyrrolidine core can be synthesized. Hydrogenation of intermediate I-10 by treatment with 10% palladium on carbon catalyst under hydrogen atmosphere in a solvent such as ethanol achieves hydrogenation of the olefin along with removal of the Cbz protecting group in addition to a ring closure via an intramolecular imine formation between the free amine and ketone and reduction of the imine to form the pyrrolidine compound I-11. Protection of the pyrrolidine is accomplished by the addition of tert-butyl dicarbonate (Boc$_2$O) to I-11. The reaction is usually performed in an inert organic solvent, such as THF, and under an inert atmosphere, such as nitrogen, affording the product I-12. Removal of the tert-butyldimethylsilyl (TBS) group via treatment with a tetrabutylammonium fluoride solution in an inert organic solvent, such as THF, containing 5% water, followed by ester hydrolysis via treatment with sodium hydroxide or lithium hydroxide solution, produces carboxylic acid compound I-13 which can be used for standard amide coupling.

Scheme II

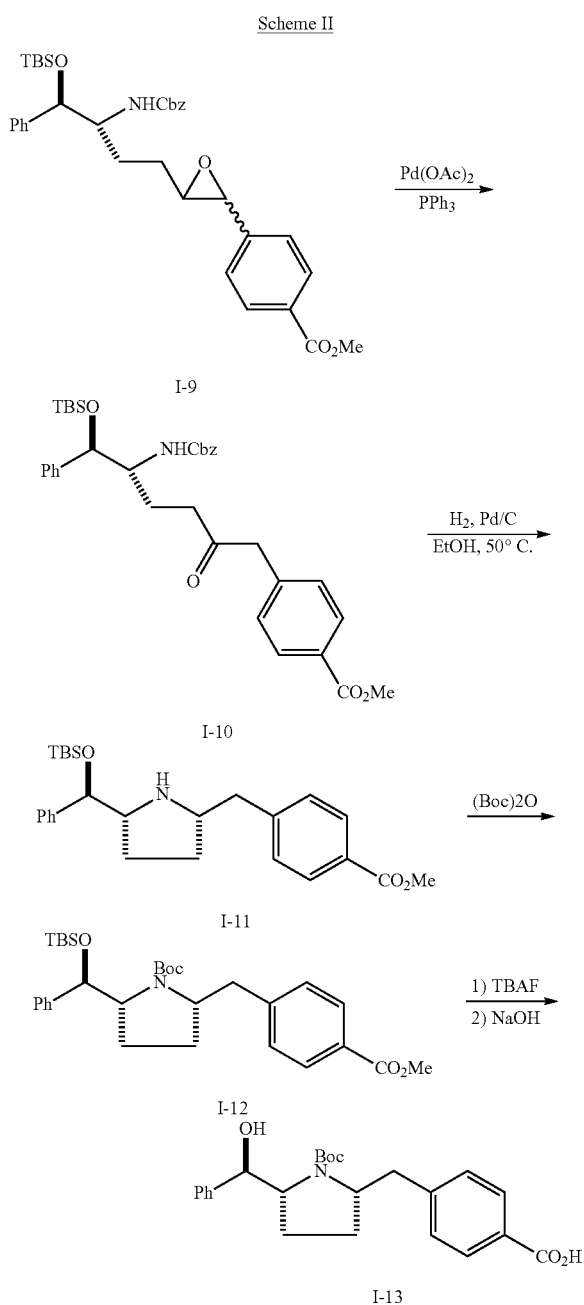

Scheme III outlines the process of synthesizing the acetylene intermediate via aldol chemistry to set the chirality of both the hydroxyl group and left hand portion of the pyrrolidine. From there, this acetylene intermediate can be used to synthesize both the cis and trans pyrrolidines. Commercially available I-14 is first treated with trimethylacetyl chloride in the presence of a weak organic base such as triethylamine at −25° C. for 2 h. The sequential addition of anhydrous lithium chloride and (S)-(−)-4-benzyl-2-oxazolidinone to the mixture followed by gradual warming to RT over a period of time between 12 and 16 h affords imide I-15. The reaction is usually performed in an inert organic solvent, such as THF, under an inert atmosphere, such as nitrogen. The alcohol I-17 is prepared according to published procedures (See Evans et al., *J. Am. Chem. Soc.* 2002, 124, 392-394). For example, treatment of I-15 with anhydrous magnesium chloride, triethylamine, the appropriate aldehyde I-16, such as 6-chloro-pyridine-3-carboxaldehyde, and chlorotrimethylsilane at RT over a period of 72 h yields the trimethylsilyl ether of the aldol product I-17. The reaction is usually performed in an organic solvent such as ethyl acetate under an inert atmosphere such as nitrogen. Treatment of the trimethylsilyl ether intermediate with a trifluoroacetic acid and methanol mixture affords the alcohol I-17.

Conversion of I-17 to I-18 can be achieved by selecting an appropriate silyl protecting agent, such as tert-butyl dimethylsilyl trifluoromethanesulfonate, and reacting it in the presence of a weak organic base, such as 2,6-lutidine, at 0° C. for a period of between 12 to 16 h. The hydrolysis of imide I-18 is achieved by treatment with lithium peroxide at 0° C. for a period of 15-18 h. The peroxy acid is subsequently reduced with an aqueous solution of sodium sulfite to afford the carboxylic acid I-19. The reaction is usually performed in a mixture of an inert organic solvent, such as THF, and water under an inert atmosphere, such as nitrogen.

Finally, I-19 is treated with diphenylphosphoryl azide in the presence of a weak organic base such as triethylamine for a period of 6 h at RT. Addition of the appropriate alcohol, such as 4-methoxybenzyl alcohol, with heating to 100° C. for a period between 12 and 16 h yields the corresponding carbamate I-20. The reaction is usually performed in an inert organic solvent, such as toluene, under an inert atmosphere, such as nitrogen. This material forms the basis in which the pyrrolidine core can be synthesized.

Scheme III

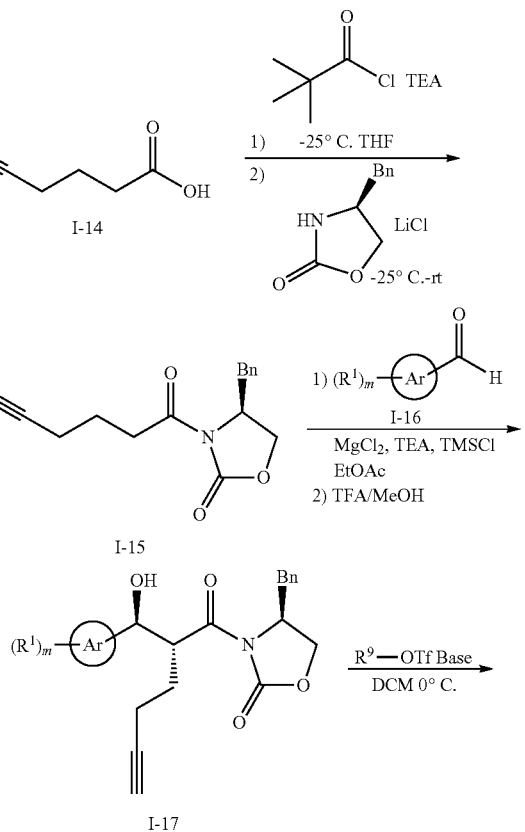

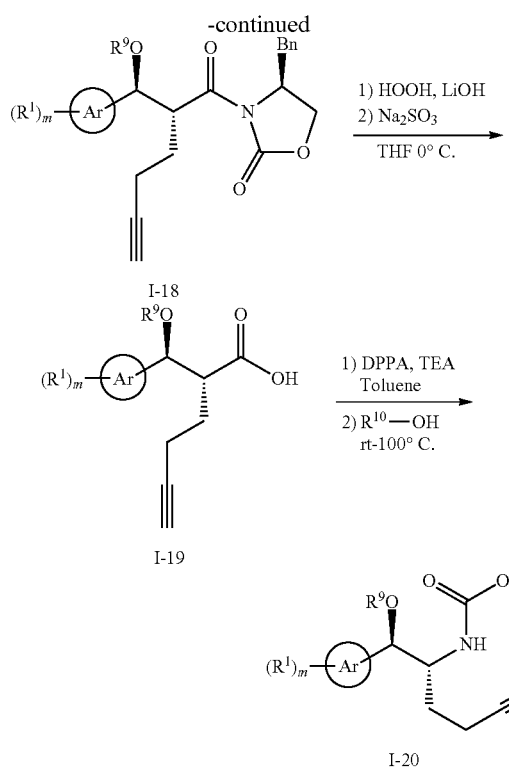

R⁹ is silyl hydroxy protecting group; R¹⁰ is carboxyl protecting group

Scheme IV describes the synthesis of the cis-pyrrolidine (I-25) and trans-pyrrolidine (I-26) intermediates from the appropriately protected amine I-20 described in Scheme III. The alkyne I-20 may be reacted in a Sonagashira type cross-coupling reaction with the corresponding aryl halide I-21 to afford I-22 using the appropriate reaction conditions known to those skilled in the art. The reaction conditions can include the use of catalysts, such as tetrakis(triphenylphosphine)-palladium(0), with copper(I) iodide in the presence of an organic base, such as triethylamine, or palladium(II) acetate with an organic base, such as tetrabutylammonium acetate, in an organic solvent, such as acetonitrile or DMF, under an inert atmosphere, such as nitrogen. The carbamate protecting group of I-22 can be removed using the appropriate reaction conditions known to those skilled in the art to afford the corresponding amine I-23. The reaction conditions can include trifluoroacetic acid in an organic solvent, such as dichloromethane and hydrochloric acid in an organic solvent such as ether. Amine I-23 subsequently undergoes an intramolecular ring closure with the alkyne to afford the imine I-24 under the influence of catalytic amount $PtCl_2$, in an inert organic solvent such as toluene, at a temperature of 70° C. under an inert atmosphere, such as argon. Reduction of the imine I-24 can be achieved by treatment with sodium triacetoxyborohydride $NaBH(OAc)_3$ in an organic solvent, such as dichloromethane, at a temperature of 0° C. under an inert atmosphere, such as nitrogen. This affords mixture of cis- and trans-pyrrolidine which can be used in the next step. Protection of the cis and trans pyrrolidine is accomplished by the addition of tert-butyl dicarbonate ($Boc_2O$) in the presence of a weak organic base, such as triethylamine or N,N-diisopropylethylamine. The reaction is usually performed in an inert organic solvent, such as dichloromethane, and under an inert atmosphere, such as nitrogen. This affords Boc protected cis-pyrrolidine (I-25) and trans-pyrrolidine (I-26) intermediates which can be separated by silica gel chromatography. I-25 is the major diastereomer produced in the reaction and is the first diastereomer to elute off the column.

Scheme IV

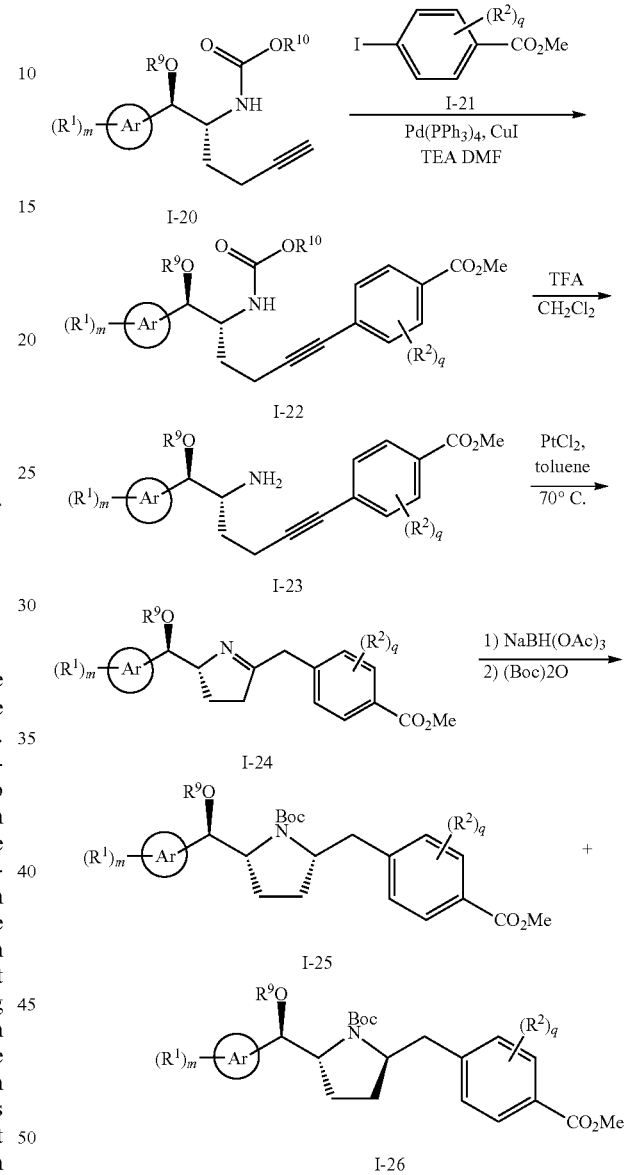

Scheme V describes the synthesis of cis and trans-pyrrolidine carboxylic acid from their corresponding intermediates I-25 and I-26 described in Scheme IV. In some cases) hydrogenation is required in order to remove halogen substituents $R^1$ and $R^2$. The reaction is usually performed by treatment of I-25 or I-26 with 10% palladium on carbon in the presence of potassium acetate under an atmosphere of hydrogen between 15 and 50 psi in a solvent, such as ethanol, over an 8-14 h period of time. Ester hydrolysis via treatment with sodium hydroxide or lithium hydroxide aqueous solution produces carboxylic acid compound I-27. Removal of the silyl protecting group of I-27 via treatment with a tetrabutylammonium fluoride solution in an inert organic solvent, such as THF, containing 5% water affords alcohol acids of general structural formula I-28. The reaction is usually performed in an

Scheme V

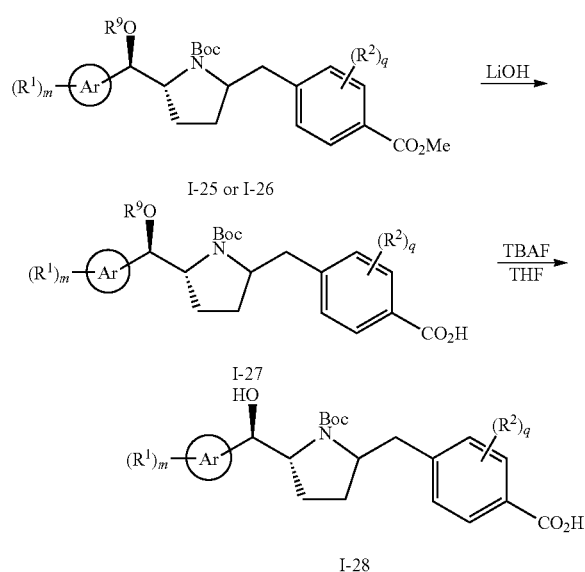

Scheme VI describes an alternative synthesis of pyrrolidine carboxylic acid ester I-25 from the appropriately protected amine I-20 described in Scheme III and appropriate 1-bromo-4 iodobenzene. The alkyne I-20 reacts in a Sonagashira type cross-coupling reaction with the corresponding 1-bromo-4 iodobenzene I-29 to afford I-30 using the appropriate reaction conditions known to those skilled in the art. The carbamate protecting group of I-30 can be removed using the appropriate reaction conditions such as trifluoroacetic acid in dichloromethane. Subsequent intramolecular ring closure affords the imine I-31 under the influence of catalytic amount of $PtCl_2$, in an inert organic solvent such as toluene, at a temperature of 85° C. under an inert atmosphere, such as nitrogen. Reduction of the imine I-31 can be achieved by treatment with sodium triacetoxyborohydride $NaBH(OAc)_3$ in an organic solvent, such as dichloromethane, at a temperature of 0° C. under an inert atmosphere, such as nitrogen. This affords mixture of cis- and trans-pyrrolidine which can be used in the next step. Protection of the cis and trans pyrrolidine is accomplished by the addition of tert-butyl dicarbonate ($Boc_2O$) in the presence of a weak organic base, such as triethylamine or N,N-diisopropylethylamine. The reaction is usually performed in an inert organic solvent, such as dichloromethane, and under an inert atmosphere, such as nitrogen. This affords Boc protected cis-pyrrolidine (I-32) and trans-pyrrolidine intermediates which can be separated by silica gel chromatography. I-32 is the major diastereomer produced in the reaction and is the first diastereomer to elute off the column. Carbonylation of bromide I-32 can be achieved by the use of catalysts, such as $Pd(dppf)Cl_2$, in the presence of an organic base, such as triethylamine in an organic solvent, such as methanol, under carbon monoxide atmosphere.

Scheme VI

Scheme VII describes the synthesis of amides of structural formula I-35 via appropriate amide bond formation conditions known to those skilled in the arts such as EDC, DCC, HATU or BOP in the presence of the appropriate additive such as HOAT or HOBT, and either with or without a suitable organic base, such as N,N-diisopropylethylamine or triethylamine. For example, a desired amine I-33 and pyrrolidine carboxylic acid I-28 can be treated with N-(3-dimethylaminopropyl)-N'-ethylcarbodiimide (EDC) hydrochloride and 1-hydroxybenzotriazole (HOBO in the presence of a suitable organic base, such as N,N-diisopropylethylamine. The reaction is usually performed in an inert organic solvent such as N,N-dimethylformamide, at RT for a period of 2-24 h. Removal of the Boc protecting groups of I-34 via treatment with a solution of TPA in an inert organic solvent, such as dichloromethane, at ambient temperature for a period of time between 1 and 6 h affords the final desired products of various amides shown in the general structural formula I-35. Alternatively, treatment of I-34 with a solution of hydrogen chloride in an organic solvent, such as 1,4-dioxane or ethyl acetate, also yields the desired product of structural formula I-35. Additional de-protection steps may be included if there are useful protecting groups known to those skilled in the art necessary to allow the chemistry to proceed in a facile fashion. These protecting groups may include trityl groups, benzylcarbamate groups, ester groups, say groups or other groups suitable for the protection of heterocyclic compounds or the functional groups such as amines, hydroxyls, carboxylic acids or other groups known to those skilled in the art.

Scheme VII

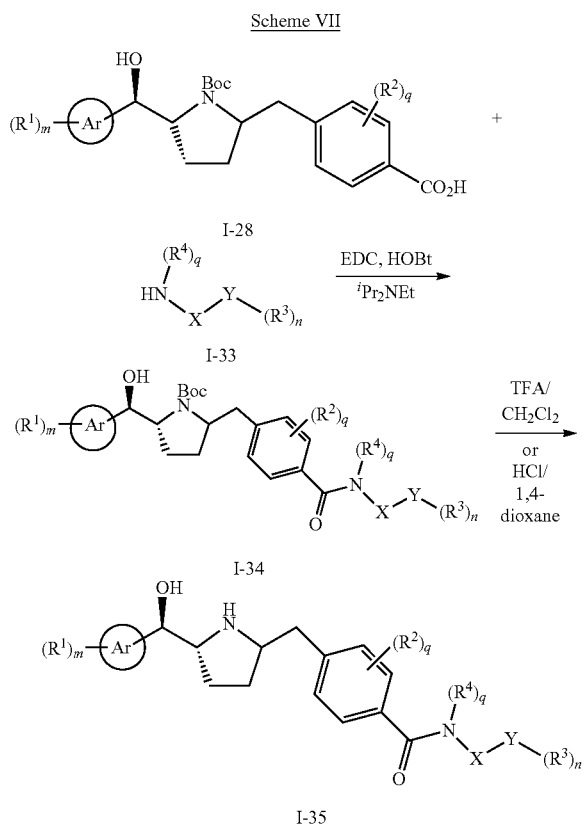

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

4-({(2S,5R)-1-(tert-butoxycarbonyl)-5-[(R)-hydroxy (phenyl)methyl]pyrrolidin-2-yl}methyl)benzoic Acid (i-1)

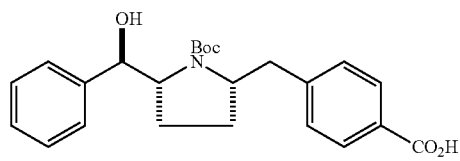

Step A: tert-butyl (4R,5R)-2,2-dimethyl-4-[(1E)-3-oxoprop-1-en-1-yl]-5-phenyl-1,3-oxazolidine-3-carboxylate

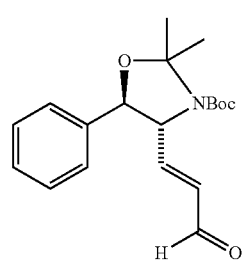 [SMILES: CC(C)(C)OC(=O)N1[C@H](/C=C/C=O)[C@@H](c2ccccc2)OC1(C)C]

Compound tert-butyl (4S,5R)-4-formyl-2,2-dimethyl-5-phenyl-1,3-oxazolidine-3-carboxylate (1.30 g, 4.26 mmol) in dichloromethane (10 ml) at ambient temperature was added to (triphenylphosphoranylidene)acetaldehyde (1.69 g, 5.54 mmol). The reaction mixture was stirred at ambient temperature for 40 h. After removal of the solvent, the residue was purified by using a Biotage Horizon® system (0-20% ethyl acetate/hexanes mixture) to afford the title compound (0.96 g, 68%) as a viscous oil. $^1$H NMR (CDCl$_3$, 500 MHz): δ9.61 (d, J=7.6 Hz, 1H), 7.42-7.37 (m, 5H), 6.73 (m, 1H), 5.96 (dd, J=15.8, 7.7 Hz, 1H), 4.78 (m, 1H), 4.29 (br, 1H), 1.80-1.41 (m, 15H). LC-MS 354.3 (M+23).

Step B: 3-oxazolidinecarboxylic acid, 2,2-dimethyl-4-(3-oxopropyl)-5-phenyl-1,1-dimethylethyl Ester, (4R, 5R)

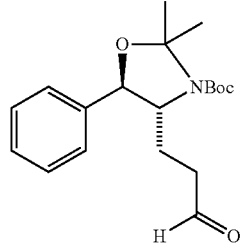 [SMILES: CC(C)(C)OC(=O)N1[C@H](CCC=O)[C@@H](c2ccccc2)OC1(C)C]

To a solution of the title compound from Step A above (19.6 g, 59.1 mmol) in acetone (150 ml) was added 10% palladium on activated carbon (1.9 g). The reaction mixture was flushed with N$_2$ then it was stirred at ambient temperature under a hydrogen balloon for 24 h. The palladium was filtered off on celite. After removal of the solvent, the residue was purified by using a Biotage Horizon® system (0-20% then 20% ethyl acetate/hexanes mixture) to afford the title compound (11.5 g, 58%) as colorless oil. $^1$H NMR (CDCl$_3$, 500 MHz): δ9.77 (s, 1H), 7.46-7.35 (m, 5H), 4.73 (d, J=7.3 Hz, 1H), 3.92 (m, 1H), 2.50-2.44 (m, 2H), 2.25-2.07 (m, 2H), 1.67 (s, 3H), 1.60 (s, 3H), 1.52 (s, 9H). LC-MS 356.4 (M+23).

Step C: tert-butyl (4R,5R)-4-{(3E)-4-[4-(methoxycarbonyl)phenyl]but-3-en-1-yl}-2,2-dimethyl-5-phenyl-1,3-oxazolidine-3-carboxylate and tert-butyl (4R, 5R)-4-{(3Z)-4-[4-(methoxycarbonyl)phenyl]but-3-en-1-yl}-2,2-dimethyl-5-phenyl-1,3-oxazolidine-3-carboxylate

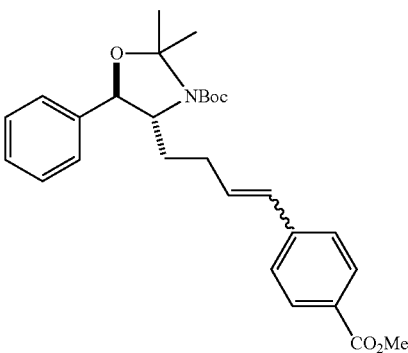 [SMILES: COC(=O)c1ccc(C=CCC[C@@H]2[C@@H](c3ccccc3)OC(C)(C)N2C(=O)OC(C)(C)C)cc1]

To a solution of 4-carbomethoxybenzyl triphenylphosphonium chloride (7.68 g, 17.2 mmol) in dimethyl sulfoxide (40 ml) in ambient temperature water bath was added sodium tert-butoxide (1.58 g, 16.4 mmol) in portions. The reaction mixture was stirred at ambient temperature for 45 minutes then was added a solution of the title compound from Step B above (5.21 g, 15.6 mmol) in DMSO (10 ml). The reaction mixture was stirred at ambient temperature for 1.5 h. 200 ml of ether was added and the solid was filtered off. The filtrate was washed with water and the solvent was removed under reduced pressure. The residue was purified by using a Biotage Horizon® system (0-10% then 10% ethyl acetate/hexanes mixture) to afford the title compound as a cis/trans mixture (5.64 g, 77%). LC-MS 488.4 (M+23).

Step D: methyl 4-[(1E,5R,6R)-5-amino-6-hydroxy-6-phenylhex-1-en-1-yl]benzoate and methyl 4-[(1Z,5R,6R)-5-amino-6-hydroxy-6-phenylhex-1-en-1-yl]benzoate

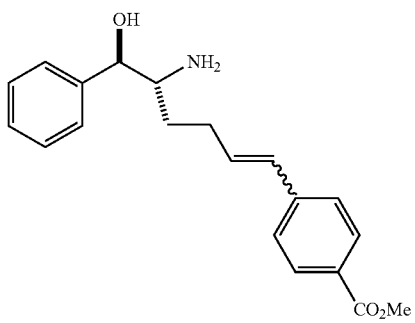 [SMILES: COC(=O)c1ccc(C=CCC[C@@H](N)[C@H](O)c2ccccc2)cc1]

Acetyl chloride (3.55 ml, 50.0 mmol) was added to methanol (50 ml) at 0° C. After being stirred at that temperature for 1 h, the resulting hydrogen chloride methanol solution was added to the title compound from Step C above (5.64 g, 12.1 mmol). The reaction mixture was stirred at ambient temperature for 5 h. About 100 ml ether was added to the reaction mixture and the solid was collected. After removal most of the solvent of the filtrate under reduced pressure, more ether was added and the solid was collected again by filtration. Combined white solid (2.96 g, 61%) was obtained as hydrogen chloride salt of the title compounds which contains both cis and trans olefin. LC-MS 326.2 (M+1).

Step E: methyl 4-((1E,5R,6R)-5-{[(benzyloxy)carbonyl]amino}-6-{[tert-butyl(dimethyl)silyl]oxy}-6-phenylhex-1-en-1-yl)benzoate and methyl 4-((1Z,5R,6R)-5-{[(benzyloxy)carbonyl]amino}-6-{[tert-butyl(dimethyl)silyl]oxy}-6-phenylhex-1-en-1-yl)benzoate

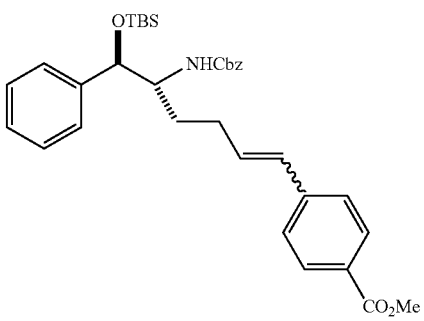 [SMILES: COC(=O)c1ccc(C=CCC[C@@H](NC(=O)OCc2ccccc2)[C@H](O[Si](C)(C)C(C)(C)C)c2ccccc2)cc1]

To a solution of the title compound from Step D above (2.96 g, 8.18 mmol) in dichloromethane (40 ml) and N,N-dimethylformamide (5 ml) was added N,N-diisopropylethylamine (5.84 ml, 32.7 mmol), followed by tert-butyldimethylsilyl chloride (1.60 g, 10.6 mmol). The reaction mixture was stirred at ambient temperature for 2 h. Saturated NaHCO$_3$ (50 ml) was added to quench the reaction and the organic layer was separated, dried over Na$_2$SO$_4$. After removal of the volatiles, the residue was purified by using a Biotage Horizon® system (0-5% then 5% methanol with 10% ammonia/dichloromethane mixture) to afford the TBS intermediate as a cis/trans mixture (3.65 g, 100%). LC-MS 440.3 (M+1).

The TBS intermediate (4.37 g, 9.95 mmol) in dichloromethane (80 ml) at −78° C. was added N,N-diisopropylethylamine (3.46 ml, 19.9 mmol) followed by benzyl chloroformate (1.83 ml, 13.0 mmol). The reaction mixture was stirred at −78° C. for 30 minutes, then at ambient temperature for 4 h. Saturated NaHCO$_3$ (50 ml) was added to quench the reaction and the organic layer was separated. After removal of the volatiles, the residue was purified by column chromatography eluting with 0-10% then 10% ethyl acetate in hexanes to afford the title compound as a cis/trans mixture (3.3 g, 58%). MS: m/z (ESI) 574 (M+1).

Step F: methyl 4-[3-((3R,4R)-3-{[(benzyloxy)carbonyl]amino}-4-{[tert-butyl(dimethyl)silyl]oxy}-4-phenylbutyl)oxiran-2-yl]benzoate

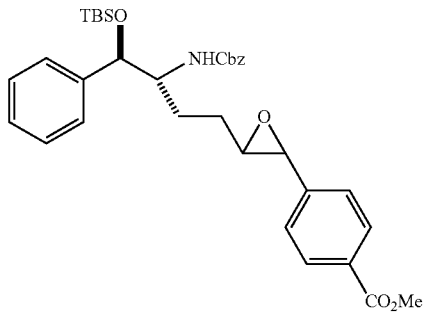 [SMILES: COC(=O)c1ccc(C2OC2CC[C@@H](NC(=O)OCc2ccccc2)[C@H](O[Si](C)(C)C(C)(C)C)c2ccccc2)cc1]

To a solution of the title compound from Step E above (0.880 g, 1.85 mmol) in dichloromethane (20 ml) was added 3-chloroperbenzoic acid (0.60 g, 2.0 mmol) in portions. The reaction mixture was stirred at ambient temperature overnight and it was then washed with sodium carbonate and dried over magnesium sulfate. After concentration, the residue was purified by flash column chromatography (0-70% ethyl acetate in hexanes) and 0.90 g (100%) of the title compound was obtained as mixture of diastereomers. MS: m/z (ESI) 590 (M+1).

Step G: methyl 4-((5R,6R)-5-{[(benzyloxy)carbonyl]amino}-6-{[tert-butyl(dimethyl)silyl]oxy}-2-oxo-6-phenylhexyl)benzoate

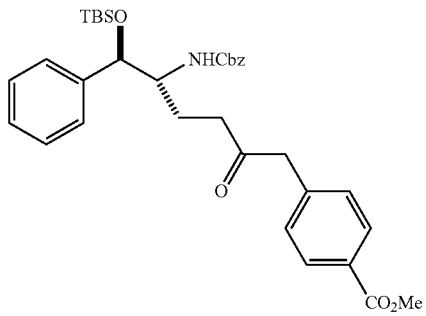 [SMILES: COC(=O)c1ccc(CC(=O)CC[C@@H](NC(=O)OCc2ccccc2)[C@H](O[Si](C)(C)C(C)(C)C)c2ccccc2)cc1]

A mixture of the title compound from Step F above (1.00 g, 1.69 mmol) and palladium acetate Pd(OAc)$_2$ (0.064 g, 0.28 mmol) in ethanol (15 ml) was degassed and flushed with N$_2$, and then triphenylphosphine (0.298 g, 1.137 mmol) was added. The reaction mixture was refluxed overnight. After removal of the solvent, the residue was purified by column chromatography (0-20% then 20% ethyl acetate in hexanes). 0.50 g (50%) of the title compound was obtained. $^1$H NMR (CDCl$_3$, 400 MHz): δ8.14 (d, J=8.6 Hz, 2H), 7.53-7.28 (m, 12H), 5.13 (s, 2H), 4.97 (d, J=9.4 Hz, 1H), 4.86 (s, 1H), 4.06 (s, 3H), 3.85 (s, 2H), 2.77-2.64 (m, 2H), 2.07 (m, 1H), 1.85-1.79 (m, 2H), 1.05 (s, 9H), 0.19 (s, 3H), 0.00 (s, 3H). MS: m/z (ESI) 590 (M+1).

Step H: methyl 4-({(2S,5R)-5-[(R)-{[tert-butyl(dimethyl)silyl]oxy}(phenyl)methyl]pyrrolidin-2-yl}methyl)benzoate

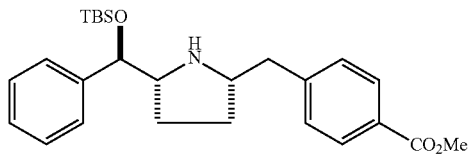 [SMILES: COC(=O)c1ccc(C[C@@H]2CC[C@H]([C@H](O[Si](C)(C)C(C)(C)C)c3ccccc3)N2)cc1]

To a solution of the title compound from Step G above (9.00 g, 0.625 mmol) in ethanol (200 ml) was added 3.0 g of 10% Pd/C under argon. The reaction mixture was stirred at 50° C. under a H$_2$ balloon overnight. After filtration and removal of the solvent, 6.0 g (90%) of the title compound was obtained which was directly used for the next step without further purification. $^1$H NMR (CDCl$_3$, 400 MHz): δ7.89 (d, J=7.9 Hz, 2H), 7.24-7.19 (m, 7H), 4.40 (d, J=7.0 Hz, 1H), 3.82 (s, 3H), 3.26-3.09 (m, 2H), 2.75 (d, J=7.0 Hz, 2H), 1.71-1.63 (m, 2H), 1.33-1.25 (m, 2H), 0.75 (s, 9H), 0.00 (s, 6H). MS: m/z (ESI) 440 (M+1).

Step I: tert-butyl (2R,5S)-2-[(R)-{[tert-butyl(dimethyl)silyl]oxy}(phenyl)methyl]-5-[4-(methoxycarbonyl)benzyl]pyrrolidine-1-carboxylate

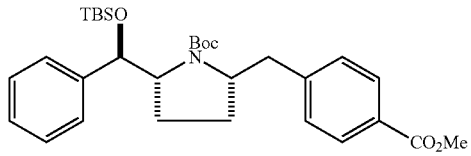 [SMILES: COC(=O)c1ccc(C[C@@H]2CC[C@H]([C@H](O[Si](C)(C)C(C)(C)C)c3ccccc3)N2C(=O)OC(C)(C)C)cc1]

To a solution of the title compound from Step H (1.01 g 2.29 mmol) in tetrahydrofuran (10 ml) was added di-tert-butyl dicarbonate (0.749 g 3.43 mmol) and the reaction mixture was allowed to stir at ambient temperature overnight. After concentration, the residue was purified by using a Biotage Horizon® system (0-10% ethyl acetate/hexanes mixture) to afford the title compound (0.81 g, 66%) as a colorless viscous oil. LC-MS 562.3 (M+23).

Step J: 4-({(2S,5R)-1-(tert-butoxycarbonyl)-5-[(R)-hydroxy(phenyl)methyl]pyrrolidin-2-yl}methyl)benzoic Acid (i-1)

To the title compound from Step 1 above (1.30 g, 2.41 mmol) was added 10 ml of 2N tetrabutylammonium fluoride tetrahydrofuran solution and the reaction mixture was allowed to stir at ambient temperature overnight. The reaction mixture was poured into water (50 ml), extracted with tert-butyl methyl ether (20 ml×3). The combined organic layers were washed with water, dried over anhydrous sodium sulfate, and concentrated. 1.00 g (100%) of the hydroxyl ester compound was obtained which was directly used for the next step without further purification. $^1$H NMR (CDCl$_3$, 400 MHz): δ7.93 (d, J=8.2 Hz, 2H), 7.31-7.19 (m, 7H), 4.39 (d, J=8.6 Hz, 1H), 4.09-4.01 (m, 2H), 3.84 (s, 3H), 3.08 (br, 1H), 2.54 (br, 2H), 1.67-1.41 (m, 13H). MS: m/z (ESI) 426 (M+1).

To a solution of the hydroxyl eater compound (4.50 g, 10.6 mmol) in methanol (100 ml) was added lithium hydroxide (1.30 g, 54.2 mmol) and water (50 ml), and the reaction mixture was stirred at ambient temperature overnight. Water (20 ml) was added, and the reaction mixture was extracted with ether (50 ml). The aqueous layer was adjusted to pH 4.5 using 1N hydrochloric acid solution, then extracted with ethyl acetate (50 mL×3). The combined organic layers were washed with brine, dried over anhydrous sodium sulfate, concentrated to afford the title compound (i-1) (2.6 g, 60%) as a white solid. $^1$H NMR (CDCl$_3$, 400 MHz): δ7.98 (d, J=7.82 Hz, 2H), 7.30~7.19 (m, 7H), 4.46 (d, 8.6 Hz, 1H), 4.09-4.03 (m, 2H), 3.40 (s, 1H), 3.09 (br, 1H), 2.53 (br, 1H), 1.65-1.43 (m, 13H). MS: m/z (ESI) 412 (M+1).

INTERMEDIATE 2

4-Methoxybenzyl{(1R)-1-[(R)-{[tert-butyl(dimethyl)silyl]oxy}(6-chloropyridin-3-yl)methyl]pent-4-yn-1-yl}carbamate (i-2)

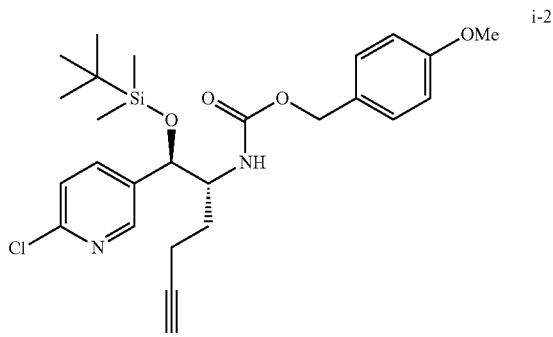 [SMILES: C#CCC[C@@H](NC(=O)OCc1ccc(OC)cc1)[C@H](O[Si](C)(C)C(C)(C)C)c1ccc(Cl)nc1]

Step A: (4S)-4-Benzyl-3-hex-5-ynoyl-1,3-oxazolidin-2-one

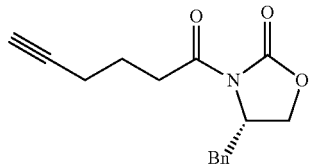 [SMILES: C#CCCCC(=O)N1C(=O)OC[C@@H]1Cc1ccccc1]

To a solution of 10 g (89 mmol) of 5-hexynoic acid and 31.0 mL (223 mmol) of triethylamine in 450 mL of anhydrous tetrahydrofuran at −25° C. under an atmosphere of nitrogen was added 12 mL (98 mmol) of trimethylacetyl chloride over 20 min. Upon addition a white precipitate formed and the resulting suspension was stirred for 2 h. Next, 4.2 g (98 mmol) of anhydrous lithium chloride and 17 g (94 mmol) of (S)-(−)-4-benzyl-2-oxazolidinone were added sequentially and the mixture was allowed to gradually warm to ambient temperature over 12 h. All volatiles were removed in vacuo and the residue was diluted with water (500 mL) and extracted with ether (3×200 mL). The combined organic layers were washed with brine (100 mL), dried over magnesium sulfate, filtered and concentrated in vacuo. The crude residue was purified by silica gel chromatography eluting with a 10-25% ethyl acetate in hexanes gradient to afford the title compound as a colorless solid (22 g, 93%). $^1$H NMR (500 MHz, CDCl$_3$): δ7.35-7.31 (m, 2H), 7.28-7.25 (m, 1H), 7.19-7.21 (m, 2H), 4.69-4.64 (m, 1H), 4.22-4.15 (m, 2H), 3.28 (dd, J=13.4, 3.3 Hz, 1H), 3.13-3.01 (m, 2H), 2.78 (dd, J=13.4, 9.6 Hz, 1H), 2.34-2.30 (m, 2H), 1.99 (t, J=2.7 Hz, 1H), 1.96-1.88 (m, 2H). LC-MS: m/z (ES) 272.2 (MH)$^+$, 294.3 (MNa)$^+$.

Step B: (4S)-4-Benzyl-3-{(2R)-2-[(S)-(6-chloropyridin-3-yl)(hydroxy)methyl]hex-5-ynoyl}-1,3-oxazinan-2-one

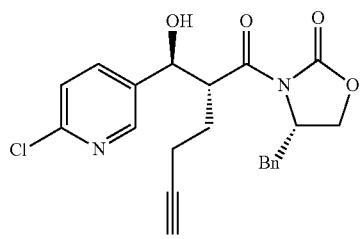 [SMILES: C#CCC[C@@H](C(=O)N1C(=O)OC[C@@H]1Cc1ccccc1)[C@H](O)c1ccc(Cl)nc1]

To a stirred solution of 23.0 g (837 mmol) of the title compound from step A above in 200 mL of anhydrous ethyl acetate at ambient temperature under an atmosphere of nitrogen was added 1.6 g (17 mmol) of anhydrous magnesium chloride, 23.0 mL (166 mmol) of triethylamine, 14.0 g (100 mmol) of 6-chloropyridine-3-carboxaldehyde and 16.0 mL (124 mmol) of chlorotrimethylsilane and the resulting mixture was stirred for 72 h. The heterogeneous reaction mixture was filtered through a 300 mL plug of silica gel eluting with an additional 1 L of ethyl acetate. The filtrate was evaporated to dryness in vacuo and the residue suspended in 200 mL of methanol and 5.0 mL of trifluoroacetic acid. The resulting mixture was stirred at ambient temperature under nitrogen for 5 h during which time the reaction became homogeneous. All volatiles were then removed in vacuo and the residue was purified by silica gel chromatography eluting with a 10-15% ethyl acetate in hexanes gradient to afford the title compound as a white solid (30 g, 88%). LC-MS: m/z (ES) 413.2 (MH)$^+$.

Step C: (4S)-4-Benzyl-3-{(2R)-2-[(S)-{[tert-butyl (dimethyl)silyl]oxy}(6-chloropyridin-3-yl)methyl] hex-5-ynoyl}-1,3-oxazinan-2-one

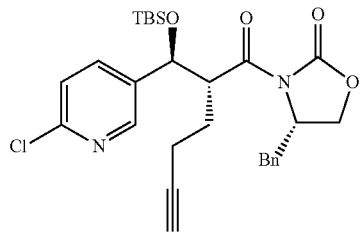 [SMILES: C#CCC[C@@H](C(=O)N1C(=O)OC[C@@H]1Cc1ccccc1)[C@H](O[Si](C)(C)C(C)(C)C)c1ccc(Cl)nc1]

To a stirred solution of 297 g (71.9 mmol) of the title compound from Step B above and 15.0 mL (126 mmol) of 2,6-lutidine in 300 mL of anhydrous dichloromethane at 0° C. under an atmosphere of nitrogen was added 22 mL (94 mmol) of tert-butyldimethylsilyl trifluoromethanesulfonate at a rate slow enough to keep the internal temperature below 3° C. The reaction mixture was stirred for 16 h at 0° C. then evaporated in vacuo to remove all volatiles. The residue was diluted with 400 mL of water and extracted with diethyl ether (3×300 mL). The combined organics were washed sequentially with a 0.5 M aqueous hydrochloric acid solution (100 mL), water (100 mL), brine (100 mL) then dried over magnesium sulfate. After filtration and evaporation in vacuo the residue was purified by silica gel chromatography eluting with a 5-8% ethyl acetate in hexanes gradient to afford the title compound as a colorless foam (37 g, 97%). LC-MS: m/z (ES) 527.3 (MH)$^+$.

Step D: (2R)-2-[(S)-{[Tert-butyl(dimethyl)silyl]oxy} (6-chloropyridin-3-yl)methyl]hex-5-ynoic acid

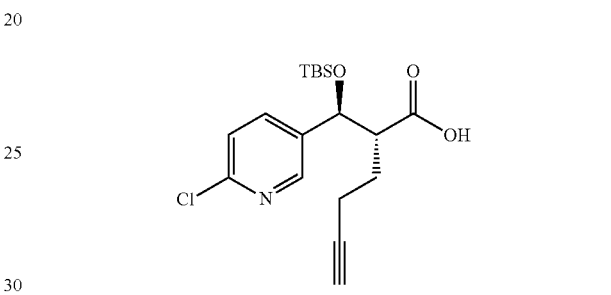

To a stirred solution of 37 g (70 mmol) of the title compound from Step C above in 520 mL of a 3 to 1 mixture of anhydrous tetrahydrofuran to water at 0° C. under an atmosphere of nitrogen was added 30 mL (350 mmol) of a 35% aqueous hydrogen peroxide solution at a rate slow enough to keep the internal temperature below 3° C. Next, 140 mL (140 mmol) of a 1.0 M aqueous sodium hydroxide solution was added at a rate slow enough to keep the internal temperature of the reaction below 5° C. After complete addition the resulting mixture was stirred for 18 h at 0° C. then quenched with a solution of 350 mL (420 mmol) of a 1.2 M aqueous sodium sulfite solution at a rate slow enough to keep the internal temperature of the mixture below 15° C. All volatiles were removed in vacuo and the remaining aqueous phase was cooled to 0° C. and acidified with a 2.5 M aqueous hydrogen chloride solution until a pH of 3 was achieved. The aqueous phase was then extracted with ethyl acetate (3×200 mL) and the combined organics were washed with brine (10 ml), dried over magnesium sulfate, filtered and evaporated in vacuo. The residue was purified by silica gel chromatography eluting with 15% ethyl acetate and 3% acetic acid in hexanes to afford the title compound as a white solid (16 g, 62%). LC-MS: m/z (ES) 368.2 (MH)$^+$.

Step E: 4-Methoxybenzyl{(1R)-1-[(R)-{[tert-butyl (dimethyl)silyl]oxy}(6-chloropyridin-3-yl)methyl] pent-4-yn-1-yl}carbamate (i-2)

To a solution of 16 g (44 mmol) of the title compound from Step D above and 12 mL (87 mmol) of triethylamine in 150 mL of anhydrous toluene at ambient temperature under an atmosphere of nitrogen was added 10 mL (46 mmol) of diphenylphosphoryl azide. The mixture was stirred for 6 h and then 14.0 mL (109 mmol) of 4-methoxybenzyl alcohol was added. The resulting mixture was heated to 100° C. for 16 h, cooled to ambient temperature and then evaporated in vacuo to remove all volatiles. The crude residue was purified by silica gel chromatography eluting with 15% ethyl acetate in hexanes to afford the title compound (i-2) as a yellow foam (17 g, 78%). $^1$H NMR (500 MHz, CDCl$_3$): δ 8.28 (d, J=2.0 Hz, 1H), 7.53 (dd, J=8.2, 2.3 Hz, 1H), 7.22 (d, J=8.4 Hz, 2H), 7.18 (d, J=8.2 Hz, 1H), 6.90 (d, J=8.4 Hz, 2H), 4.96-4.89 (m, 2H), 4.82 (d, J=2.5 Hz, 1H), 4.74 (d, J=9.6 Hz, 1H), 3.90-3.84 (m, 1H), 3.82 (s, 3H), 2.30-2.26 (m, 2H), 1.97 (t, J=2.5 Hz, 1H), 1.89-1.83 (m, 1H), 1.58-1.52 (m, 1H), 0.89 (s, 9H), 0.08 (s, 3H), −0.12 (s, 3H). LC-MS: m/z (ES) 503.3 (MH)$^+$.

INTERMEDIATE 3

4-({(2S,5R)-1-(tert-butoxycarbonyl)-5-[(R)-{[tert-butyl(dimethyl)silyl]oxy}(pyridin-3-yl)methyl]pyrrolidin-2-yl}methyl)benzoic Acid (i-3);

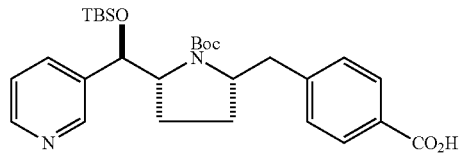

Step A: Methyl 4-[(5R,6R)-6-{[tert-butyl(dimethyl)silyl]oxy}-6-(6-chloropyridin-3-yl)-5-({[(4-methoxybenzyl)oxy]carbonyl}amino)hex-1-yn-1-yl]benzoate

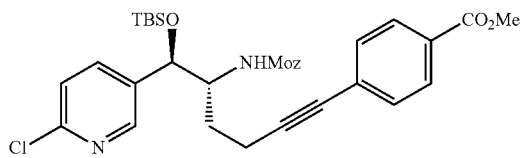

Methyl 4-iodobenzoate (54.4 g, 0.21 mol), 4-methoxybenzyl{(1R)-1-[(R)-{[tert-butyl(dimethyl)silyl]oxy}(6-chloropyridin-3-yl)methyl]pent-4-yn-1-yl}carbamate (i-2) (95.0 g, 0.19 mol) and triethylamine (79.0 mL, 0.57 mol) were suspended in N,N-dimethylformamide (500 mL) and nitrogen was bubbled through the reaction mixture for 15 min. Then tetrakis(triphenylphosphine)palladium (11.0 g, 9.5 mmol) and copper(I) iodide (3.61 g, 1.9 mmol) were added and the resulting reaction mixture was stirred at ambient temperature overnight. The reaction was slowly quenched with water and extracted with ethyl acetate. The combined extracts were washed with water, brine, dried over Na$_2$SO$_4$, filtered and evaporated. The residue was purified by column chromatography (petroleum ether/ethyl acetate=10:1) to give 92.1 g (77%) of the title compound as a yellow foam. $^1$H NMR (400 MHz, CDCl$_3$): δ 8.46 (s, 1H), 8.10 (d, J=7.8 Hz, 2H), 7.71 (d, J=7.8 Hz, 1H), 7.59 (d, J=8.6 Hz, 2H), 7.51 (d, J=8.6 Hz, 1H), 7.47-7.42 (m, 3H), 7.37-7.35 (m, 2H), 5.11 (d, J=7.0 Hz, 1H), 5.06-4.92 (m, 3H), 4.13-4.06 (m, 1H), 3.93 (s, 6H), 2.69 (t, J=7.0 Hz, 2H), 2.61-2.54 (m, 1H), 2.15-2.11 (m, 1H), 0.80 (s, 9H), 0.20 (s, 3H), 0.00 (s, 3H). MS: m/z (ESI) 637 (M+23).

Step B: Methyl 4-[(5R,6R)-5-amino-6-{[tert-butyl(dimethyl)silyl]oxy}-6-(6-chloropyridin-3-yl)hex-1-yn-1-yl]benzoate

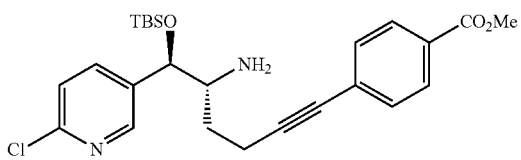 [SMILES: COC(=O)c1ccc(C#CCC[C@@H](N)[C@H](O[Si](C)(C)C(C)(C)C)c2ccc(Cl)nc2)cc1]

To a stirred solution of the title compound from Step A (83.0 g, 0.13 mol) in dichloromethane (400 mL) was added triethylamine (20 mL) and the resulting mixture was stirred for 3 h. The reaction mixture turned to dark red color. All volatiles were evaporated and the residue was diluted with water and based by NaHCO$_3$. It was then extracted with dichloromethane (3×250 mL). The combined organic layers were washed with water and brine, dried over Na$_2$SO$_4$ and concentrated. The residue was purified by column chromatography with dichloromethane/methanol=20:1 to afford 47.0 g (77%) of the title compound as yellow gum. $^1$H NMR (400 MHz, CDCl$_3$): δ 8.35 (s, 1H), 7.95 (d, J=8.6 Hz, 2H), 7.63 (d, J=7.8 Hz, 1H), 7.41 (d, J=8.6 Hz, 2H), 7.31 (d, J=8.6 Hz, 1H), 4.55 (d, J=4.7 Hz, 1H), 3.93 (s, 3H), 2.96-2.93 (m, 1H), 2.64-2.53 (m, 2H), 1.71-1.68 (m, 1H), 1.52-1.41 (m, 3H), 0.90 (s, 9H), 0.20 (s, 3H), 0.00 (s, 3H). MS: m/z. (EST) 473 (M+1).

Step C: Tert-butyl (2R,5S)-2-[(R)-{[tert-butyl(dimethyl)silyl]oxy}(6-chloropyridin-3-yl)methyl]-5-[4-(methoxycarbonyl)benzyl]pyrrolidine-1-carboxylate and Tert-butyl (2R,5R)-2-[(R)-{[tert-butyl](dimethyl)silyl]oxy}(6-chloropyridin-3-yl)methyl]-5-[4-(methoxycarbonyl)benzyl]pyrrolidine-1-carboxylate

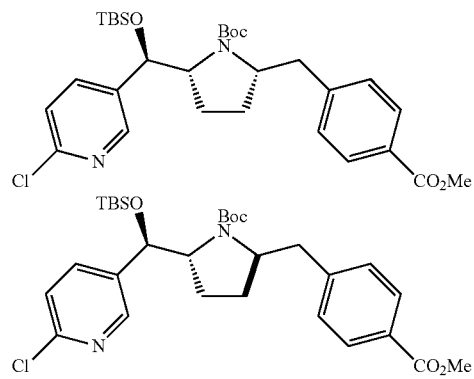

A stirred solution of the title compound from Step B (47.0 g, 99.3 mmol) in toluene (800 mL) was degassed by argon gas, then platinumdichloride (2.64 g, 9.93 mmol) was added. The resulting mixture was heated to 80° C. overnight under argon. The reaction mixture was concentrated to afford 47 g of product which was used in the next step without purification. MS: m/z (EST) 473 (M+1).

To a cooled (0° C.), stirred solution of unpurified product (47 g, 99 mmol) from the above step in dichloromethane (500 mL) was added 4 A molecular sieve followed by sodium triacetoxyborohydride (42.2 g, 199 mmol). The reaction mixture was allowed to warm to RT and stirred overnight. Methanol (50 mL) was added. The reaction mixture was filtered and concentrated. Dichloromethane (100 mL) and saturated sodium bicarbonate (100 mL) were added and the organic layer was separated. The aqueous layer was extracted with dichloromethane. The combined organic layers were washed with water and brine, dried over $Na_2SO_4$ and concentrated to afford 47 g of product which was used in the next step without further purification. MS: m/z (ESI) 473 (M+1).

To a stirred solution of unpurified product (47 g, 99 mmol) from the above step in dichloromethane (400 mL) was added N,N-diisopropylethylamine (25.9 mL, 148 mmol), followed by slow addition of di-tert-butyl dicarbonate (24.9 g, 114 mmol). The resulting solution was stirred at ambient temperature for 5 h, and then the solvent was evaporated. The residue was purified by column chromatography (petroleum ether/ethyl acetate=80:1 then 50:1).

First spot to elute (cis isomer): tert-butyl (2R,5S)-2-[(R)-{[tert-butyl(dimethyl)silyl]oxy}(6-chloropyridin-3-yl)methyl]-5-[4-(methoxycarbonyl)benzyl]pyrrolidine-1-carboxylate as a colorless foam (15.2 g, 26%). $^1$H NMR (400 MHz, $CDCl_3$): δ 8.38 (s, 1H), 7.91 (d, J=8.1 Hz, 2H), 7.70 (d, J=7.5 Hz, 1H), 7.37 (d, J=8.2 Hz, 1H), 7.03 (s, 2H), 5.65-5.55 (m, 1H), 4.12-3.09 (m, 1H), 3.91 (s, 3H), 3.86-3.73 (m, 1H), 3.11-2.93 (m, 1H), 2.71-2.68 (m, 1H), 1.98-1.82 (m, 2H), 1.59 (s, 9H), 1.32-1.28 (m, 2H), 0.95 (s, 9H), 0.16 (s, 3H), 0.00 (s, 3H). MS: m/z (ESI) 575 (M+1).

Second spot to elute (trans isomer): tert-butyl (2R,5R)-2-[(R)-{[tert-butyl(dimethyl)silyl]oxy}(6-chloropyridin-3-yl)methyl]-5-[4-(methoxycarbonyl)benzyl]pyrrolidine-1-carboxylate as a colorless gum (5.1 g, 9%): $^1$H NMR (400 MHz, $CDCl_3$): δ 8.59 (s, 1H), 8.30 (d, J=7.9 Hz, 2H), 7.84 (d, J=7.6 Hz, 1H), 7.45-7.34 (m, 3H), 5.71 (s, 1H), 4.28-4.14 (m, 1H), 3.95 (s, 3H), 3.93-3.91 (m, 1H), 3.36-3.33 (m, 1H), 2.84-2.75 (m, 1H), 2.43-2.33 (m, 1H), 1.77-1.59 (m, 13H), 0.95 (s, 9H), 0.16 (s, 3H), 0.00 (s, 3H). MS: m/z (EST) 575 (M+1).

Step D: Tert-butyl (2R,5S)-2-[(R)-{[tert-butyl(dimethyl)silyl]oxy}(pyridin-3-yl)methyl]-5-[4-(methoxycarbonyl)benzyl]pyrrolidine-1-carboxylate

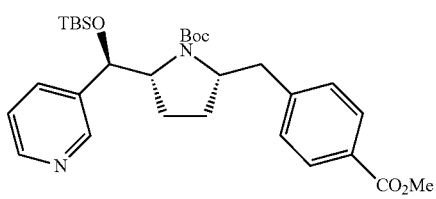 [SMILES: COC(=O)c1ccc(C[C@@H]2CC[C@H]([C@H](O[Si](C)(C)C(C)(C)C)c3cccnc3)N2C(=O)OC(C)(C)C)cc1]

To a solution of tert-butyl (2R,5S)-2-[(R)-{[tert-butyl(dimethyl)silyl]oxy}(6-chloropyridin-3-yl)methyl]-5-[4-(methoxycarbonyl)benzyl]pyrrolidine-1-carboxylate from Step C (14.0 g, 24.3 mmol) in ethanol (200 mL) was added potassium acetate (3.58, 36.5 mmol) and 10% palladium on carbon (4.0 g) under argon. The reaction mixture was heated to 50° C. and agitated under an atmosphere of hydrogen at 50 psi for 14 h. The mixture was cooled to RT and filtered. The filtrate was concentrated to afford 12.1 g (92%) of the title compound as yellow foam. $^1$H NMR (400 MHz, $CDCl_3$): δ 8.62 (s, 1H), 8.58 (s, 1H), 7.89 (d, J=7.9 Hz, 2H), 7.36-7.32 (m, 1H), 7.02-6.99 (m, 2H), 5.62 (s, 1H), 4.20-4.11 (m, 2H), 3.94 (s, 3H), 2.99-2.96 (m, 1H), 2.64-2.60 (m, 1H), 2.02-1.88 (m, 2H), 1.61 (s, 9H), 1.56-1.43 (m, 2H), 0.96 (s, 9H), 0.17 (s, 3H), 0.00 (s, 3H). MS: m/z (ESI) 541 (M+1).

Step E: 4-({(2S,5R)-1-(tert-butoxycarbonyl)-5-[(R)-{[tert-butyl(dimethyl)silyl]oxy}(pyridin-3-yl)methyl]pyrrolidin-2-yl}methyl)benzoic acid (i-3)

To a stirred solution of the title compound from Step D (2.5 g, 4.6 mmol) in methanol/water 4:1 (30 mL) was added lithium hydroxide (533 mg, 23.1 mmol). The resulting mixture was stirred at RT overnight. The mixture was diluted with water and extracted with ether. The aqueous layer was acidified with 1N citric acid to PH 4.5, and then extracted with ethyl acetate. The organic layer was separated and washed with water, brine, dried over $Na_2SO_4$, and concentrated. The residue was purified by reverse phase HPLC (Luna10u, 250× 50 mm I.D.; 45-65% 0.1% trifluoroacetic acid in acetonitrile/0.1% trifluoroacetic acid in water gradient) to afford 1.31 g (74%) of the title compound (i-3) as a white solid. $^1$H NMR (400 MHz, $CDCl_3$): δ 8.64 (s, 2H), 7.93 (d, J=7.8 Hz, 2H), 7.80 (s, 1H), 7.44-7.38 (m, 1H), 7.03 (s, 2H), 5.66-5.33 (m, 1H), 4.16 (s, 1H), 4.00-3.88 (m, 1H), 3.01-2.95 (m, 1H), 2.68-1.58 (m, 1H), 2.04-1.83 (m, 2H), 1.60 (s, 9H), 1.31-1.20 (m, 2H), 0.96 (s, 9H), 0.17 (s, 3H), 0.00 (s, 3H). MS: m/z (ESI) 527 (M+1).

INTERMEDIATE 4

4-({(2S,5R)-1-(tert-butoxycarbonyl)-5-[(R)-hydroxy(pyridin-3-yl)methyl]pyrrolidin-2-yl}methyl)benzoic acid (i-4)

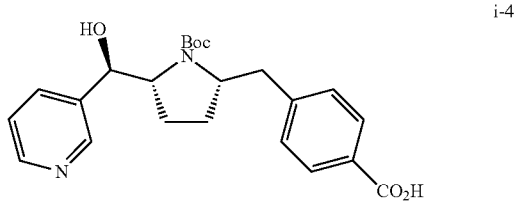 [SMILES: CC(C)(C)OC(=O)N1[C@H](Cc2ccc(C(=O)O)cc2)CC[C@@H]1[C@H](O)c1cccnc1]

Step A: Tert-butyl (2R,5S)-2-[(R)-hydroxy(pyridin-3-yl)methyl]-5-[4-(methoxycarbonyl)benzyl]pyrrolidine-1-carboxylate

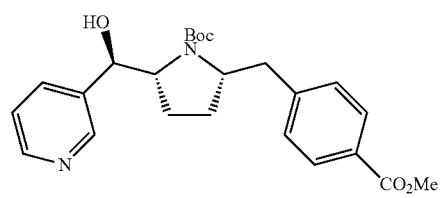

A solution of tert-butyl (2R,5S)-2-[(R)-{[tert-butyl(dimethyl)silyl]oxy}(pyridin-3-yl)methyl]-5-[4-(methoxycarbonyl)benzyl]pyrrolidine-1-carboxylate (11.0 g, 20.3 mmol) in 100 mL of 2 M tetrabutylammonium fluoride tetrahydrofuran solution was stirred at RT overnight. The mixture was then diluted with water and extracted with ethyl acetate (50 mL×3). The combined organic layers were washed with water, brine, dried over Na$_2$SO$_4$, and concentrated to afford 8.51 g (98%) of the title compound. $^1$H NMR (400 MHz, CDCl$_3$): δ 8.55 (s, 2H), 7.93 (d, J=8.0 Hz, 2H), 7.76 (d, J=8.0 Hz, 1H), 7.34-7.28 (m, 3H), 6.36 (s, 1H), 4.54 (d, J=8.5 Hz, 1H), 4.18-4.09 (m, 2H), 3.92 (s, 3H), 3.23 (s, 1H), 3.13-3.10 (m, 1H), 2.61-2.52 (m, 1H), 1.78-1.60 (m, 2H), 1.49 (s, 9H). MS: m/z (ESI) 427 (M+1).

Step B: 4-({(2S,5R)-1-(tert-butoxycarbonyl)-5-[(R)-hydroxy(pyridin-3-yl)methyl]pyrrolidin-2-yl}methyl)benzoic acid (i-4)

To a stirred solution of the title compound from Step A (8.51 g, 20.0 mmol) in methanol/water=4:1 (50 mL) was added lithium hydroxide (2.39 g, 100 mmol). The resulting mixture was stirred at RT overnight. The mixture was diluted with water and extracted with ether. The aqueous layer was acidified with 1N citric acid to PH 4.5, and then extracted with ethyl acetate. The organic layer was separated and washed with water, brine, dried over Na$_2$SO$_4$, and concentrated. The residue was purified by SFC (using an AD column 35% MeOH/65% CO$_2$, 150 ml/min 100 bar) to afford 6.90 g (84%) of the title compound (i-4) as a white solid. $^1$H NMR (400 MHz, CDCl$_3$): δ 8.53 (s, 2H), 8.00 (d, J=7.7 Hz, 2H), 7.77 (d, J=6.4 Hz, 1H), 7.32-7.29 (m, 1H), 7.21 (d, J=8.0 Hz, 2H), 5.22 (s, 1H), 4.51 (d, J=8.4 Hz, 1H), 4.13-4.11 (m, 1H), 4.09-4.01 (m, 1H), 3.07-3.04 (m, 1H), 2.58-2.56 (m, 1H), 1.68-1.51 (m, 2H), 1.42 (s, 9H). MS: m/z (EST) 413 (M+1).

INTERMEDIATE 5

4-({(2S,5R)-1-(tert-butoxycarbonyl)-5-[(R)-{[tert-butyl(dimethyl)silyl]oxy}(phenyl)methyl]pyrrolidin-2-yl}methyl)benzoic Acid

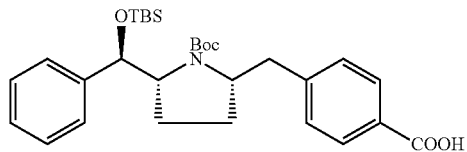

I-5

Step A: 4-methoxybenzyl{(1R)-5-(4-bromophenyl)-1-[(R)-{[tert-butyl(dimethyl)silyl]oxy}-1-phenylhex-5-yn-2-amine

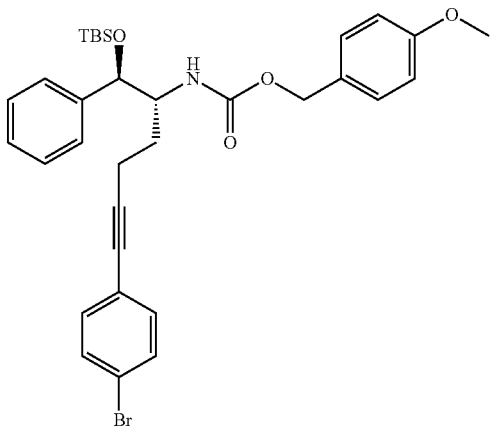 [SMILES: COc1ccc(COC(=O)N[C@H](CCC#Cc2ccc(Br)cc2)[C@H](O[Si](C)(C)C(C)(C)C)c2ccccc2)cc1]

To a solution of 4-methoxybenzyl{(1R)-1-[(R)-{[tert-butyl(dimethyl)silyl]oxy}(phenyl)methyl]pent-4-yn-1-yl}carbamate (25.0 g, 53.5 mmol), triethylamine (74.5 ml, 535 mmol), copper(I) iodide (0.611 g, 3.21 mmol) and 1-bromo-4-iodobenzene (16.6 g, 58.8 mmol) in DMF (250 ml) was added PdCl$_2$(dppf)-CH$_2$Cl$_2$ (1.31 g, 1.60 mmol) and the mixture was degassed three times and stirred at RT for 6 h. LC-MS showed no more starting material left. Poured into water 750 ml, the mixture was extracted with ethyl acetate (3×500 mL). The combined organic fractions were washed with water and brine (500 mL), dried with sodium sulfate and filtered and the solvent was evaporated under reduced pressure. The residue was purified by column chromatography on silica gel Biotage 65i, eluting with EtOAc to afford the title compound as an orange oil. Yield is 86%. LC-MS: m/z (E/S) 624.1 (MH)$^+$.

Step B: (1R,2R)-6-(4-bromophenyl)-1-{[tert-butyl(dimethyl)silyl]oxy}-1-phenylhex-5-yn-2-amine

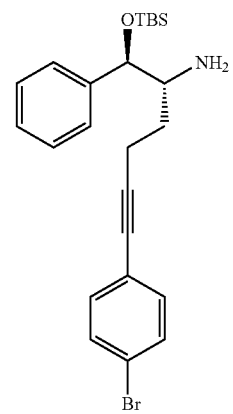 [SMILES: CC(C)(C)[Si](C)(C)O[C@H](c1ccccc1)[C@H](N)CCC#Cc1ccc(Br)cc1]

To a solution of the title compound from Step A (29.0 g, 46.6 mmol) in CH$_2$Cl$_2$ (200 ml) was added TFA (20 ml) and the reaction was stirred at RT for 3 h. LC-MS showed no more starting left. The residue was evaporated to dryness. The residue was purified by column chromatography on silica gel Biotage 40M, eluting with EtOAc/isohexane to afford the title compound as an orange oil. Yield is 89%. LC-MS: m/z (E/S) 460.1 (MH)$^+$.

Step C: (2S,5R)-2-(4-bromophenyl)-5-[(R)-{[tert-butyl(dimethyl)silyl]oxy}(phenyl)methyl]pyrrolidine

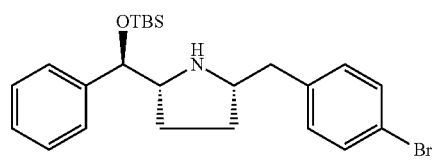 [SMILES: CC(C)(C)[Si](C)(C)O[C@H](c1ccccc1)[C@H]1CC[C@@H](Cc2ccc(Br)cc2)N1]

To a solution of the title compound from Step B (5.00 g, 10.9 mmol) in toluene (50 ml) was added platinum (II) chloride (0.290 g, 1.09 mmol). The mixture of degassed by bubble nitrogen for 25 min and the mixture was stirred at 80° C. for 6 h under nitrogen. The resulting product was filtered through celite and the solvent was removed and the resulting product was dissolved in CH$_2$Cl$_2$ (50.0 ml), sodium triacetoxyborohydride (5.78 g, 27.3 mmol) was added to it at 0° C. The mixture was stirred at RT overnight. The mixture was cooled, diluted with dichloromethane (250 mL), washed with aqueous sodium hydrogen carbonate (saturated, 3×100 mL), dried (Na$_2$SO$_4$), filtered and the solvent was evaporated under reduced pressure. The residue was purified by column chromatography on silica gel Biotage 40M, eluting with Acetone/hexane 10%-20% to afford the title compound as colorless solid. Yield is 24%. LC-MS: m/z (E/S) 460.3 (MH)$^+$.

Step D: tert-butyl (2S,5R)-2-(4-bromophenyl)-5-[(R)-{[tert-butyl(dimethyl)silyl]oxy}(phenyl)methyl]pyrrolidine-1-carboxylate

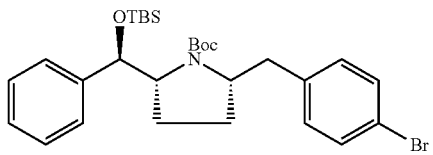 [SMILES: CC(C)(C)OC(=O)N1[C@H](Cc2ccc(Br)cc2)CC[C@@H]1[C@H](O[Si](C)(C)C(C)(C)C)c1ccccc1]

To a solution of the title compound from Step C (1.20 g, 2.61 mmol) and N,N-diisopropylethylamine (0.910 ml, 5.21 mmol) in CH$_2$Cl$_2$ (15 ml) was added BOC$_2$O (1.21 ml, 5.21 mmol) and the mixture was stirred at RT for overnight. The mixture was diluted with ethyl acetate (200 mL), washed with aqueous sodium hydrogen carbonate (saturated, 2×100 mL), with) brine (100 mL), dried (Na$_2$SO$_4$), filtered and the solvent was evaporated under reduced pressure. The residue was purified by column chromatography on silica gel Biotage 40M, eluting with EtOAc/isohexane 0%-10% to afford title compound as a colorless solid. Yield is 96%. LC-MS: m/z (E/S) 562.1 (MH)$^+$.

Step E: tert-butyl (2R,5S)-2-[(R)-{[tert-butyl(dimethyl)silyl]oxy}(phenyl)methyl]-5-[4-(methoxycarbonyl)benzyl]pyrrolidine-1-carboxylate

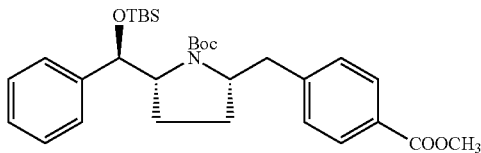 [SMILES: COC(=O)c1ccc(C[C@@H]2CC[C@H]([C@H](O[Si](C)(C)C(C)(C)C)c3ccccc3)N2C(=O)OC(C)(C)C)cc1]

To a solution of the title compound from Step D and triethylamine (0.125 ml, 0.896 mmol) in MeOH (1 ml) was added Pd(OAc)$_2$ (5.03 mg, 0.0220 mmol) and the mixture was degassed three times filled with CO and stirred at 120° C. for overnight. LC-MS showed no more starting material left. The mixture was diluted with ethyl acetate, washed with aqueous sodium hydrogen carbonate (saturated, 3×10 mL), and brine, dried (Na$_2$SO$_4$), filtered and the solvent was evaporated under reduced pressure. The residue was purified by preparative TLC eluting with 10%/90% EtOAc/isohexane to afford title compound. Yield is 56%. LC-MS: m/z (E/S) 539.2 (MH)$^+$.

Step F: 4-({(2S,5R)-1-(tert-butoxycarbonyl)-5-[(R)-{[tert-butyl(dimethyl)silyl]oxy}(phenyl)methyl]-pyrrolidin-2-yl}methyl)benzoic acid (I-5)

To a solution of the title compound from Step E (800 mg, 1.48 mmol) in MeOH (7.5 ml) was added 1 N LiOH (7.41 ml, 7.41 mmol) and the mixture was stirred at RT overnight. LC-MS showed no more starting material left. The mixture was evaporated to remove MeOH, extracted the aqueous layer with ether 3×50 ml, the aqueous layer was adjusted to PH=4.5 with 1N HCl, then extracted with ethyl acetate 3×50 ml. The combined organic layers was washed with brine (saturated, 1×50 mL), dried (Na$_2$SO$_4$), filtered and the solvent evaporated under reduced pressure to afford title compound (i-5). Yield is 99%. LC-MS: m/z (E/S) 526.2 (MH)$^+$.

INTERMEDIATE 6

4-Methyl-2-pyrimidinemethanamine (i-6)

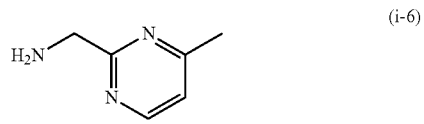

Step A: 2-Cyano-4-methylpyrimidine

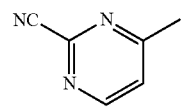

To a solution of 2-chloro-4-methylpyrimidine (1 g, 7.78 mmol) and zinc cyanide (475 mg, 4.04 mmol) in anhydrous DMF (10 ml) was added Pd(PPh$_3$)$_4$ (449 mg, 0.366 mmol) and nitrogen flushed through the mixture for 5 min. The mixture was heated at 180° C. for 30 min in a microwave reactor. The reaction was repeated on the same scale and the reaction mixtures were combined. The mixture was partitioned between EtOAc and water (filtered through celite to remove some insolubles), and the organic layer washed with sat. NaCl, dried over MgSO$_4$, filtered and evaporated. The residue was purified by MPLC (Biotage Horizon: FLASH 25+M) eluent: 100% Hexanes (90 ml), gradient rising from 100% Hexanes to 15% EtOAc in Hexanes (900 ml), then 15% EtOAc in Hexanes (500 ml) to give 1 g of the title compound (54%) as an off-white solid. $^1$H NMR (CDCl$_3$): 2.62 (s, 3H), 7.42 (d, J5.1 Hz, 1H), 8.69 (d, J5.1 Hz, 1H).

Step B: 4-Methyl-2-pyrimidinemethanamine (i-6)

To a nitrogen flushed solution of the title compound from Step A (1 g, 8.39 mmol) in methanol (40 ml) was added 10% palladium on carbon (100 mg) and the resulting mixture stirred under a balloon of hydrogen for 3 h. The mixture was filtered through celite and evaporated to give 950 mg (91%) of the title compound (i-6) as an orange oil. $^1$HNMR (CDCl$_3$): 2.54 (s, 3H), 4.16 (s, 2H), 7.03 (d, J5.0 Hz, 1H), 8.56 (d, J5.0 Hz, 1H).

INTERMEDIATE 7

4-(Trifluoromethyl)-2-pyrimidinemethanamine (i-7)

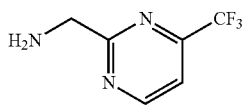

Step A: 2-Cyano-4-(trifluoromethyl)pyrimidine

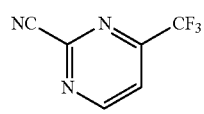

Prepared according to the procedure described in Intermediate 6 step A, replacing 2-chloro-4-methylpyrimidine with 2-chloro-4-(trifluoromethyl)pyrimidine, (39%) as an off-white solid. $^1$H NMR (CDCl$_3$): 7.91 (d, J5.1 Hz, 1H), 9.20 (d, J5.1 Hz, 1H).

Step B: 4-(Trifluoromethyl)-2-pyrimidinemethanamine (i-7)

Prepared from the title compound from Step A according to the procedure described in Intermediate 6, step B. MS (m/z): 178 (M+1).

INTERMEDIATE 8

4-Cyclopropyl-2-pyrimidinemethanamine (i-8)

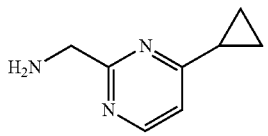

Step A: 2-Chloro-4-cyclopropylpyrimidine

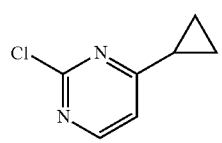

Nitrogen gas was bubbled through a mixture of 2,4-dichloropyrimidine (1.49 g, 10 mmol), cyclopropaneboronic acid (0.86 g, 10 mmol) and K$_3$PO$_4$ (5.31 g, 25 mmol) in THF (50 ml) for 10 min. Pd(dppf)Cl$_2$ (817 mg, 1 mmol) was added and the mixture heated at 90° C. in a sealed tube overnight. The mixture was cooled and partitioned between water and EtOAc, the organic layer washed with sat. NaCl, dried over MgSO$_4$, filtered and evaporated. The residue purified by MPLC (Biotage Horizon: FLASH 25+M) eluent: 100% Hexanes (90 ml), gradient rising from 100% Hexanes to 20% EtOAc in Hexanes (900 ml), then 20% EtOAc in Hexanes (500 ml) to give 750 mg (48%) as an off-white solid. $^1$H NMR (CDCl$_3$): 1.18 (m, 4H), 1.99 (m, 1H), 7.09 (d, J5.1 Hz, 1H), 8.36 (d, J5.1 Hz, 1H).

Step B: 2-Cyano-4-cyclopropylpyrimidine

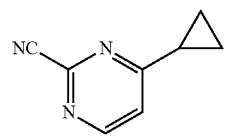 [SMILES: N#Cc1nccc(C2CC2)n1]

Prepared according to the procedure described in Intermediate 6, step A, replacing 2-chloro-4-methylpyrimidine with 2-chloro-4-cyclopropylpyrimidine, (82%) as an off-white solid. $^1$H NMR (CDCl$_3$): 1.23 (m, 4H), 2.05 (on, 1H), 7.38 (d, J5.2 Hz, 1H), 8.56 (d, J5.2 Hz, 1H).

Step C: 4-Cyclopropyl-2-pyrimidinemethanamine (i-8)

Prepared from the title compound from Step B according to the procedure described in Intermediate 6, step B (96%). $^1$H NMR (CDCl$_3$): 1.07 (m, 2H), 1.18 (m, 2H), 1.99 (m, 1H), 4.07 (s, 2H), 6.99 (d, J5.2 Hz, 1H), 8.46 (d, J5.2 Hz, 1H).

INTERMEDIATE 9

4-Cyclopropyl-6-methyl-2-pyrimidinemethanamine (i-9)

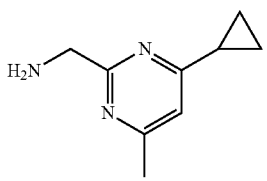

Step A: 2-Chloro-4-cyclopropyl-6-methylpyrimidine

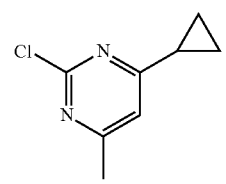

Prepared according to the procedure described in Intermediate 8, Step A, replacing 2,4-dichloropyrimidine with 2,4- dichloro-6-methylpyrimidine, (51%) as an off-white solid. ¹H NMR (CDCl₃): 1.12 (m, 2H), 1.19 (m, 2H), 1.94 (m, 1H), 2.47 (s, 3H), 6.95 (s, 1H).

Step B: 2-Cyano-4-cyclopropyl-6-methylpyrimidine

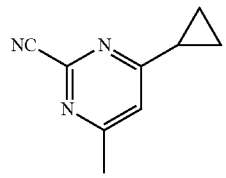

Prepared according to the procedure described in Intermediate 6, step A, replacing 2-chloro-4-methylpyrimidine with 2-chloro-4-cyclopropyl-6-methylpyrimidine, (82%) as a white solid. ¹H NMR (CDCl₃): 1.16 (m, 2H), 1.20 (m, 2H), 1.98 (m, 1H), 2.53 (s, 3H), 7.22 (s, 1H).

Step C: 4-Cyclopropyl-6-methyl-2-pyrimidinemethanamine (i-9)

Prepared from the title compound from Step B according to the procedure described in Intermediate 6, step B (87%) orange oil. ¹H NMR (CDCl₃): 1.03 (m, 2H), 1.15 (m, 2H), 1.92 (m, 1H), 2.44 (s, 3H), 4.01 (s, 2H), 6.85 (s, 1H).

INTERMEDIATE 10

4-Phenyl-2-pyrimidinemethanamine (i-10)

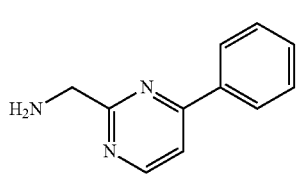

(i-10)

Step A: 2-Chloro-4-phenylpyrimidine

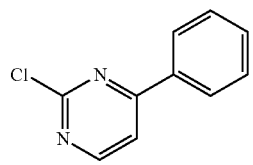 [SMILES: Clc1nccc(-c2ccccc2)n1]

To a mixture of 2,4-dichloropyrimidine (1.47 g, 9.8 mmol), benzene boronic acid (1 g, 8.2 mmol), Na₂CO₃ (2.61 g, 24.6 mmol) in a mixture of DME (15 ml), EtOH (2 ml) and water (3 ml) was added Pd(PPh₃)₄ (190 mg, 0.16 mmol) and the resulting mixture heated in a microwave at 125° C. for 30 min. The reaction was repeated on same scale. The reaction mixtures were combined and diluted with water and extracted with EtOAc (×2). The EtOAc layers were combined and washed with sat. NaCl, dried over MgSO₄, filtered and evaporated. The residue was purified by MPLC (Biotage Horizon: FLASH 40+M) eluent: 100% Hexanes (180 ml), gradient rising from 100% Hexanes to 10% EtOAc in Hexanes (900 ml), then 10% EtOAc in Hexanes (500 ml) to give 1.3 g of the title compound (41%) as a white solid. ¹H NMR (CDCl₃): 7.54 (m, 3H), 7.76 (s, 1H), 8.08 (m, 2H), 9.04 (s, 1H).

Step B: 2-Cyano-4-phenylpyrimidine

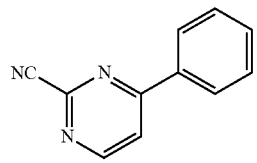 [SMILES: N#Cc1nccc(-c2ccccc2)n1]

Prepared according to the procedure described in Intermediate 6, step A, replacing 2-chloro-4-methylpyrimidine with 2-chloro-4-phenylpyrimidine, (70%) as an off-white solid. ¹H NMR (CDCl₃): 7.59 (m, 3H), 8.03 (s, 1H), 8.15 (m, 2H), 9.38 (s, 1H).

Step C: 4-Phenyl-2-pyrimidinemethanamine (i-10)

Prepared from the title compound from Step B according to the procedure described in Intermediate 6, step B. ¹H NMR (CDCl₃): 4.07 (s, 2H), 7.52 (m, 3H), 7.78 (s, 1H), 8.11 (m, 2H), 9.21 (s, 1H).

INTERMEDIATE 11

4-Methyl-6-phenyl-2-pyrimidinemethanamine (i-11)

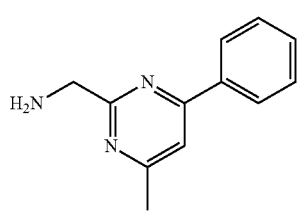

(i-11)

Step A: 2-Chloro-4-methyl-6-phenylpyrimidine

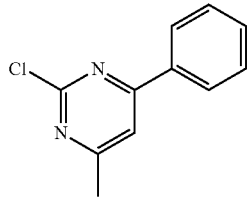

A mixture of 2,4-dichloro-6-methylpyrimidine (5 g, 30.7 mmol), benzeneboronic acid (3.74 g, 30.7 mmol), K₂CO₃ (12.72 g, 92 mmol) and Pd(PPh₃)₄ (1.06 g, 0.92 mmol) in toluene (150 ml) and methanol (35 ml) was degassed with nitrogen and heated at 90° C. overnight. The mixture was cooled and water (200 ml) added. The organic layer was separated and the aqueous extracted with EtOAc (×2). The organic layers were combined and dried over MgSO₄, filtered and evaporated. The residue was purified by MPLC (Biotage Horizon: FLASH 40+M) eluent: 100% Hexanes (180 ml), gradient rising from 100% Hexanes to 20% EtOAc in Hexanes (1800 ml), then 20% EtOAc in Hexanes (1000 ml) to give 3 g (48%). $^1$H NMR (CDCl$_3$): 2.61 (s, 3H), 7.52 (m, 4H), 8.08 (m, 2H).

Step B: 2-Cyano-4-methyl-6-phenylpyrimidine

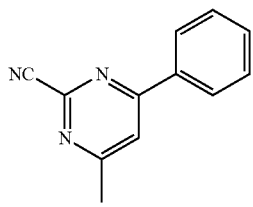

Prepared according to the procedure described in Intermediate 6, step A, replacing 2-chloro-4-methylpyrimidine with 2-chloro-4-methyl-6-phenylpyrimidine, (70%) as an off-white solid. $^1$H NMR (CDCl$_3$): 2.66 (s, 3H), 7.54 (m, 3H), 7.75 (s, 1H), 8.11 (m, 2H).

Step C: 4-Methyl-6-phenyl-2-pyrimidinemethanamine (i-11)

Prepared from the title compound from Step B according to the procedure described in Intermediate 6, step B, as an orange oil. $^1$H NMR (CDCl$_3$): 2.57 (s, 3H), 4.27 (s, 2H), 7.48 (m, 4H), 8.12 (m, 2H).

INTERMEDIATE 12

5-Phenyl-2-pyrimidinemethanamine (i-12)

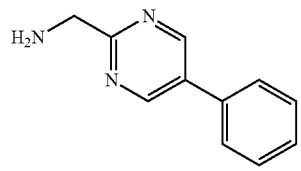

(i-12)

Step A: 2-Chloro-5-phenylpyrimidine

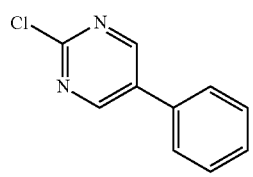 [SMILES: Clc1ncc(-c2ccccc2)cn1]

Prepared according to the procedure described in Intermediate 11, step A, replacing 2,4-dichloro-6-methylpyrimidine with 2-chloro-5-bromopyrimidine, (53%) as an off-white solid. $^1$H NMR (CDCl$_3$): 7.57 (m, 5H), 8.86 (s, 2H).

Step B: 2-Cyano-5-phenylpyrimidine

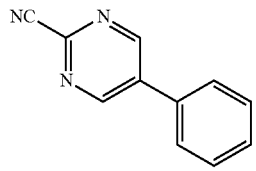 [SMILES: N#Cc1ncc(-c2ccccc2)cn1]

Prepared according to the procedure described in Intermediate 6, step A, replacing 2-chloro-4-methylpyrimidine with 2-chloro-5-phenylpyrimidine, (70%) as an off-white solid. $^1$H NMR (CDCl$_3$): 7.64 (m, 5H), 9.08 (s, 2H).

Step C: 5-Phenyl-2-pyrimidinemethanamine (i-12)

Prepared from the title compound from Step B according to the procedure described in Intermediate 6, step B. $^1$H NMR (CDCl$_3$): 4.30 (s, 2H), 7.58 (m, 5H), 8.95 (s, 2H).

INTERMEDIATE 13

6-Phenyl-4-pyrimidinemethanamine (i-13)

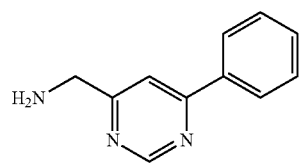

(i-13)

Step A: 4-Chloro-6-phenylpyrimidine

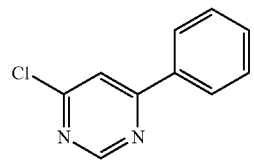 [SMILES: Clc1cc(-c2ccccc2)ncn1]

Prepared according to the procedure described in Intermediate 11, step A, replacing 2,4-dichloropyrimidine with 4,6-dichloropyrimidine, (83%) as a white solid. $^1$H NMR (CDCl$_3$): 7.54 (m, 3H), 7.76 (s, 1H), 8.08 (m, 2H), 9.05 (s, 1H).

Step B: 4-Cyano-6-phenylpyrimidine

Prepared according to the procedure described in Intermediate 6, step A, replacing 2-chloro-4-methylpyrimidine with 4-chloro-6-phenylpyrimidine, (70%) as an off-white solid. $^1$H NMR (CDCl$_3$): 7.59 (m, 3H), 8.03 (s, 1H), 8.15 (m, 2H), 9.38 (s, 1H).

Step C: 6-Phenyl-4-pyrimidinemethanamine (i-13)

Prepared from the title compound from Step B according to the procedure described in Intermediate 6, step 13. $^1$H NMR (CDCl$_3$): 2.00 (brs, 2H), 4.05 (s, 2H), 7.52 (m, 3H), 7.78 (s, 1H), 8.11 (m, 2H), 9.21 (s, 1H).

INTERMEDIATE 14

1-(6-Methylpyridin-2-yl)ethanamine (i-14)

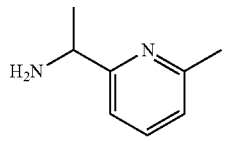
(i-14)

To a solution of 2-acetyl-6-methylpyridine (4.7 g, 34.8 mmol) in anhydrous methanol (100 ml) was added ammonium acetate (26.8 g, 348 mmol) and sodium cyanoborohydride (1.75 g, 27.8 mmol) and the resulting mixture stirred at RT overnight. The mixture was evaporated and the residue dissolved in water and basified by the addition of KOH and extracted with DCM (×3). The DCM layers were combined and washed with sat. NaCl, dried over MgSO$_4$, filtered and evaporated. The residue was purified by column chromatography on silica to afford the title compound (i-14) (eluent: 5% MeOH in DCM) to give 2.8 g (59%) as a clear oil. $^1$H NMR (CDCl$_3$): 1.41 (d, J6.7 Hz, 3H), 1.78 (brs, 2H), 2.54 (s, 3H), 4.21 (q, J6.7 Hz, 1H), 6.99 (d, J7.6 Hz, 1H), 7.09 (d, J7.7 Hz, 1H), 7.52 (m, 1H).

INTERMEDIATE 15

1-(Pyrazin-2-yl)ethylamine (i-15)

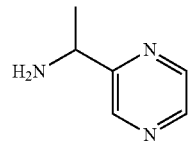
(i-15)

Prepared according to the procedure described in Intermediate 14, replacing 2-acetyl-6-methylpyridine with acetylpyrazine to yield the title compound (i-15) (60%) as a light yellow oil. $^1$H NMR (CDCl$_3$): 1.42 (d, J6.7 Hz, 3H), 1.86 (brs, 2H), 2.54 (s, 3H), 4.19 (q, J6.7 Hz, 1H), 8.41 (d, J2.5 Hz, 1H), 8.47 (t, J2.2 Hz, 1H), 8.59 (d, J2.2 Hz, 1H).

INTERMEDIATE 16

N-(pyridazin-3-ylmethyl)cyclopropanamine (i-16)

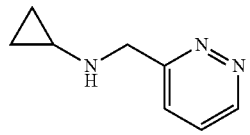
(i-16)

To a solution of pyridazin-3-ylmethanol (300 mg, 2.72 mmol) in DCM (25 mL) and triethylamine (0.42 mL, 3.01 mmol) at 0° C. was added methanesulfonyl chloride (0.24 mL, 3.08 mmol), and the mixture was stirred for 1 hour at room temperature. The reaction was monitored by TLC and upon completion, the reaction mixture was transferred to a separatory funnel and quenched with saturated sodium bicarbonate, partitioned with DCM, and the aqueous layer was extracted with DCM (3×50 mL). The combined organic extracts were washed with brine, dried with Na$_2$SO$_4$, filtered, and concentrated in vacuo. The resulting intermediate mesylate was a brown oil and was unstable, therefore it was used in the next step without further purification. LC-MS 189.0 (M+1)$^+$.

To a vigorously stirred room temperature slurry of the crude mesylate (0.210 g, 1.12 mmol) in DCM (10 mL), was added cyclopropylamine (0.24 mL, 3.42 mmol, 3 equivalents). The reaction was stirred for 60 hours and was then concentrated in vacuo and loaded directly onto a Biotage SNAP 25G column. Elution with 0-10% MeOH/DCM+1% TEA gave the desired product (65 mg, 39%) as a brown oil. $^1$H NMR (600 MHz, CDCl$_3$) δ 0.39-0.46 (m, 4H), 2.22 (m, 1H), 2.32 (bs, 1H), 4.17 (s, 2H), 7.43 (m, 1H), 7.50 (d, 1H, J=8.2 Hz), 9.09 (d, 1H, J=3.5 Hz).

INTERMEDIATE 17

N-methyl-1-(pyridazin-3-yl)methanamine (i-17)

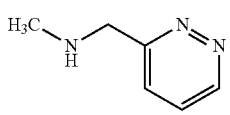
(i-17)

Following the general procedure for intermediate i-16 above using methylamine (11.4 equivalents relative to the mesylate), afforded the title compound (192 mg, 53%). $^1$H NMR (600 MHz, CDCl$_3$) δ 2.51 (s, 3H), 3.14 (s, 1H), 4.09 (s, 2H), 4.17 (s, 2H), 7.45 (m, 1H), 7.56 (m, 1H), 9.10 (m, 1H).

INTERMEDIATE 18

N-(pyridazin-3-ylmethyl)ethanamine (i-18)

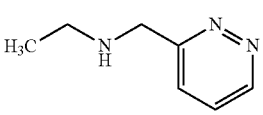
(i-18)

Following the general procedure for intermediate i-16 above using ethylamine (3.1 equivalents relative to the mesylate), afforded the title compound that also contained excess triethylamine (317 mg). $^1$H NMR (600 MHz, CDCl$_3$) δ 1.53 (t, 3H, J=7.3 Hz), 1.74 (bs, 1H), 3.19 (m, 2H), 4.60 (s, 2H), 7.58 (dd, 1H, J=8.5 Hz, 5.0 Hz), 8.13 (d, 1H, J=8.5 Hz), 9.17 (d, 1H, J=5.0 Hz). LC-MS 138.2 (M+1)$^+$.

INTERMEDIATE 19

3-methoxy-N-(pyridazin-3-ylmethyl)propan-1-amine (i-19)

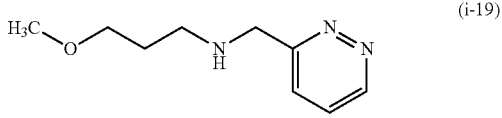

Following the general procedure for intermediate i-16 above using 3-methoxypropylamine (3.1 equivalents relative to the mesylate), afforded the title compound (28 mg, 14%). $^1$H NMR (600 MHz, CDCl$_3$) δ 1.87 (quintet, 211, J=6.2 Hz), 2.87 (t, 2H, J=5.6 Hz), 3.34 (s, 3H), 3.49 (t, 2H, J=5.8 Hz), 4.10 (bs, 1H), 4.20 (s, 2H), 7.46 (dd, 1H, J=8.2 Hz, 4.7 Hz), 7.63 (d, 1H, J=8.2 Hz), 9.11 (d, 1H, J=4.7 Hz). LC-MS 182.1 (M+1)$^+$.

INTERMEDIATE 20

N-methyl-1-(2-methyl-2H-tetrazol-5-yl)methanamine (i-20)

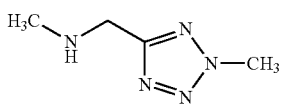

Step 1: 5-(Chloromethyl)-2-methyl-2H-tetrazole

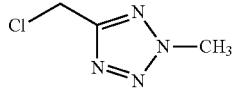

To the parent tetrazole (500 mg, 4.22 mmol) in diethyl ether (8.4 mL), was slowly added trimethylsilyldiazomethane (2.40 mL, 4.80 mmol) at 0° C. (this should be done slowly due to gas evolution). The yellow reaction was allowed to stir overnight at room temperature before being concentrated by passing a stream of nitrogen over the solution. The reaction was then purified by chromatography using a Biotage purification system and a Biotage Snap 25G silica column, eluting with 5-50% EtOAc/hexanes. The product was collected and concentrated to afford the desired product as a colorless oil (212 mg, 38%). $^1$H NMR (600 MHz, CDCl$_3$) δ 4.36 (s, 3H), 4.77 (s, 2H).

Step 2: N-methyl-1-(2-methyl-2H-tetrazol-5-yl)methanamine (i-20)

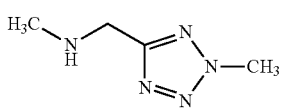

To 5-(chloromethyl)-2-methyl-2H-tetrazole (136.8 mg, 1.032 mmol), was added methylamine (4.00 mL of 2M solution in THF, 8.00 mmol). This was stirred for 16 hours at 45° C. A white precipitate formed in the reaction and it was allowed to continue stirring for another 24 hours at room temperature before being concentrated in vacuo and successively azeotroped with THF, triethylamine, methanol, and then DCM. $^1$H NMR (600 MHz, CDCl$_3$) δ 2.23 (s, 3H), 3.80 (s, 2H), 4.29 (s, 3H).

INTERMEDIATE 21

4-({(2S,5R)-1-(tert-butoxycarbonyl)-5-[(R)-{[tert-butyl(dimethyl)silyl]oxy}{6-[(2-phenylpropan-2-yl)amino]pyridin-3-yl}methyl]pyrrolidin-2-yl}methyl)benzoic Acid

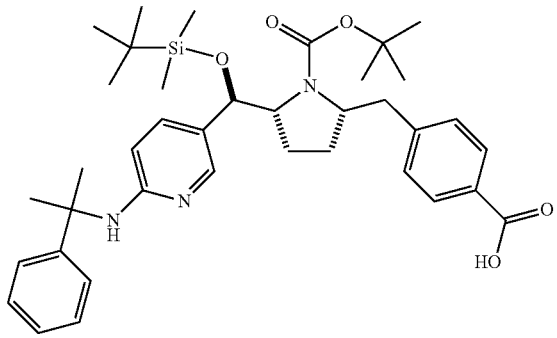

Step A: Tert-butyl (2R,5S)-2-[(R)-{[tert-butyl(dimethyl)silyl]oxy}(1-oxidopyridin-3-yl)methyl]-5-[4-(methoxycarbonyl)benzyl]pyrrolidine-1-carboxylate

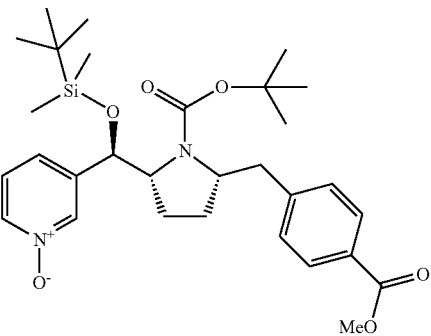 [SMILES: COC(=O)c1ccc(C[C@@H]2CC[C@H]([C@H](O[Si](C)(C)C(C)(C)C)c3ccc[n+]([O-])c3)N2C(=O)OC(C)(C)C)cc1]

A solution of tert-butyl (2R,5S)-2-[(R)-{[tert-butyl(dimethyl)silyl]oxy}(pyridin-3-yl)methyl]-5-[4-(methoxycarbonyl)benzyl]pyrrolidine-1-carboxylate (1.15 g, 2.127 mmol) in DCM (22 mL) was cooled to 0° C. and m-CPBA (0.953 g, 4.25 mmol) was added. The reaction was warmed to room temperature. After 2 hours the reaction was quenched with aqueous sodium bisulfite (20 mL). The reaction was then diluted with EtOAc (150 mL) and washed vigorously with aqueous sodium bisulfite (3×40 mL). The organics were washed with brine (2×40 mL), saturated aqueous NaHCO$_3$ (3×40 mL) and then brine (2×40 mL). The organic layer was dried over Na$_2$SO$_4$, filtered, and concentrated to afford tert-butyl (2R,5S)-2-[(R)-{[tert-butyl(dimethyl)silyl]oxy}(1-oxidopyridin-3-yl)methyl]-5-[4-(methoxycarbonyl)benzyl]pyrrolidine-1-carboxylate (1.18 g, 100%). LC-MS=557.2 (M+1)$^+$.

Step B: Tert-butyl (2R,5S)-2-[(R)-{[tert-butyl(dimethyl)silyl]oxy}{6-[(2-phenylpropan-2-yl)amino]pyridin-3-yl}methyl]-5-[4-(methoxycarbonyl)benzyl]pyrrolidine-1-carboxylate

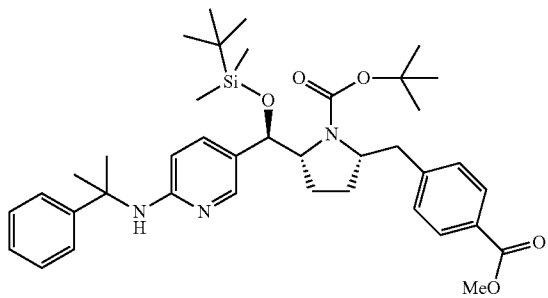 [SMILES: COC(=O)c1ccc(C[C@@H]2CC[C@H]([C@H](O[Si](C)(C)C(C)(C)C)c3ccc(NC(C)(C)c4ccccc4)nc3)N2C(=O)OC(C)(C)C)cc1]

A solution of tert-butyl (2R,5S)-2-[(R)-{[tert-butyl(dimethyl)silyl]oxy}(1-oxidopyridin-3-yl)methyl]-5-[4-(methoxycarbonyl)benzyl]pyrrolidine-1-carboxylate (0.465 g, 0.835 mmol) in trifluorotoluene (15 ml) was cooled to 0° C. Cumylamine (0.282 mL, 2.09 mmol) was added, followed by p-toluenesulfonic anhydride (0.273 g, 0.835 mmol) in 2 portions, 5 minutes apart. After 10 minutes, additional cumylamine (0.282 mL, 2.09 mmol) was added, followed by p-toluenesulfonic anhydride (0.273 g, 0.835 mmol) in 2 portions, 5 minutes apart. After 10 minutes, a third addition of cumylamine (0.282 mL, 2.088 mmol) was carried out, followed by p-toluenesulfonic anhydride (273 mg, 0.835 mmol) in 2 portions, 5 minutes apart. After 10 hours, the reaction was diluted with EtOAc (250 mL) and washed with water (2×50 mL) and brine (50 mL). The organic layer was dried over $Na_2SO_4$, filtered, and concentrated. The residue was purified by silica gel chromatography with 0-100% EtOAc/hexanes to afford tert-butyl (2R,5S)-2-[(R)-{[tert-butyl(dimethyl)silyl]oxy}{6-[(2-phenylpropan-2-yl)amino]pyridin-3-yl}methyl]-5-[4-(methoxycarbonyl)benzyl]pyrrolidine-1-carboxylate (349.1 mg, 62%). LC-MS=674.4 $(M+1)^+$. $^1$H NMR (600 MHz, $CD_3OD$) δ −0.07 (s, 3H), 0.07 (s, 3H), 0.88 (s, 9H), 1.15-1.92 (m, 20H), 2.75 & 2.46 (2 multiplets, 1H), 3.87 (m, 4H), 4.06 (bs, 1H), 5.31 & 5.12 (2 singlets, 1H), 6.00-6.10 (m, 1H), 7.07 (m, 5H), 7.23 (bs, 1H), 7.36 (bs, 2H), 7.81 (bs, 1H), 7.90 (m, 2H).

Step C: 4-({(2S,5R)-1-(tert-butoxycarbonyl)-5-[(R)-{[tert-butyl(dimethyl)silyl]oxy}{6-[(2-phenylpropan-2-yl)amino]pyridin-3-yl}methyl]pyrrolidin-2-yl}methyl)benzoic Acid

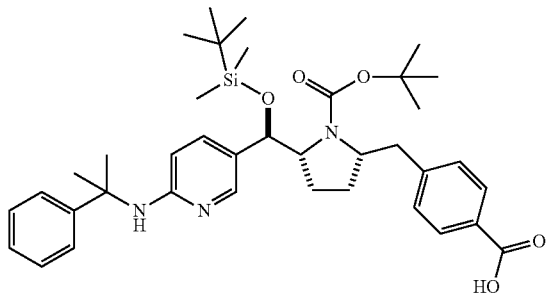

To a solution of tert-butyl (2R,5S)-2-[(R)-{[tert-butyl(dimethyl)silyl]oxy}{6-[(2-phenylpropan-2-yl)amino]pyridin-3-yl}methyl]-5-[4-(methoxycarbonyl)benzyl]pyrrolidine-1-carboxylate (0.340 g, 0.504 mmol) in dioxane (8 mL) and water (2 mL) was added 1M LiOH (1.51 mL, 1.51 mmol). The reaction was stirred vigorously at room temperature for 18 hours and then quenched with acetic acid (0.116 mL, 2.018 mmol). The reaction was diluted with EtOAc (125 mL) and washed with water (20 mL) and brine (20 mL). The organic extracts were dried over $Na_2SO_4$, filtered, and concentrated. The residue was taken up in $CH_2Cl_2$/heptanes and concentrated in vacuo to afford 4-({(2S,5R)-1-(tert-butoxycarbonyl)-5-[(R)-{[tert-butyl(dimethyl)silyl]oxy}{6-[(2-phenylpropan-2-yl)amino]pyridin-3-yl}methyl]pyrrolidin-2-yl}methyl)benzoic acid (319 mg, 96%). LC-MS=660.4 $(M+1)^+$. $^1$H NMR (600 MHz, $CD_3OD$) δ 7.90 (d, J=7.2 Hz, 2H), 7.79 (bs, 1H), 7.37 (bs, 2H), 7.28 (m, 1H), 7.02-7.12 (m, 5H), 6.13 (m, 1H), 5.31 & 5.12 (2 singlets, 1H), 4.00 (m, 1H), 3.84 (bs, 1H), 2.76 & 2.49 (2 multiplets, 1H), 1.14-1.96 (m, 20H), 0.88 (s, 9H), 0.08 (s, 3H), −0.06 (s, 3H).

Biological Assays: The following in vitro assays are suitable for screening compounds that have selective β3 agonist activity:

Functional Assay: For compounds in examples 1-50, cAMP production in response to ligand is measured according to Barton, et al. (1991, Agonist-induced desensitization of D2 dopamine receptors in human Y-79 retinoblastoma cells. Mol. Pharmacol. v3229:650-658) modified as follows. The cAMP production is measured using a homogenous time-resolved fluorescence resonance energy transfer immunoassay (LANCE™, Perkin Elmer) according to the manufacture's instructions. Chinese hamster ovary (CHO) cells, stably transfected with the cloned β-adrenergic receptor (β1, β2 or β3) are harvested after 3 days of subculturing. Harvesting of cells is done with Enzyme-free Dissociation Media (Specialty Media). Cells are then counted and resuspended in assay buffer (Hank's Balanced salt solution supplemented with 5 mM HEPES, 01% BSA) containing a phosphodiesterase inhibitor (IBMX, 0.6 mM). The reaction is initiated by mixing 6,000 cells in 6 μL with 6 μL Alexa Fluor labeled cAMP antibody (LANCE™ kit) which is then added to an assay well containing 12 μL of compound (diluted in assay buffer to 2× final concentration). The reaction proceeds for 30 minutes at RT and is terminated by the addition of 24 ul detection buffer (LANCE™ kit). The assay plate is then incubated for 1 h at RT and time-resolved fluorescence measured on a Perkin Elmer Envision reader or equivalent. The unknown cAMP level is determined by comparing fluorescence levels to a cAMP standard curve.

The non-selective, full agonist β-adrenergic ligand isoproterenol is used at all three receptors to determine maximal stimulation. The human β3 adrenergic receptor (AR) selective ligand (S)-N-[4-[2-[[2-hydroxy-3-(4-hydroxyphenoxy)propyl]amino]ethyl]-phenyl]-4-iodobenzenesulfonamide is used as a control in all assays. Isoproterenol is titrated at a final concentration in the assay of 10-10 M to 10-5 and the selective ligand (S)N-[4-[2-[[2-hydroxy-3-(4-hydroxyphenoxy)propyl]amino]ethyl]phenyl]-4-iodobenzenesulfonamide is titrated at the β3 receptor at concentration of 10-10 M to 10-5 M. Unknown ligands are titrated at all 3 β-adrenergic receptor subtypes at a final concentration in the assay of 10-10 M to 10-5 M to determine the $EC_{50}$. The $EC_{50}$ is defined as the concentration of compound that gives 50% activation of its own maximum. Data are analyzed using Microsoft Excel and Graphpad Prism or an internally developed data analysis software package.

For compounds in examples 51-137, Isoproterenol is titrated at a final concentration in the assay of 10-12 M to 10-5 and the selective ligand (S)N-[4-[2-[[2-hydroxy-3-(4-hydroxyphenoxy)propyl]amino]ethyl]phenyl]-4-iodobenzenesulfonamide is titrated at the β3 receptor at concentration of 10-12 M to 10-5 M. Unknown ligands are titrated at all 3 β-adrenergic receptor subtypes at a final concentration in the assay of 10-12 M to 10-5 M to determine the $EC_{50}$. The $EC_{50}$ is defined as the concentration of compound that gives 50% activation of its own maximum. Functional antagonist assays are performed similar to described above; however, unknown ligands are titrated at β-adrenergic receptor subtypes 1 and 2 at a final concentration in the assay of 10-12 M to 10-5 M in the presence of 10-9 M full agonist β-adrenergic ligand isoproterenol. The $EC_{50}$ is defined as the concentration of compound that gives 50% inhibition of the full agonist response. Data are analyzed using Microsoft Excel and Graphpad Prism or an internally developed data analysis software package.

Binding Assay: Compounds are also assayed at the β1 and β2 receptors to determine selectivity. All binding assays are run using membranes prepared from CHO cells recombinantly expressing β1 or β2 receptors. Cells are grown for 3-4 days post splitting; the attached cells are washed with PBS and then lysed in 1 mM Tris, pH 7.2 for 10 minutes on ice. The flasks are scraped to remove the cells and the cells then homogenized using a Teflon/glass homogenizer. Membranes are collected by centrifuging at 38,000×g for 15 minutes at 4° C. The pelleted membranes are resuspended in TME buffer (50 mM Tris, pH 7.4, 5 mM $MgCl_2$, 2 mM EDTA) at a concentration of 1 mg protein/mL. Large batches of membranes can be prepared, aliquoted and stored at −70° C. for up to a year without loss of potency. The binding assay is performed by incubating together membranes (2-5 μg of protein), the radiolabelled tracer $^{125}$I-cyanopindolol ($^{125}$I-CYP, 45 pM), 200 ug of WGA-PVT SPA beads (GE Healthcare) and the test compounds at final concentrations ranging from 10-10 M to 10-5 M in a final volume of 200 μL of TME buffer containing 0.1% BSA. The assay plate is incubated for 1 h with shaking at RT and then placed in a Perkin Elmer Trilux scintillation counter. The plates are allowed to rest in the Trilux counter for approximately 10 h in the dark prior to counting. Data are analyzed using a standard 4-parameter non-linear regression analysis using either Graphpad Prism software or an internally developed data analysis package. The $IC_{50}$ is defined as the concentration of the title compound capable of inhibiting 50% of the binding of the radiolabelled tracer ($^{125}$I-CYP). A compound's selectivity for the β3 receptor may be determined by calculating the ratio ($IC_{50}$ β1 AR, β2 AR)/($EC_{50}$ β3 AR).

The following examples are provided to illustrate the invention and are not to be construed as limiting the scope of the invention in any manner.

EXAMPLE 1

4-({(2S,5R)-5-[(R)-hydroxy(phenyl)methyl]pyrolidin-2-yl}methyl)-N-[(3-phenyl-1H-1,2,4-triazol-5-yl)methyl]benzamide

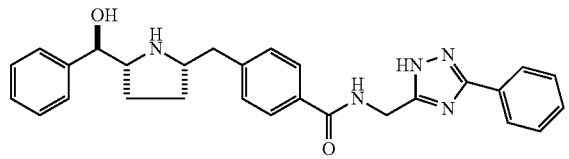

Step A: Tert-butyl (2R,5S)-2-[(R)-hydroxy(phenyl)methyl]-5-[4-({(3-phenyl-1H-1,2,4-triazol-5-yl)methyl]amino}carbonyl)benzyl]pyrrolidine-1-carboxylate

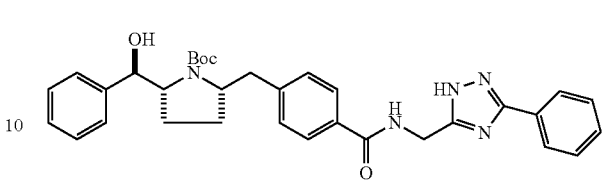

A mixture of 4-({(2S,5R)-1-(tert-butoxycarbonyl)-5-[(R)-hydroxy(phenyl)methyl]pyrrolidin-2-yl}methyl)benzoic acid (i-1, 0.020 g, 0.049 mmol) in N,N-dimethylformamide (0.5 ml) was added to 1-(3-phenyl-1H-1,2,4-triazol-5-yl)methanamine (0.018 g, 0.073 mmol) followed by 1-hydroxybenzotriazole (0.0099 g, 0.073 mmol), N-(3-dimethylaminopropyl)-N'-ethylcarbodiimide (EDC) hydrochloride (0.014 g, 0.073 mmol) and N,N-diisopropylethylamine (0.042 ml, 0.24 mmol). The reaction mixture was stirred at ambient temperature for 4 h. The mixture was directly purified by reverse phase HPLC (TMC Pro-Pac C18; 30-100% 0.1% trifluoroacetic acid in acetonitrile/0.1% trifluoroacetic acid in water gradient). The resulting pure fractions were lyophilized overnight to give the titled compound as a white solid. LC-MS 590.2 (M+23).

Step B: 4-({(2S,5R)-5-[(R)-hydroxy(phenyl)methyl]pyrrolidin-2-yl}methyl)-N-[(3-phenyl-1H-1,2,4-triazol-5-yl)methyl]benzamide

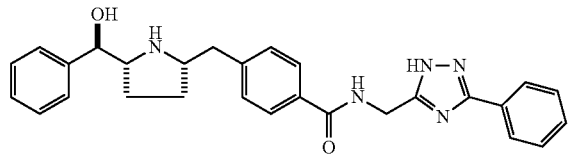 [SMILES: O=C(NCc1nc(-c2ccccc2)n[nH]1)c1ccc(C[C@@H]2CC[C@H]([C@H](O)c3ccccc3)N2)cc1]

The white solid from Step A above was added to dichloromethane (1.0 ml) followed by trifluoroacetic acid (0.3 ml) and the reaction mixture was stirred at ambient temperature for 1 h. After removal of the volatiles, the residue was purified by reverse phase HPLC (TMC Pro-Pae C18; 0-80% 0.1% trifluoroacetic acid in acetonitrile/0.1% trifluoroacetic acid in water gradient). The resulting pure fractions were lyophilized overnight to give the titled compound as trifluoroacetic acid salt. LC-MS 468.2 (M+1).

Using the Beta-3 agonist in vitro functional assay described above the human Beta-3 agonist functional activity of Example 1 was determined to be between 1 to 9.9 nM.

EXAMPLES 2-49

Using procedures similar to those described in Example 1, Examples 2-49 shown in Table 1 and Example 50 in Table 2 were prepared from the appropriate starting materials.

Using the Beta-3 agonist in vitro functional assay described above the human Beta-3 agonist functional activity of each compound was determined and shown in Tables 1 and 2 as the following ranges:
  less than 1 nM (+);
  1-9.9 nM (++);
  10-99.9 nM (+++);
  100-999 nM (++++), and
  greater than 999 nM but less than 3000 nM (+++++).

TABLE 1

| Example | A | R | MW | MS (MH)+ | Human β3 agonist functional activity |
|---|---|---|---|---|---|
| 2 | CH | 2-pyridylmethyl | 401.5 | 402.2 | +++ |
| 3 | CH | (4,6-dimethylpyrimidin-2-yl)methyl | 430.6 | 431.3 | +++ |
| 4 | CH | (3-fluoropyridin-2-yl)methyl | 419.5 | 420.3 | +++ |
| 5 | CH | (4-chloropyridin-2-yl)methyl | 435.96 | 436.3 | +++ |
| 6 | CH | (6-chloropyridin-2-yl)methyl | 436.0 | 436.2 | +++ |
| 7 | CH | (4-methoxycarbonylpyridin-2-yl)methyl | 459.6 | 460.28 | +++ |
| 8 | CH | pyridazin-3-ylmethyl | 402.5 | 403.3 | ++++ |
| 9 | CH | pyrimidin-2-ylmethyl | 402.5 | 403.3 | ++++ |
| 10 | CH | pyrazin-2-ylmethyl | 402.5 | 403.3 | ++++ |

TABLE 1-continued

| Example | A | R | MW | MS (MH)+ | Human β3 agonist functional activity |
|---|---|---|---|---|---|
| 11 | CH | pyrazin-2-yl-ethyl | 416.5 | 417.1 | +++++ |
| 12 | CH | pyrimidin-4-yl-methyl | 402.5 | 403.23 | +++ |
| 13 | CH | (3-methylpyridin-2-yl)methyl | 415.5 | 416.2 | +++ |
| 14 | CH | (4-trifluoromethylpyrimidin-2-yl)methyl | 470.5 | 471.2 | +++ |
| 15 | CH | (4-cyclopropylpyrimidin-2-yl)methyl | 442.6 | 443.3 | +++ |
| 16 | CH | (4-cyclopropyl-6-methylpyrimidin-2-yl)methyl | 456.6 | 457.2 | +++ |
| 17 | CH | (6-methylpyridin-2-yl)methyl | 415.5 | 416.2 | ++++ |
| 18 | CH | (4-methylpyrimidin-2-yl)methyl | 416.5 | 417.2 | +++ |

TABLE 1-continued
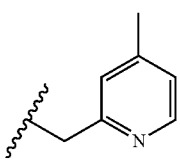 [SMILES: *Cc1cc(C)ccn1]
| Example | A | R | MW | MS (MH)+ | Human β3 agonist functional activity |
|---|---|---|---|---|---|
| 19 | CH | 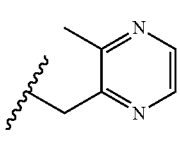 [SMILES: *Cc1nccnc1C] | 415.5 | 416.2 | +++ |
| 20 | CH | 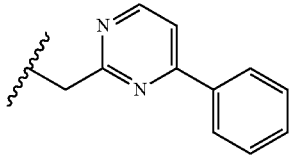 [SMILES: *Cc1nccc(-c2ccccc2)n1] | 416.5 | 417.2 | +++ |
| 21 | CH | 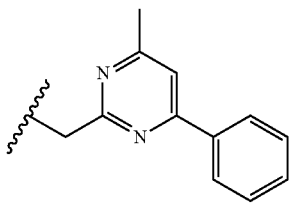 [SMILES: *Cc1nc(C)cc(-c2ccccc2)n1] | 478.6 | 479.3 | +++ |
| 22 | CH | 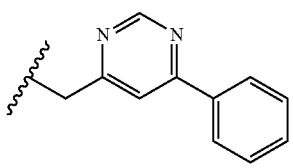 [SMILES: *Cc1cc(-c2ccccc2)ncn1] | 492.6 | 493.3 | +++ |
| 23 | CH | 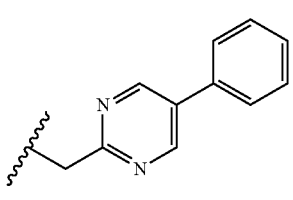 [SMILES: *Cc1ncc(-c2ccccc2)cn1] | 478.6 | 479.3 | +++ |
| 24 | CH | 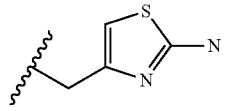 [SMILES: *Cc1csc(N)n1] | 478.6 | 479.2 | +++ |
| 25 | CH | 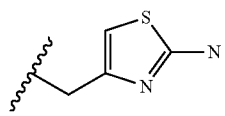 [SMILES: *Cc1csc(N)n1] | 422.5 | 423.2 | +++ |
| 26 | N | 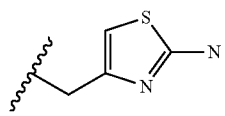 [SMILES: *Cc1csc(N)n1] | 423.5 | 424.2 | +++ |

TABLE 1-continued
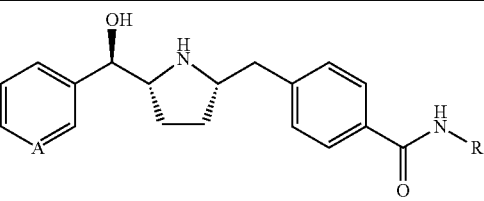
| Example | A | R | MW | MS (MH)+ | Human β3 agonist functional activity |
|---|---|---|---|---|---|
| 27 | CH | 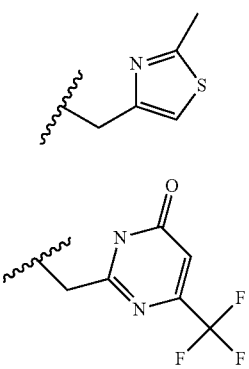 | 421.6 | 422.2 | +++ |
| 28 | CH | 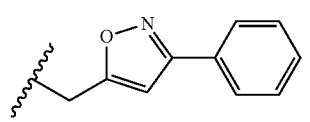 [SMILES: *Cc1cc(-c2ccccc2)no1] | 486.5 | 487.0 | +++ |
| 29 | CH | 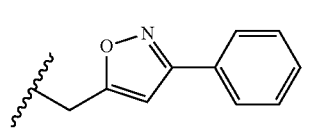 [SMILES: *Cc1cc(-c2ccccc2)no1] | 467.6 | 468.3 | +++ |
| 30 | N | 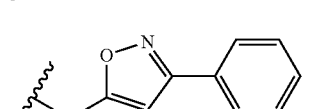 | 468.6 | 469.4 | +++ |
| 31 | NO (N oxide) | 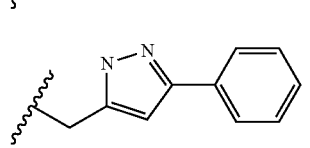 | 484.6 | 485.2 | ++++ |
| 32 | CH | 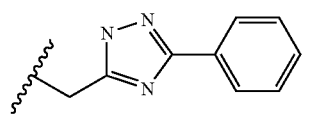 | 466.6 | 467.3 | +++ |
| 33 | N | 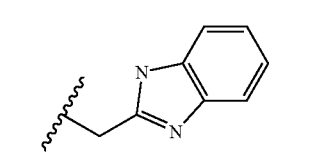 [SMILES: *Cc1nc2ccccc2[nH]1] | 468.6 | 469.4 | ++ |
| 34 | CH | 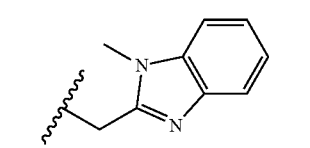 [SMILES: *Cc1nc2ccccc2n1C] | 440.6 | 441.3 | +++ |
| 35 | CH | | 454.6 | 455.3 | +++ |

TABLE 1-continued
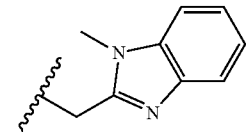 [SMILES: *Cc1nc2ccccc2n1C]
| Example | A | R | MW | MS (MH)+ | Human β3 agonist functional activity |
|---|---|---|---|---|---|
| 36 | N | 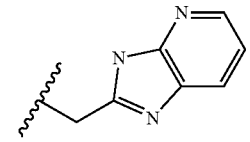 [SMILES: *Cc1nc2cccnc2[nH]1] | 455.6 | 456.2 | +++ |
| 37 | CH | 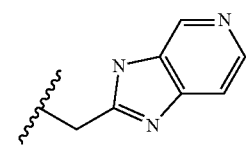 [SMILES: *Cc1nc2ccncc2[nH]1] | 441.5 | 442.3 | +++ |
| 38 | CH | 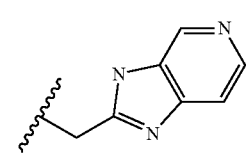 [SMILES: *Cc1nc2ccncc2[nH]1] | 441.5 | 442.3 | ++ |
| 39 | N | 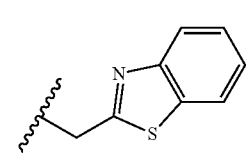 [SMILES: *Cc1nc2ccccc2s1] | 442.5 | 443.1 | +++ |
| 40 | CH | 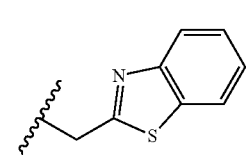 [SMILES: *Cc1nc2ccccc2s1] | 457.6 | 458.1 | +++ |
| 41 | N | 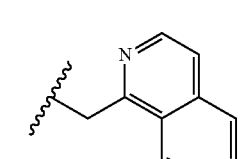 | 458.6 | 459.2 | +++ |
| 42 | CH | 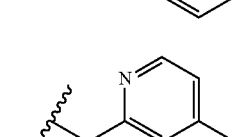 | 451.6 | 452.2 | ++ |
| 43 | N | | 452.6 | 453.2 | +++ |

TABLE 1-continued

| Example | A | R | MW | MS (MH)+ | Human β3 agonist functional activity |
|---|---|---|---|---|---|
| 44 | CH | quinolin-2-ylmethyl | 451.6 | 452.2 | +++ |
| 45 | CH | isoquinolin-3-ylmethyl | 451.6 | 452.2 | +++ |
| 46 | CH | 2-(1H-imidazol-4-yl)benzyl | 466.6 | 467.2 | ++++ |
| 47 | CH | 5,6-dihydro-4H-cyclopenta[d]thiazol-5-yl | 433.6 | 434.0 | ++++ |
| 48 | CH | 5,6,7,8-tetrahydroquinolin-8-yl | 441.6 | 442.2 | ++++ |
| 49 | N | 1-methyl-2-oxopyrrolidin-3-yl | 408.5 | 409.1 | ++++ |

TABLE 2

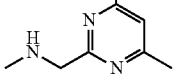

| Example | R[1] | R[2] | R[3] | R | MW | MS (MH)+ | Human β3 agonist functional activity |
|---|---|---|---|---|---|---|---|
| 50 | F | H | H | | 448.5 | 449.04 | +++ |

The following amide coupling and de-coupling procedures are applicable to Examples 51-137.

General Amide Coupling Procedure:

To either 4-({(2S,5R)-1-(tert-butoxycarbonyl)-5-[(R)-hydroxy(phenyl)methyl]pyrrolidine-2-yl}methyl)benzoic acid or 4-({(2S,5R)-1-(tert-butoxycarbonyl)-5-[(R)-{[tert-butyl(dimethyl)silyl]oxy}{6-[(2-phenylpropan-2-yl)amino]pyridin-3-yl}methyl]pyrrolidin-2-yl}methyl)benzoic acid, or 4-({(2S,5R)-1-(tert-butoxycarbonyl)-5-[(R)-{[tert-butyl(dimethyl)silyl]oxy}(phenylmethyl]pyrrolidine-2-yl}methyl)benzoic acid (1 equivalent) in DMF at 25° C., was sequentially added HATU (1.2 equivalent), the amine (1.0-3.5 equivalents), and either triethylamine (3 equivalents) or DIPEA (5 equivalents). The reaction was stirred at room temperature until the reaction was determined to be complete by LC-MS.

Once the reaction was complete, the reaction was worked up in one of three ways prior to the deprotection step:

a) The reaction was quenched by pouring into a separatory funnel containing water and was extracted with ethyl acetate (3×50 mL). The organic extracts were combined and dried with either MgSO₄ or Na₂SO₄, filtered, and evaporated in vacuo and used directly in the subsequent deprotected step.

b) The reaction was quenched by pouring into a separatory funnel containing water and was extracted with ethyl acetate (3×50 mL). The organic extracts were combined and dried with either MgSO₄ or Na₂SO₄, filtered, evaporated in vacuo and then purified by chromatography using a Biotage normal phase purification system and a Biotage Snap silica column. The product was collected and concentrated in vacuo to afford the desired product that was used directly in the deprotection step.

c) The reaction was concentrated in vacuo and used directly in the subsequent deprotection step.

General Deprotection Procedure:

Deprotection of either the mono protected amide derived from 4-({(2S,5R)-1-(tert-butoxycarbonyl)-5-[(R)-hydroxy(phenyl)methyl]pyrrolidine-2-yl}methyl)benzoic acid, or the doubly protected amide derived from 4-({(2S,5R)-1-(tert-butoxycarbonyl)-5-[(R)-{[tert-butyl(dimethyl)silyl]oxy}(phenylmethyl]pyrrolidine-2-yl}methyl)benzoic acid, or 4-({(2S,5R)-1-(tert-butoxycarbonyl)-5-[(R)-{[tert-butyl(dimethyl)silyl]oxy}{6-[(2-phenylpropan-2-yl)amino]pyridin-3-yl}methyl]pyrrolidin-2-yl}methyl)benzoic acid was achieved by dissolving the amide (1 equivalent) in a 3:3:1 trifluoroacetic acid:acetonitrile:water solution at room temperature (ensuring that at least 50 equivalents of TFA are used). Alternatively, for amides derived from the mono protected 4-({(2S,5R)-1-(tert-butoxycarbonyl)-5-[(R)-hydroxy(phenyl)methyl]pyrrolidine-2-yl}methyl)benzoic acid, deprotection was achieved by dissolution of the amide in dichloromethane at room temperature and adding trifluoroacetic acid (260 equivalents). Once the deprotection was determined to be complete by LC-MS, the reaction was concentrated in vacuo and directly purified by reverse phase Gilson HPLC (Waters Sunfire C18 ODB™, 5 μM, 19×100 mm column; typically 10-80% 0.1% trifluoroacetic acid in acetonitrile/0.1% trifluoroacetic acid in water gradient). The resulting pure fractions were lyophilized to give the titled compound.

EXAMPLE 51

4-({(2S,5R)-5-[(R)-hydroxy(phenyl)methyl]pyrrolidin-2-yl}methyl)-N-methyl-N-(pyridine-3-ylmethyl)benzamide

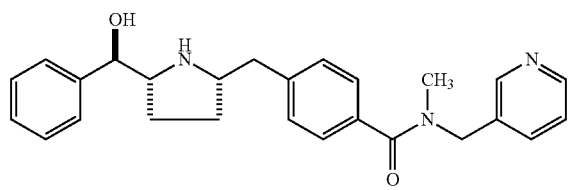 [SMILES: CN(Cc1cccnc1)C(=O)c1ccc(C[C@@H]2CC[C@H]([C@H](O)c3ccccc3)N2)cc1]

Step A: Tert-butyl (2R,5S)-2-[(R)-{[tert-butyl(dimethyl)silyl]oxy}(phenylmethyl]-5-[4-[methyl(pyridine-3-ylmethyl)carbamoyl]benzyl}pyrrolidine-1-carboxylate

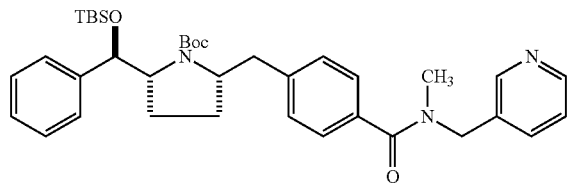 [SMILES: CN(Cc1cccnc1)C(=O)c1ccc(C[C@@H]2CC[C@H]([C@H](O[Si](C)(C)C(C)(C)C)c3ccccc3)N2C(=O)OC(C)(C)C)cc1]

To a solution of 4-({(2S,5R)-1-(tert-butoxycarbonyl)-5-[(R)-{[tert-butyl(dimethyl)silyl]oxy}(phenylmethyl]pyrrolidine-2-yl}methyl)benzoic acid (0.080 g, 0.15 mmol) in DMF (0.76 mL) at 25° C., was sequentially added HATU (0.069 g, 0.18 mmol, 1.2 equivalents), N-methyl-1-(pyridin-3-yl)methanamine (0.028 g, 0.23 mmol, 1.5 equivalents), and DIPEA (133 μL, 0.76 mmol, 5 equivalents). The reaction was stirred to room temperature overnight, at which point it was determined to be complete by LC-MS. The reaction was quenched by pouring into a separatory funnel containing water and was extracted with ethyl acetate (3×50 mL). The organic extracts were combined and dried with either MgSO₄, filtered, evapourated in vacuo and then purified by chromatography using a Biotage normal phase purification system and a Biotage Snap silica column eluting with 0-50% ethyl acetate in hexanes. The product fractions were collected and concentrated in vacuo to afford the desired product (0.095 g, 99%). LC-MS 630.2 (M+1)⁺.

Step B: 4-({(2S,5R)-5-[(R)-hydroxy(phenyl)methyl]pyrrolidin-2-yl}methyl)-N-methyl-N-(pyridine-3-ylmethyl)benzamide

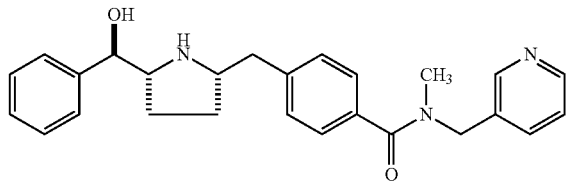 [SMILES: CN(Cc1cccnc1)C(=O)c1ccc(C[C@@H]2CC[C@H]([C@H](O)c3ccccc3)N2)cc1]

The intermediate compound from Step A (0.095 g, 0.15 mmol) was dissolved in an 3:1 acetonitrile:water solution (1.43 mL) at room temperature and trifluoroacetic acid (1.16 mL, 15.1 mmol, 100 equivalents) was added. The light brown solution was stirred at ambient temperature overnight, at which point LC-MS indicated complete deprotection of the starting material. The reaction mixture was concentrated in vacuo and the residue was purified by reverse phase Gilson HPLC (Waters Sunfire C18 ODB™, 5 μM, 19×100 mm column; 10-50% 0.1% trifluoroacetic acid in acetonitrile/0.1% trifluoroacetic acid in water gradient). The resulting pure fractions were lyophilized to give the titled compound as the trifluoroacetic acid salt (0.057 g, 71%). ¹H NMR (CDCl₃): 1.64-2.01 (m, 4H), 2.78-3.04 (m, 4H), 3.23 (s, 1H), 3.78 (m, 2H), 4.46-4.76 (m, 3H), 6.20 (bs, 1H), 7.10-7.37 (m, 13H), 9.08 (bs, 1H), 9.50 (bs, 1H). LC-MS 416.2 (M+1)⁺.

Using the Beta-3 agonist in vitro functional assay described above the human Beta-3 agonist functional activity of Example 51 was determined to be between 1 to 9.9 nM.

EXAMPLES 52-132

Using procedures similar to those described in Example 51, Examples 52-132 shown in Table 3 were prepared from the appropriate starting materials.

Using the Beta-3 agonist in vitro functional assay described above the human beta-3 agonist functional activity of each compound was determined and shown in Tables 3 as the following ranges:
less than 1 nM (+);
1-9.9 nM (++);
10-99.9 nM (+++);
100-999 nM (++++);
1000-3000 nM (+++++).

TABLE 3

| Example | A | B | R | MW | MS (MH)⁺ | Human β3 agonist functional activity |
|---|---|---|---|---|---|---|
| 52 | CH | H | N(CH₃)-CH₂-isoquinolin-3-yl | 465.6 | 466.2 | ++++ |
| 53 | CH | H | N(CH₃)-CH₂CH₂-pyridin-3-yl | 429.6 | 430.2 | +++ |
| 54 | CH | H | N(CH₃)-CH₂-pyridin-2-yl | 415.5 | 416.2 | ++++ |
| 55 | CH | H | N(CH₃)-CH₂-pyridazin-3-yl | 416.5 | 417.2 | ++++ |

TABLE 3-continued
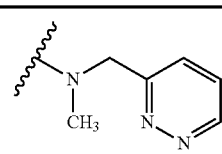
| Example | A | B | R | MW | MS (MH)+ | Human β3 agonist functional activity |
|---------|-----|-----|---|------|------|------|
| 56 | N | NH₂ | 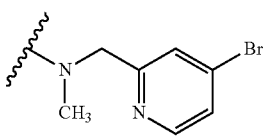 [SMILES: *N(C)Cc1cc(Br)ccn1] | 432.5 | 433.2 | +++ |
| 57 | CH | H | 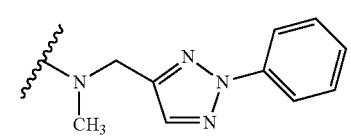 | 494.4 | 496.1 | +++ |
| 58 | CH | H | 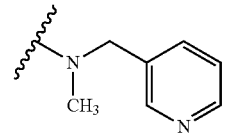 [SMILES: *N(C)Cc1cccnc1] | 481.6 | 482.2 | +++ |
| 59 | N | NH₂ | 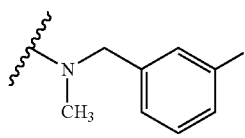 | 431.5 | 432.2 | + |
| 60 | CH | H | 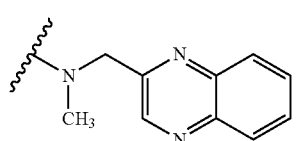 | 432.5 | 433.3 | ++ |
| 61 | CH | H | 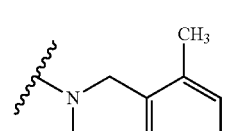 | 466.6 | 467.1 | ++ |
| 62 | CH | H | 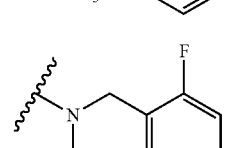 | 429.6 | 430.1 | +++ |
| 63 | CH | H | 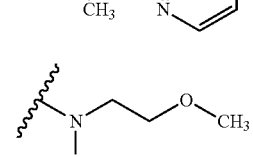 | 433.5 | 434.2 | +++ |
| 64 | CH | H |  | 382.5 | 383.1 | +++ |

TABLE 3-continued

| Example | A | B | R | MW | MS (MH)+ | Human β3 agonist functional activity |
|---------|----|---|---|------|-------|------|
| 65 | CH | H | N(CH3)CH2-(2-OCH3-C6H4) | 444.6 | 445.1 | +++ |
| 66 | CH | H | N(CH3)CH2-(2-methylthiazol-4-yl) | 435.6 | 436.1 | +++ |
| 67 | CH | H | N(CH3)CH2-(6-methylpyridin-2-yl) | 429.6 | 430.1 | +++ |
| 68 | CH | H | N(CH3)CH2-C6H5 | 414.5 | 415.2 | ++++ |
| 69 | CH | H | N(CH3)2 | 338.4 | 339.1 | +++ |
| 70 | CH | H | N(CH3)CH2-(1-methylbenzimidazol-2-yl) | 468.6 | 469.2 | ++++ |
| 71 | CH | H | N(CH3)CH2-(pyridin-4-yl) | 415.5 | 416.1 | ++++ |
| 72 | CH | H | N(CH3)CH2-(2-methyltetrazol-5-yl) | 420.5 | 421.2 | +++ |

TABLE 3-continued
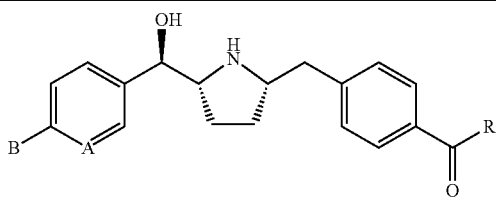
| Example | A | B | R | MW | MS (MH)+ | Human β3 agonist functional activity |
|---|---|---|---|---|---|---|
| 73 | CH | H | 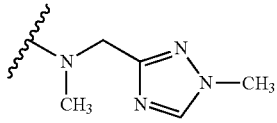 [SMILES: *N(C)Cc1ncn(C)n1] | 419.5 | 420.0 | ++++ |
| 74 | CH | H | 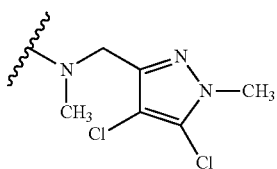 [SMILES: *N(C)Cc1nn(C)c(Cl)c1Cl] | 416.5 | 417.1 | +++ |
| 75 | CH | H | 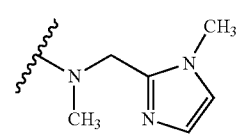 [SMILES: *N(C)Cc1nccn1C] | 487.4 | 487.1 | ++ |
| 76 | CH | H | 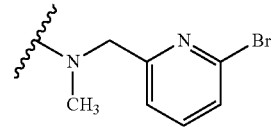 [SMILES: *N(C)Cc1cccc(Br)n1] | 418.5 | 419.1 | ++++ |
| 77 | CH | H | 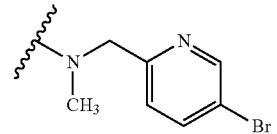 [SMILES: *N(C)Cc1ccc(Br)cn1] | 494.4 | 496.0 | +++ |
| 78 | CH | H | 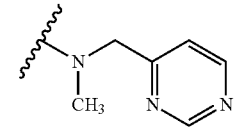 [SMILES: *N(C)Cc1ccncn1] | 494.4 | 496.0 | +++ |
| 79 | CH | H | 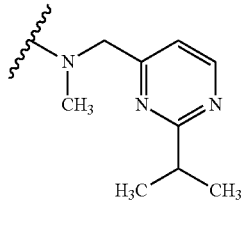 [SMILES: *N(C)Cc1ccnc(C(C)C)n1] | 416.5 | 417.1 | ++++ |
| 80 | CH | H | | 458.6 | 459.2 | ++ |

TABLE 3-continued

| Example | A | B | R | MW | MS (MH)+ | Human β3 agonist functional activity |
|---------|---|---|---|-----|----------|--------------------------------------|
| 81 | CH | H | N-methyl-(2-methylpyrimidin-4-yl)methyl | 430.5 | 431.1 | +++ |
| 82 | CH | H | N-methyl-(3-methylisoxazol-5-yl)methyl | 419.5 | 420.1 | +++ |
| 83 | CH | H | N-methyl-(6-pyrrolidin-1-yl-pyridin-2-yl)methyl | 484.6 | 485.2 | ++++ |
| 84 | CH | H | N-methyl-(1H-benzimidazol-2-yl)methyl | 454.6 | 455.1 | ++++ |
| 85 | CH | H | N-methyl-(4,5,6,7-tetrahydro-1H-indazol-3-yl)methyl | 458.6 | 459.2 | + |
| 86 | CH | H | N-methyl-(isoxazol-3-yl)methyl | 405.5 | 406.1 | +++ |
| 87 | CH | H | N-(2-fluorobenzyl)-N-(2-hydroxyethyl) | 462.5 | 463 | ++ |

TABLE 3-continued
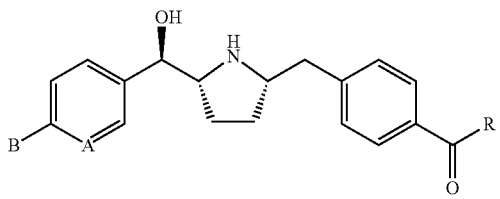
| Example | A | B | R | MW | MS (MH)+ | Human β3 agonist functional activity |
|---|---|---|---|---|---|---|
| 88 | CH | H | 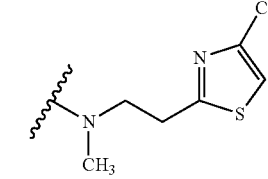 | 449.6 | 450 | +++ |
| 89 | CH | H | 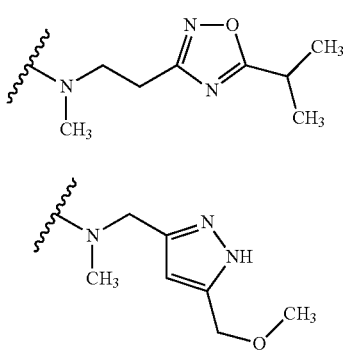 | 462.6 | 463 | +++ |
| 90 | CH | H | 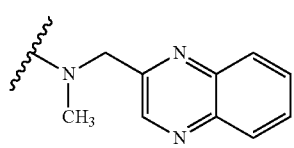 [SMILES: *N(C)Cc1cnc2ccccc2n1] | 448.5 | 449 | + |
| 91 | CH | H | 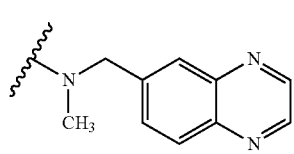 [SMILES: *N(C)Cc1ccc2nccnc2c1] | 466.6 | 467 | ++ |
| 92 | CH | H | 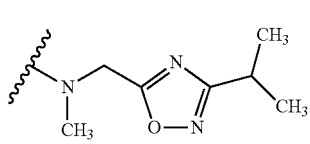 | 466.6 | 467 | +++ |
| 93 | CH | H | 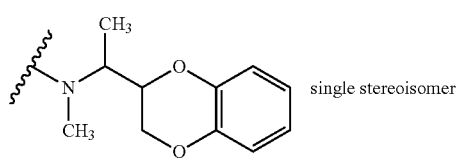 | 448.5 | 449 | +++ |
| 94 | CH | H | 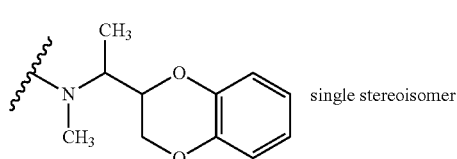 single stereoisomer | 486.6 | 487 | +++ |
| 95 | CH | H | single stereoisomer | 486.6 | 487 | ++++ |

TABLE 3-continued
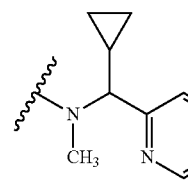
| Example | A | B | R | MW | MS (MH)+ | Human β3 agonist functional activity |
|---|---|---|---|---|---|---|
| 96 | CH | H | 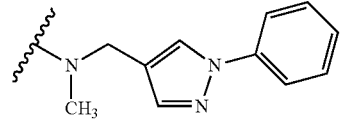 [SMILES: *N(C)Cc1cnn(-c2ccccc2)c1] | 455.6 | 456 | ++++ |
| 97 | CH | H | 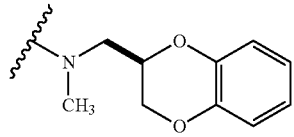 [SMILES: *N(C)C[C@@H]1COc2ccccc2O1] | 480.6 | 481 | +++ |
| 98 | CH | H | 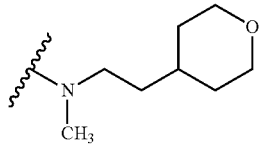 | 472.6 | 473 | ++ |
| 99 | CH | H | 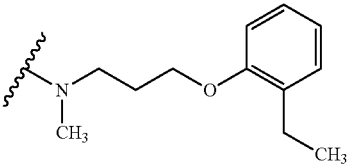 [SMILES: *N(C)CCCOc1ccccc1CC] | 436.6 | 437 | ++++ |
| 100 | CH | H | 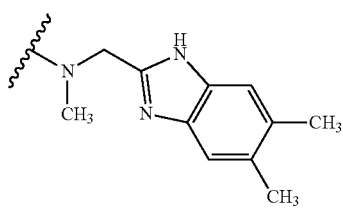 [SMILES: *N(C)Cc1nc2cc(C)c(C)cc2[nH]1] | 486.6 | 487 | ++++ |
| 101 | CH | H | 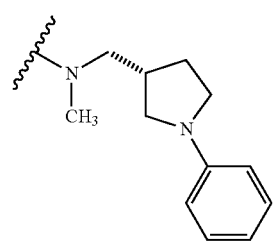 [SMILES: *N(C)C[C@@H]1CCN(c2ccccc2)C1] | 482.6 | 483 | ++++ |
| 102 | CH | H |  | 483.6 | 484 | ++++ |

TABLE 3-continued

| Example | A | B | R | MW | MS (MH)+ | Human β3 agonist functional activity |
|---|---|---|---|---|---|---|
| 103 | CH | H | (N-methyl-N-((3-(pyridin-4-yl)-1,2,4-oxadiazol-5-yl)methyl)amino) | 483.5 | 484 | ++++ |
| 104 | CH | H | (N-ethyl-N-((2-isopropylpyrimidin-4-yl)methyl)amino) | 472.6 | 473 | +++ |
| 105 | CH | H | (N-ethyl-N-(isochroman-1-ylmethyl)amino) | 484.6 | 485 | +++ |
| 106 | CH | H | (N-methyl-N-((3-fluoropyridin-2-yl)methyl)amino) | 433.5 | 434 | +++ |
| 107 | CH | H | (N-methyl-N-((5-(pyridin-4-yl)isoxazol-3-yl)methyl)amino) | 482.6 | 482 | ++++ |
| 108 | CH | H | (N-methyl-N-(thiazol-4-ylmethyl)amino) | 421.5 | 422 | ++++ |

TABLE 3-continued
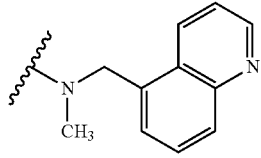 [SMILES: *N(C)Cc1cccc2ncccc12]
| Example | A | B | R | MW | MS (MH)+ | Human β3 agonist functional activity |
|---|---|---|---|---|---|---|
| 109 | CH | H | 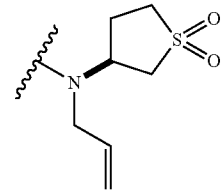 [SMILES: *N(CC=C)[C@H]1CCS(=O)(=O)C1] | 465.6 | 466 | ++++ |
| 110 | CH | H | 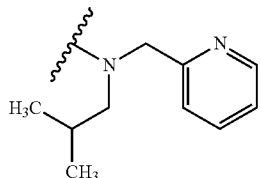 | 468.6 | 469 | +++ |
| 111 | CH | H | 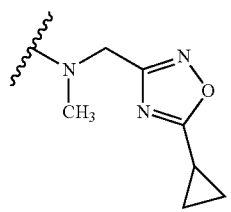 [SMILES: *N(C)Cc1noc(C2CC2)n1] | 457.6 | 458 | +++ |
| 112 | CH | H | 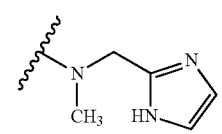 [SMILES: *N(C)Cc1ncc[nH]1] | 446.5 | 447.2 | +++ |
| 113 | CH | H | 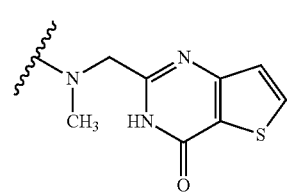 [SMILES: *N(C)Cc1nc2ccsc2c(=O)[nH]1] | 404.5 | 405 | +++ |
| 114 | CH | H | 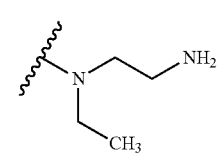 | 488.6 | 489 | ++ |
| 115 | CH | H |  | 381.5 | 382 | ++++ |

TABLE 3-continued

[Structure: 4-B-substituted phenyl-CH(OH)-pyrrolidine(NH)-CH2-phenyl-C(=O)-R, with stereochemistry shown; phenyl ring positions labeled A and B]

| Example | A | B | R | MW | MS (MH)+ | Human β3 agonist functional activity |
|---------|---|---|---|------|----------|--------------------------------------|
| 116 | CH | H | -N(CH2CH(CH3)2)-CH2-(5-methylthiazol-2-yl) | 477.6 | 478 | +++ |
| 117 | CH | H | -N(CH3)-(tetrahydrofuran-3-yl) | 394.5 | 395.2 | ++++ |
| 118 | CH | H | -N(CH3)-CH2-(thiazol-2-yl) | 421.6 | 422.1 | ++++ |
| 119 | CH | H | -N(CH3)-CH2CH2-(tetrahydropyran-2-yl) | 436.6 | 437.2 | ++++ |
| 120 | CH | H | -N(CH3)-CH2CH2-O-(4-methylphenyl) | 458.6 | 459.2 | +++++ |
| 121 | CH | H | -N(CH2CH3)-CH2-(pyridin-2-yl) | 429.6 | 430.2 | ++++ |
| 122 | CH | H | -N(CH3)-CH2-(thiazol-4-yl) | 421.6 | 422.1 | ++++ |
| 123 | CH | H | -N(CH3)-CH2-(4-methylthiazol-2-yl) | 435.6 | 436.1 | ++++ |

TABLE 3-continued

| Example | A | B | R | MW | MS (MH)+ | Human β3 agonist functional activity |
|---|---|---|---|---|---|---|
| 124 | CH | H | N-methyl-N-((2-chloropyridin-3-yl)methyl)amino | 450.0 | 450.1 | +++ |
| 125 | CH | H | N-methyl-N-((5-chloropyrimidin-2-yl)methyl)amino | 451.0 | 451.1 | ++++ |
| 126 | CH | H | N-methyl-N-((8-methylimidazo[1,2-a]pyridin-2-yl)methyl)amino | 468.6 | 469.2 | ++++ |
| 127 | CH | H | N-methyl-N-((tetrahydrofuran-2-yl)methyl)amino | 408.5 | 409.2 | ++++ |
| 128 | CH | H | N-methyl-N-(1-(pyridin-3-yl)ethyl)amino | 429.6 | 430.2 | ++ |
| 129 | CH | H | N-ethyl-N-(pyridazin-3-ylmethyl)amino | 430.5 | 431.3 | ++++ |
| 130 | CH | H | N-cyclopropyl-N-(pyridazin-3-ylmethyl)amino | 442.6 | 443.3 | ++++ |

TABLE 3-continued

| Example | A | B | R | MW | MS (MH)+ | Human β3 agonist functional activity |
|---------|----|----|---|------|-------|-------|
| 131 | CH | H | | 474.6 | 475.2 | ++++ |
| 132 | CH | H | | 436.6 | 437.1 | ++++ |

EXAMPLE 133

4-({(2S,5R)-5-[(6-aminopyridin-3-yl)(hydroxy)methyl]pyrrolidin-2-yl}methyl)-N,N-dimethylbenzamide

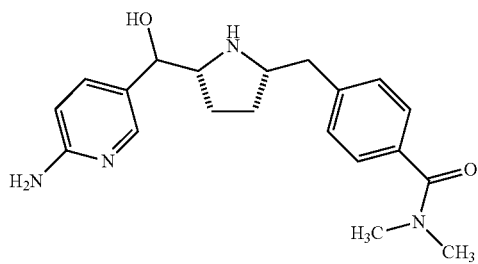

Step A: Tert-butyl (2R,5S)-2-[(R)[6-(tert-butylamino)pyridin-3-yl]{[tert-butyl(dimethyl)silyl]oxy}methyl]-5-[4-(methoxycarbonyl)benzyl]pyrrolidine-1-carboxylate

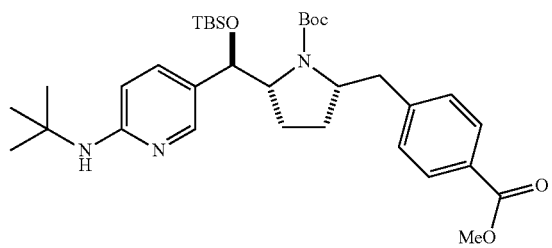

A solution of tert-butyl (2R,5S)-2-[(R)-{[tert-butyl(dimethyl)silyl]oxy}(1-oxidopyridin-3-yl)methyl]-5-[4-(methoxycarbonyl)benzyl]pyrrolidine-1-carboxylate (0.049 g, 0.087 mmol) in trifluorotoluene (2 mL) was cooled to 0° C. Tert-butylamine (0.046 mL, 0.44 mmol) was added, followed by p-toluenesulfonic anhydride (0.057 g, 0.18 mmol). After 1 hour, the reaction was diluted with EtOAc (50 mL) and washed with water (15 mL) and brine (15 mL). The organic layer was dried over $Na_2SO_4$, filtered, and concentrated in vacuo. The residue was purified by silica gel chromatography with 0-45% EtOAc/hexanes to afford 47 mg of impure tert-butyl (2R,5S)-2-[(R)-[6-(tert-butylamino)pyridin-3-yl]{[tert-butyl(dimethyl)silyl]oxy}methyl]-5-[4-(methoxycarbonyl)benzyl]pyrrolidine-1-carboxylate. LC-MS=6123 $(M-H)^+$.

Step B: Tert-butyl (2R,5S)-2-[(R)-[6-(tert-butylamino)pyridin-3-yl(hydroxy)methyl]-5-[4-(methoxycarbonyl)benzyl]pyrrolidine-1-carboxylate

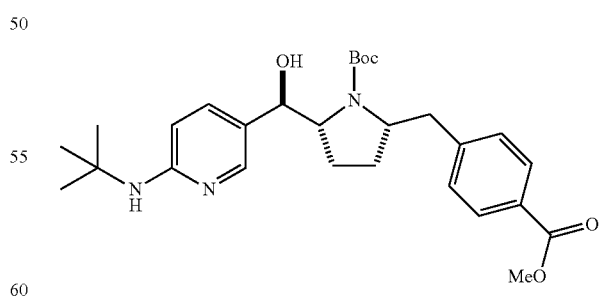

To a solution of impure tert-butyl (2R,5S)-2-[(R)-[6-(tert-butylamino)pyridin-3-yl]{[tert-butyl(dimethyl)silyl]oxy}methyl]-5-[4-(methoxycarbonyl)benzyl]pyrrolidine-1-carboxylate (0.047 g, 0.077 mmol) in THF (2 mL) was added TBAF (1M solution in THF, 0.38 mL, 0.38 mmol). The reaction was stirred at room temperature for 24 hours and then quenched with saturated aqueous NH₄Cl. The mixture was diluted with EtOAc (50 mL), and washed with water (15 mL) and brine (15 mL). The organic layer was dried over Na₂SO₄, filtered, and concentrated. The residue was purified by silica gel chromatography with 20-75% EtOAc/hexanes to afford tert-butyl (2R,5S)-2-[(R)-[6-(tert-butylamino)pyridin-3-yl(hydroxy)methyl]-5-[4-(methoxycarbonyl)benzyl]pyrrolidine-1-carboxylate (21.8 mg, 57%). ¹H NMR (600 MHz, CD₃OD) δ 1.38 (s, 9H), 1.42-2.06 (m, 14H), 3.10 & 2.87 (2 singlets, 1H), 3.85 (s, 3H), 3.84-4.14 (m, 2H), 4.79-4.92 (m, 1H), 6.58 (d, J=7.9 Hz, 1H), 7.16 (bs, 2H), 7.42 (dd, J=8.8, 2.4 Hz, 1H), 7.80-7.90 (m, 3H). LC-MS=498.2 (M+1)⁺.

Step C: 4-({(2S,5R)-1-(tert-butoxycarbonyl)-5-[(R)-6-(tert-butylamino)pyridin-3-yl](hydroxy)methyl]pyrrolidin-2-yl}methyl)benzoic Acid

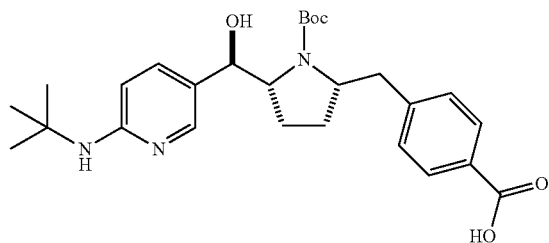

To a solution of tert-butyl (2R,5S)-2-[(R)-[6-(tert-butylamino)pyridin-3-yl(hydroxy)methyl]-5-[4-(methoxycarbonyl)benzyl]pyrrolidine-1-carboxylate (0.017 g, 0.034 mmol) in dioxane (2 mL) and water (0.5 mL) was added 1M LiOH (0.205 mL, 0.205 mmol). The reaction was stirred vigorously at r.t. for 18 hours and then quenched with acetic acid (0.016 mL, 0.273 mmol). The reaction was diluted with EtOAc (40 mL) and washed with water (10 mL) and brine (10 mL). The organic layer was dried over Na₂SO₄, filtered, and concentrated. The residue was taken up in DCM/heptanes and concentrated in vacuo to afford 4-({(2S,5R)-1-(tert-butoxycarbonyl)-5-[(R)-[6-(tert-butylamino)pyridin-3-yl](hydroxy)methyl]pyrrolidin-2-yl}methyl)benzoic acid (16.5 mg, 100%). LC-MS=484.2 (M+1)⁺.

Step D: Tert-butyl (2R,5S)-2-[(R)-[6-(tert-butylamino)pyridin-3-yl(hydroxy)methyl]-5-[4-(dimethylcarbamoyl)benzyl]pyrrolidine-1-carboxylate

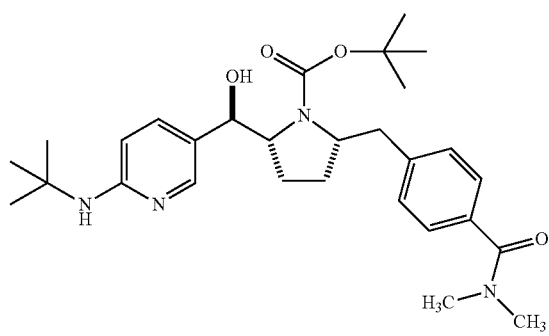

To a solution of 4-({(2S,5R)-1-(tert-butoxycarbonyl)-5-[(R)-[6-(tert-butylamino)pyridin-3-yl](hydroxy)methyl]pyrrolidin-2-yl}methyl)benzoic acid (0.0186 g, 0.038 mmol) in acetonitrile (1 mL), DIPEA (0.020 mL, 0.115 mmol) was added. HATU (14.62 mg, 0.038 mmol) was added, followed by dimethylamine (0.048 mL of a 2M solution in THF, 0.096 mmol). The reaction was stirred at room temperature for 2 hours and then diluted with EtOAc (40 mL) and washed with saturated NaHCO₃ (10 mL) and brine (10 mL). The organic layer was dried over Na₂SO₄, filtered, and concentrated. The residue was purified by silica gel chromatography with 0-100% EtOAc/hexanes to afford tert-butyl (2R,5S)-2-[(R)-[6-(tert-butylamino)pyridin-3-yl](hydroxy)methyl]-5-[4-(dimethylcarbamoyl)benzyl]pyrrolidine-1-carboxylate (18.3 mg, 93%). LC-MS=511.3 (M+1)⁺.

Step E: 4-({(2S,5R)-5-[(R)-[6-tert-butylamino)pyridin-3-yl](hydroxy)methyl]pyrrolidin-2-yl}methyl)-N,N-dimethylbenzamide

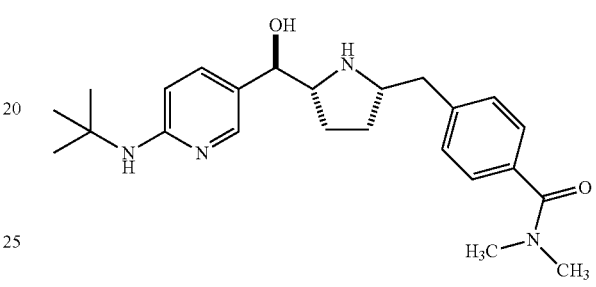

To a solution of tert-butyl (2R,5S)-2-[(R)-[6-(tert-butylamino)pyridin-3-yl(hydroxy)methyl]-5-[4-(dimethylcarbamoyl)benzyl]pyrrolidine-1-carboxylate (18.3 mg, 0.036 mmol) in acetonitrile (450 μL) and water (150 μl) was added TFA (450 μl, 5.84 mmol). The reaction was heated to 50° C. for 1 hour and then cooled to room temperature. The reaction was diluted with CH₃CN/water (1:1, 1 mL), and purified by reverse phase chromatography with 15 to 50% CH₃CN/water containing 0.1% TFA. Fractions containing the desired product were lyophilized to afford 4-({(2S,5R)-5-[(R)-[6-(tert-butylamino)pyridin-3-yl](hydroxy)methyl]pyrrolidin-2-yl}methyl)-N,N-dimethylbenzamide as a bis-TFA salt (19 mg, 83%). LC-MS=411.3 (M+1)⁺. ¹H NMR (600 MHz, CD₃OD) δ 1.48 (s, 9H), 1.80-2.14 (m, 4H), 2.98 (s, 3H), 3.04 (dd, J=13.8, 8.4 Hz, 1H), 3.08 (s, 3H), 3.18 (dd, J=13.8, 6.6 Hz, 1H), 3.79 (m, 2H), 4.75 (d, J=7.8 Hz, 1H), 7.18 (d, J=9.6 Hz, 1H), 7.36 (d, J=8.4 Hz, 2H), 7.91 (s, 1H), 7.94 (d, J=7.8 Hz, 2H), 7.95 (d, J=9.6 Hz, 1H).

Step F: 4-({(2S,5R)-5-[(6-aminopyridin-3-yl)(hydroxy)methyl]pyrrolidin-2-yl}methyl)-N,N-dimethylbenzamide

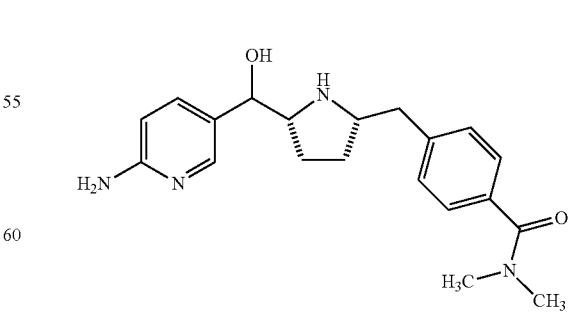

4-({(2S,5R)-5-[(R)-6-(tert-butylamino)pyridin-3-yl](hydroxy)methyl]pyrrolidin-2-yl}methyl)-N,N-dimethylbenzamide (11 mg, 0.027 mmol) was dissolved in TFA (600 μl, 7.79 mmol) and heated to 70° C. for 4 hours. The reaction was then cooled to r.t., diluted with CH₃CN/water (1:1, 1 mL), and purified by reverse phase chromatography with 15-50% CH₃CN/water containing 0.1% TFA. Fractions containing desired product were lyophilized to afford 4-({(2S,5R)-5-[(6-aminopyridin-3-yl)(hydroxy)methyl]pyrrolidin-2-yl}methyl)-N,N-dimethylbenzamide as a bis-TFA salt (8.9 mg, 57%). LC-MS=355.2 (M+1)⁺.

Using the Beta-3 agonist in vitro functional assay described above the human Beta-3 agonist functional activity of Example 133 was determined to be between 10 to 99.9 nM.

EXAMPLE 134

4-({(2S,5R)-5-[(R)-hydroxy(phenyl)methyl]pyrrolidin-2-yl}methyl)-N-methyl-N-[2-(pyridin-2-yl)ethyl)benzamide

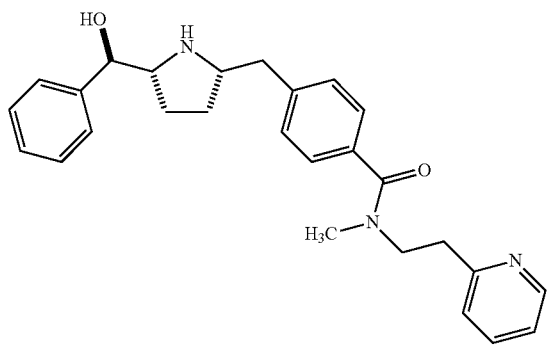

Step A: Tert-butyl (2R,5S)-2-[(R)-{[tert-butyl(dimethyl)silyl]oxy}(phenyl)methyl]-5-(4-{[2-(pyridine-2-yl)ethyl]carbamoyl}benzyl)pyrrolidine-1-carboxylate

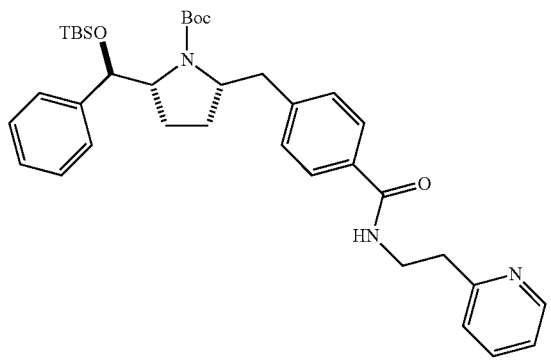

2-(2-Aminoethyl)pyridine (0.034 mL, 0.29 mmol) was added to a stirred, room temperature mixture of 4-({(2S,5R)-1-(tert-butoxycarbonyl)-5-[(R)-{[tert-butyl(dimethyl)silyl]oxy}(phenyl)methyl]pyrrolidin-2-yl}methyl)benzoic acid (100 mg, 0.190 mmol), HATU (87 mg, 0.228 mmol), and DIPEA (0.166 mL, 0.951 mmol) in DMF (1.9 ml). The resulting mixture was stirred at room temperature overnight. Upon completion, as determined by LC-MS, water was added, and the mixture was partitioned with EtOAc. The aqueous layer was extracted with EtOAc (3×), and the combined organic layers were washed with brine, dried with Na₂SO₄, filtered, and concentrated in vacuo to give the product that was used directly in the next step. LC-MS=630.3 (M+1)⁺.

Step B: Tert-butyl (2R,5S)-2-[(R)-{[tert-butyl(dimethyl)silyl]oxy}(phenyl)methyl]-5-(4-{methyl[2-(pyridine-2-yl)ethyl]carbamoyl}benzyl)pyrrolidine-1-carboxylate

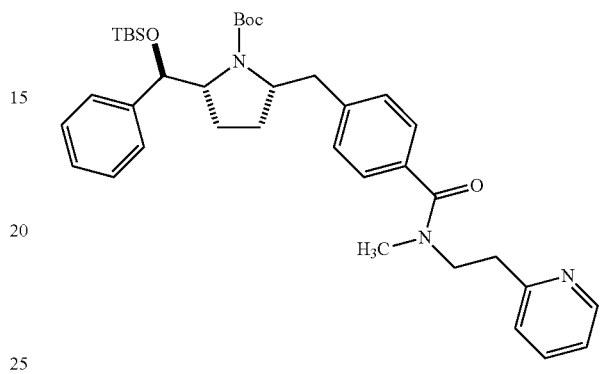

NaH (8.38 mg of a 60 wt % dispersion in mineral oil, 0.210 mmol) was added to a stirred, room temperature mixture of tert-butyl (2R,5S)-2-[(R)-{[tert-butyl(dimethyl)silyl]oxy}(phenyl)methyl]-5-(4-{[2-(pyridine-2-yl)ethyl]carbamoyl}benzyl)pyrrolidine-1-carboxylate (120 mg, 0.191 mmol) in tetrahydrofuran (1.9 mL), and the mixture was stirred for 30 minutes. After 30 minutes, iodomethane (0.014 mL, 0.23 mmol) was added and the mixture was stirred for 12 hours. Water was then added and the mixture was partitioned with EtOAc. The aqueous extracts were extracted with EtOAc (3×), and the combined organic layers were washed with brine, dried with Na₂SO₄, filtered, and concentrated in vacuo to give the product as an orange oil that was used directly in the next step. LC-MS=644.3 (M+1)⁺.

Step C: 4-({(2S,5R)-5-[(R)-hydroxy(phenyl)methyl]pyrrolidin-2-yl}methyl)-N-methyl-N-[2-(pyridin-2-yl)ethyl)benzamide

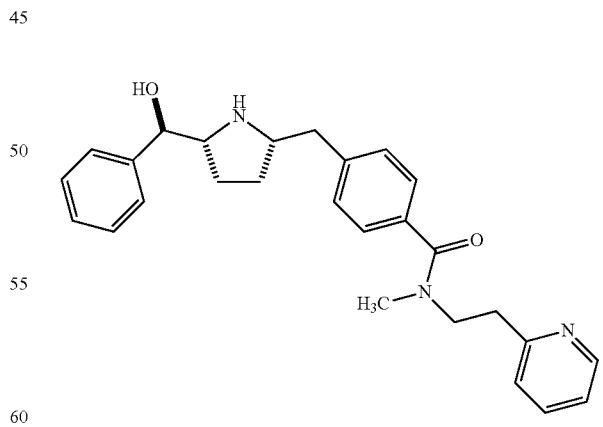

The crude tert-butyl (2R,5S)-2-[(R)-{[tert-butyl(dimethyl)silyl]oxy}(phenyl)methyl]-5-(4-{methyl[2-(pyridine-2-yl)ethyl]carbamoyl}benzyl)pyrrolidine-1-carboxylate was dissolved in a 3:3:1 mixture of acetonitrile (1.4 mL):TFA (1.4 mL):water (0.47 mL), and the mixture was heated to 55° C. and stirred for 1 hour. The mixture was then concentrated in vacuo and purified by mass directed reverse phase HPLC using acetonitrile/water with 0.1% NH$_4$OH buffer. Lyophilization of the desired fractions gave the title compound (21 mg, 26% yield over three steps) as a brown oil.

Using the Beta-3 agonist in vitro functional assay described above the human Beta-3 agonist functional activity of Example 134 was determined to be between 10 to 99.9 nM.

EXAMPLE 135

N-(2-fluorobenzyl)-4-({(2S,5R)-5-[(R)-hydroxy(phenyl)methyl]pyrrolidin-2-yl}methyl)-N-methylbenzamide

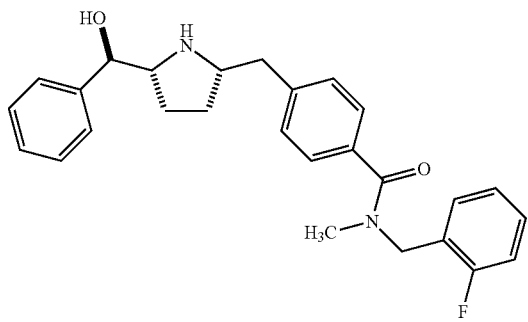

Step A: Tert-butyl (2R,5S)-2-[(R)-{[tert-butyl(dimethyl)silyl]oxy}(phenyl)methyl]-5-[4-(methylcarbamoyl)benzyl]pyrrolidine-1-carboxylate

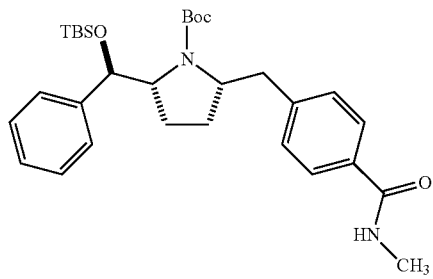

Methylamine (5.71 mL of a 2M THF solution, 11.4 mmol) was added to a stirred, room temperature solution of 4-({(2S,5R)-1-(tert-butoxycarbonyl)-5-[(R)-{[tert-butyl(dimethyl)silyl]oxy}(phenyl)methyl]pyrrolidin-2-yl}methyl)benzoic acid (2.00 g, 3.80 mmol), HATU (1.736 g, 4.56 mmol, 1.2 equivalents) and DIPEA (3.32 mL, 19.0 mmol, 5 equivalents) in DMF (7.8 mL). The reaction was stirred at room temperature for 12 hours, after which the mixture was diluted with EtOAc and partitioned with water. The aqueous layer was extracted with EtOAc (3×), and the combined organic layers were washed with brine, dried over MgSO$_4$, filtered, and concentrated in vacuo. The residue was purified by normal phase flash chromatography using silica gel (0-50% hexanes/ethyl acetate). The product fractions were collected and concentrated in vacuo to afford the title compound as a white solid (1.20 g, 59%). LC-MS=561.2 (M+Na)$^+$.

Step B: Tert-butyl (2R,5S)-2-[(R)-{[tert-butyl(dimethyl)silyl]oxy}(phenyl)methyl]-5-{4-[(2-fluorobenzyl)(methyl)carbamoyl]benzyl}pyrrolidine-1-carboxylate

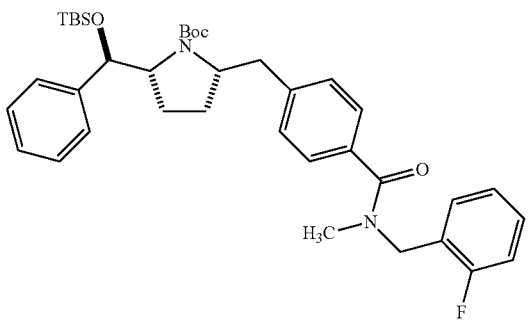

NaH (6.1 mg of a 60 wt % dispersion in mineral oil, 0.153 mmol, 1 equivalent) was added to a stirred, room temperature mixture tert-butyl (2R,5S)-2-[(R)-{[tert-butyl(dimethyl)silyl]oxy}(phenyl)methyl]-5-[4-(methylcarbamoyl)benzyl]pyrrolidine-1-carboxylate (80 mg, 0.148 mmol) in DMF (0.74 mL), and the mixture was stirred for 10 minutes. 1-(Bromomethyl)-2-fluorobenzene (0.0281 mg, 0.148 mmol, 1 equivalent) was added and the mixture was stirred overnight. Water was then added and the mixture was partitioned with EtOAc. The aqueous layer was extracted with EtOAc (3×), and the combined organic extracts were washed with brine, dried with Na$_2$SO$_4$, filtered, and concentrated in vacuo. The residue was purified by normal phase flash chromatography using silica gel (0-50% hexanes/ethyl acetate). The product was collected and concentrated in vacuo to afford the title compound (95 mg, 99%). LC-MS=669.2 (M+Na)$^+$.

Step C: N-(2-fluorobenzyl)-4-({(2S,5R)-5-[(R)-hydroxy(phenyl)methyl]pyrrolidin-2-yl}methyl)-N-methyl-N-methylbenzamide

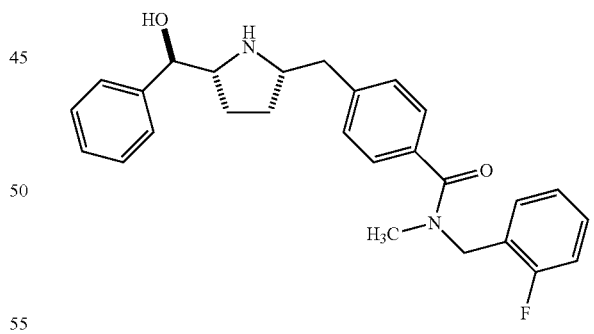

Tert-Butyl (2R,5S)-2-[(R)-{[tert-butyl(dimethyl)silyl]oxy}(phenyl)methyl]-5-{4-[(2-fluorobenzyl)(methyl)carbamoyl]benzyl}pyrrolidine-1-carboxylate (95 mg, 0.147 mmol) was dissolved in a 3:3:1 mixture of acetonitrile (1.1 mL):TFA (1.1 mL):water (0.37 mL), and the mixture was stirred at room temperature overnight. The mixture was then concentrated in vacuo and purified by reverse phase Gilson HPLC using acetonitrile/water with 0.1% TFA buffer. Lyophilization of the desired fractions gave the title compound as the TFA salt (60 mg, 75% yield over three steps). LC-MS=433.1 (M+H)$^+$.

Using the Beta-3 agonist in vitro functional assay described above the human Beta-3 agonist functional activity of Example 135 was determined to be between 10 to 99.9 nM.

EXAMPLE 136

N-[(6-aminopyridin-2-yl)methyl]-4-({(2S,5R)-5-[(R)-hydroxy(phenyl)methyl]pyrrolidin-2-yl}methyl)-N-methylbenzamide

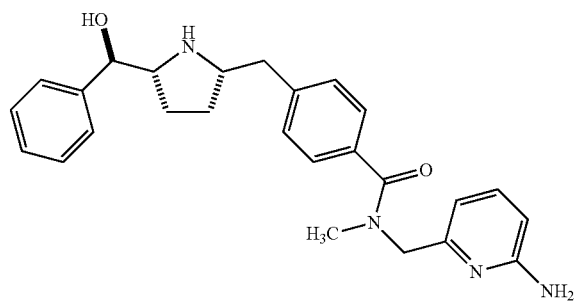

Step A: Tert-butyl (2R,5S)-2-(4-{[(6-bromopyridin-2-yl)methyl](methyl)carbamoyl}benzyl)-5-[(R)-{[tert-butyl(dimethyl)silyl]oxy}(phenyl)methyl]-pyrrolidine-1-carboxylate

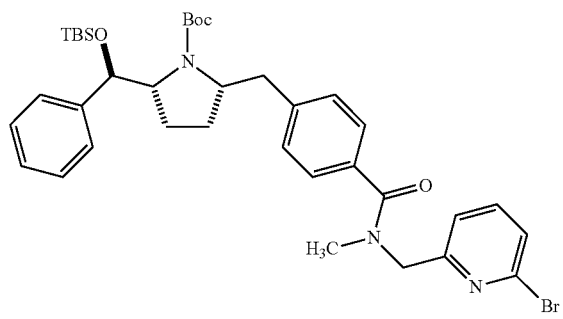

1-(6-Bromopyridin-2-yl)-N-methylmethanamine (115 mg, 0.571 mmol) was added to a stirred, room temperature mixture of 4-({(2S,5R)-1-(tert-butoxycarbonyl)-5-[(R)-{[tert-butyl(dimethyl)silyl]oxy}(phenyl)methyl]pyrrolidin-2-yl}methyl)benzoic acid (300 mg, 0.571 mmol), HATU (260 mg, 0.685 mmol, 1.2 equivalents) and DIPEA (498 μL, 2.85 mmol, 5 equivalents) in DMF (2.8 mL). The reaction was stirred at room temperature for 12 hours, and then diluted with EtOAc and partitioned with water. The aqueous layer was extracted with EtOAc (3×), and the combined organic extracts were washed with brine, dried over MgSO₄, filtered, and concentrated in vacuo. The residue was purified by normal phase flash chromatography using silica gel (0-50% hexanes/ethyl acetate). The product was collected and concentrated in vacuo to afford the title compound (110 mg, 27%). LC-MS=608.2 & 610.2 (M-Boc+H)$^+$.

Step B: Tert-butyl (2R,5S)-2-(4-{[(6-aminopyridin-2-yl)methyl](methyl)carbamoyl}benzyl)-5-[(R)-{[tert-butyl(dimethyl)silyl]oxy}(phenyl)methyl]-pyrrolidine-1-carboxylate

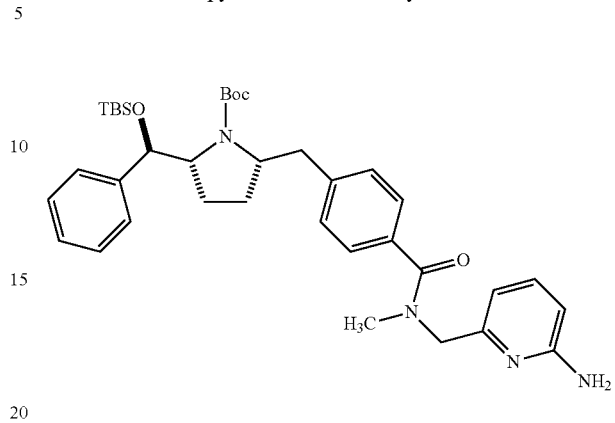

In a round bottom flask was added CuI (0.54 mg, 2.8 μmol, 0.1 equivalents), Cs₂CO₃ (18.3 mg, 0.056 mmol, 2 equivalents), and tert-butyl (2R,5S)-2-(4-{[(6-bromopyridin-2-yl)methyl](methyl)carbamoyl}benzyl)-5-[(R)-{[tert-butyl(dimethyl)silyl]oxy}(phenyl)methyl]-pyrrolidine-1-carboxylate (20 mg, 0.028 mmol). The flask was evacuated and backfilled with nitrogen (3×) and then 2,4-pentadione (1.69 mg, 0.017 mmol, 0.6 equivalents), DMF (141 μL) and ammonium hydroxide (19.6 μL, 0.141 mmol, 5 equivalents) was added. The contents were transferred to a sealed tube under positive nitrogen pressure. The reaction was stirred and heated at 90° C. for 16 hours. The reaction was cooled and filtered over celite and washed with EtOAc. The EtOAc was washed with water and the aqueous layer was extracted with EtOAc (3×). The organic extracts were then dried over Na₂SO₄, filtered, and concentrated in vacuo to afford the crude product (19 mg) that was taken directly onto the next step. LC-MS=646.3 (M+H)$^+$.

Step C: N-[(6-aminopyridin-2-yl)methyl]-4-({(2S,5R)-5-[(R)-hydroxy(phenyl)methyl]pyrrolidin-2-yl}methyl)-N-methylbenzamide

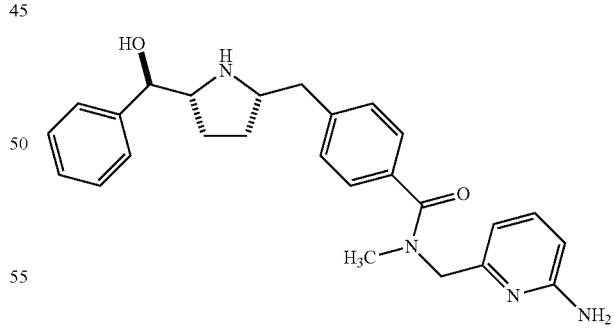

To the crude tert-butyl (2R,5S)-2-(4-{[(6-aminopyridin-2-yl)methyl](methyl)carbamoyl}benzyl)-5-[(R)-{[tert-butyl(dimethyl)silyl]oxy}(phenyl)methyl]-pyrrolidine-1-carboxylate (19 mg, 0.029 mmol) was dissolved in a 3:3:1 mixture of acetonitrile (0.22 mL):TFA (0.22 mL):water (0.07 mL), and the mixture was stirred at room temperature overnight. Upon completion, as observed by LC-MS, the mixture was concentrated in vacuo purified by reverse phase Gilson HPLC using acetonitrile/water with 0.1% TFA buffer. Lyophilization of the desired fractions gave the title compound as the TFA salt (6 mg, 31% yield over two steps), LC-MS=432.3 (M+H)+.

Using the Beta-3 agonist in vitro functional assay described above the human Beta-3 agonist functional activity of Example 136 was determined to below 1 nM.

EXAMPLE 137

4-({(2S,5R)-5-[(R)-hydroxy(phenyl)methyl]pyrrolidine-2-yl}methyl)-N-methyl-N-[1-pyridin-2-yl) ethyl]benzamide

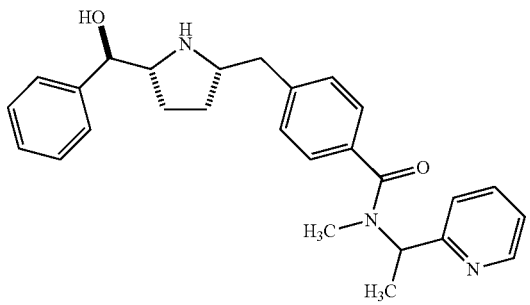

Step A: Tert-butyl (2R,5S)-2-[(R)-{[tert-butyl(dimethyl)silyl]oxy}(phenyl)methyl]-5-(4-{[1-(pyridine-2-yl)ethyl]carbamoyl}benzyl)pyrrolidine-1-carboxylate

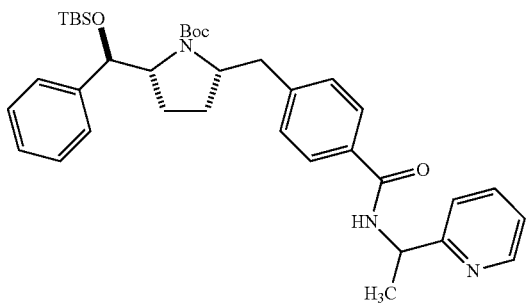

1-Pyridin-2-yl-ethylamine (77 mg, 0.628 mmol) was added to a stirred, room temperature mixture of 4-({(2S,5R)-1-(tert-butoxycarbonyl)-5-[(R)-{[tert-butyl(dimethyl)silyl]oxy}(phenyl)methyl]pyrrolidin-2-yl}methyl)benzoic acid (300 mg, 0.571 mmol), HATU (260 mg, 0.685 mmol, 1.2 equivalents) and DIPEA (470 µL, 2.69 mmol, 4.7 equivalents) in DMF (1.2 mL). The reaction was stirred at room temperature for 16 hours before being loaded directly onto a silica column and purified by normal phase flash chromatography using silica gel (20-100% hexanes/ethyl acetate). The product fractions were collected and concentrated in vacuo to afford the title compound as a colorless gum (350 mg, 97%). LC-MS=630.3 (M+H)+.

Step B: Tert-butyl (2R,5S)-2-[(R)-{[tert-butyl(dimethyl)silyl]oxy}(phenyl)methyl]-5-(4-(methyl[1-(pyridine-2-yl)ethyl]carbamoyl}benzyl)pyrrolidine-1-carboxylate

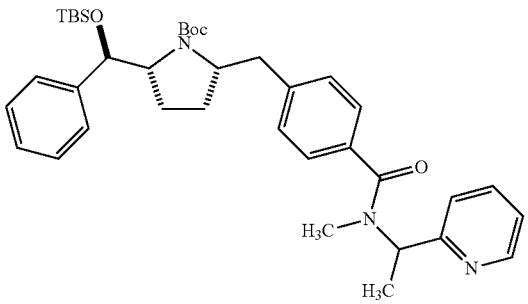

To tert-butyl (2R,5S)-2-[(R)-{[tert-butyl(dimethyl)silyl]oxy}(phenyl)methyl]-5-(4-{[1-(pyridine-2-yl)ethyl] carbamoyl}benzyl)pyrrolidine-1-carboxylate (350 mg, 0.556 mmol) in tetrahydrofuran (1.1 mL), was added sodium hydride (26.7 mg of a 60 wt % dispersion, 0.667 mmol) at 0° C. The reaction was stirred for 30 minutes before methyl iodide (38.2 µl, 0.611 mmol) was added. The resulting red colored reaction was stirred for 3 hours before being quenched by pouring into a separatory funnel containing water and was extracted with ethyl acetate (3×50 mL). The organic extracts were combined and dried with $Na_2SO_4$, filtered, and evapourated in vacuo and taken directly to the next step. LC-MS=644.3 (M+1)+.

Step C: 4-({(2S,5R)-5-[(R)-hydroxy(phenyl)methyl] pyrrolidine-2-yl}methyl)-N-methyl-N-[1-pyridin-2-yl)ethyl]benzamide

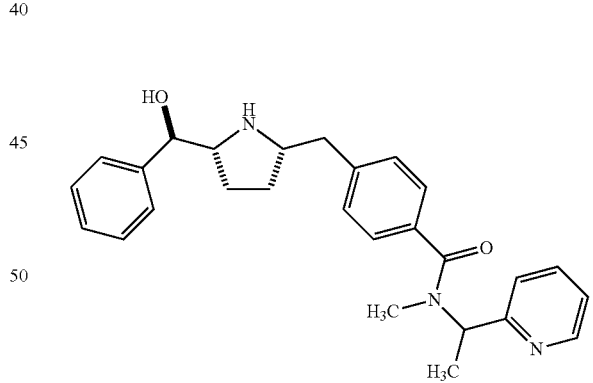

The crude tert-butyl (2R,5S)-2-[(R)-{[tert-butyl(dimethyl) silyl]oxy}(phenyl)methyl]-5-(4-(methyl[1-(pyridine-2-yl) ethyl]carbamoyl}benzyl)pyrrolidine-1-carboxylate was dissolved in a 3:3:1 mixture of acetonitrile (2.0 mL):TFA (2.1 mL):water (0.67 mL), and the mixture was stirred at room temperature for 16 hours. The mixture was then concentrated in vacuo and purified by reverse phase Gilson HPLC using acetonitrile/water with 0.1% TFA buffer. Lyophilization of the desired fractions gave the title compound as the TFA salt (242 mg, 80% yield over two steps) and as a white solid. LC-MS=430.0 (M+1)+.

Using the Beta-3 agonist in vitro functional assay described above the human Beta-3 agonist functional activity of Example 137 was determined to be between 100 to 999 nM.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I, or an N-oxide thereof, or a pharmaceutically acceptable salt thereof, or a stereoisomer thereof, or a pharmaceutically acceptable salt of the stereoisomer thereof:

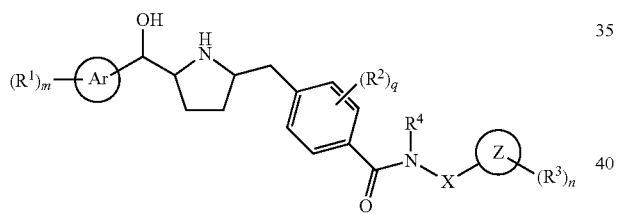

(I)

wherein:
m is 0, 1, 2, 3, 4, or 5;
n is 0, 1, 2, 3, 4, or 5;
p is 0, 1, or 2;
q is 0, 1, 2, 3, or 4;
Ar is phenyl or pyridyl;
X is selected from the group consisting of:
 (1) a bond, and
 (2) $C_1$-$C_6$ alkanediyl optionally substituted with 1 to 5 groups independently selected from:
  (a) halogen,
  (b) —$OR^a$,
  (c) —$CO_2R^a$,
  (d) —$NR^aR^b$, and
  (e) $C_3$-$C_6$ cycloalkyl;
Z is selected from the group consisting of:
 (1) $C_5$-$C_{10}$ carbocyclic ring,
 (2) 4 to 6-membered heterocyclic ring with from 1 to 4 heteroatoms selected from oxygen, sulfur and nitrogen,
 (3) benzene ring fused to a $C_5$-$C_{10}$ carbocyclic ring,
 (4) 5 or 6-membered heterocyclic ring with from 1 to 4 heteroatoms selected from oxygen, sulfur and nitrogen fused to a $C_5$-$C_{10}$ carbocyclic ring, and
 (5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;
each occurrence of $R^1$ is independently selected from the group consisting of:
 (1) $C_1$-$C_6$ alkyl optionally substituted with 1 to 5 halogen atoms,
 (2) $C_3$-$C_6$ cycloalkyl,
 (3) oxo,
 (4) halogen,
 (5) nitro,
 (6) cyano,
 (7) —$C(O)R^a$,
 (8) —$CO_2R^a$,
 (9) —$C(O)NR^aR^b$,
 (10) —$OR^a$,
 (11) —$NR^aR^b$, and
 (12) Z optionally substituted with 1 to 5 halogen atoms;
each occurrence of $R^2$ is independently selected from the group consisting of:
 (1) halogen,
 (2) —$OR^a$, and
 (3) $C_1$-$C_6$ alkyl optionally substituted with 1 to 5 halogen atoms;
each occurrence of $R^3$ is independently selected from the group consisting of:
 (1) $C_1$-$C_6$ alkyl optionally substituted with 1 to 5 groups independently selected from halogen and —$OR^a$,
 (2) $C_3$-$C_6$ cycloalkyl, optionally substituted with 1 to 5 halogen atoms,
 (3) oxo,
 (4) halogen,
 (5) cyano,
 (6) —$OR^a$,
 (7) —$C(O)R^a$,
 (8) —$CO_2R^a$,
 (9) —$C(O)NR^aR^b$,
 (10) —$NR^aR^b$,
 (11) —$C(O)NR^aR^b$, and
 (12) Z optionally substituted with 1 to 5 groups independently selected from
  (a) C1-C6 alkyl optionally substituted with 1 to 5 groups independently selected from halogen, —$OR^a$, oxo, cyano, $CO_2R^a$, and $C_3$-$C_6$ cycloalkyl,
  (b) $C_3$-$C_6$ cycloalkyl,
  (c) halogen,
  (d) oxo,
  (e) —$OR^a$,
  (f) —$NR^aR^b$,
  (g) —$C(O)NR^aR^b$, and
  (h) phenyl;
$R^4$ is selected from the group consisting of:
 (1) hydrogen, and
 (2) $C_1$-$C_6$ alkyl optionally substituted with 1 to 5 groups independently selected from:
  (a) halogen,
  (b) —$OR^a$,
  (c) cyano,
  (d) $C_3$-$C_6$ cycloalkyl,
  (e) Z optionally substituted with 1 to 5 groups independently selected from halogen, $C_1$-$C_6$ alkyl optionally substituted with 1 to 5 halogen atoms, —$OR^a$, oxo, cyano, $CO_2R^a$, and $C_3$-$C_6$ cycloalkyl,
  (g) —$S(O)_p$—$NR^aR^b$, and
  (h) —$N(R^a)SO_2R^b$;

each occurrence of $R^a$ is independently selected from the group consisting of:
(1) hydrogen,
(2) $C_1$-$C_6$ alkyl optionally substituted with 1 to 5 groups independently selected from:
  (a) halogen,
  (b) —$OR^b$, and
  (c) —$CO_2R^b$,
(3) $C_3$-$C_6$ cycloalkyl,
(4) Z optionally substituted with 1 to 5 halogen atoms; and each occurrence of $R^b$ is independently selected from the group consisting of:
(1) hydrogen, and
(2) $C_1$-$C_6$ alkyl optionally substituted with 1 to 5 halogen atoms.

2. The compound of claim 1, wherein m is 0, q is 0 and $R^4$ is hydrogen or methyl.

3. The compound of claim 1, wherein X is —$CH_2$—, —$CH_2CH_2$—, —$CH(CH_3)$—, or —$CH(CH_3)CH_2$—.

4. The compound of claim 1, wherein Z is selected from the group consisting of:
(1) phenyl,
(2) 4 to 6-membered heterocyclic ring with from 1 to 4 heteroatoms selected from oxygen, sulfur and nitrogen,
(3) benzene ring fused to a $C_5$-$C_{10}$ carbocyclic ring,
(4) benzene ring fused to a 5 or 6-membered heterocyclic ring with from 1 to 4 heteroatoms selected from oxygen, sulfur and nitrogen, and
(5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen.

5. The compound of claim 4 wherein Z is a 5-membered heterocyclic ring having one nitrogen atom and 0 to 3 additional heteroatoms independently selected from N, O and S, or a 6-membered heterocycle having 1, 2 or 3 nitrogen atoms, or 1 nitrogen atom and one oxygen or sulfur atom.

6. The compound of claim 4 wherein Z is a 5- or 6-membered heterocyclic ring with from 1 to 4 heteroatoms selected from oxygen, sulfur and nitrogen fused to a $C_5$-$C_6$ carbocyclic ring, and wherein said heterocyclic ring is a 5-membered heterocycle having one nitrogen ring atom and 0 to 3 additional heteroatoms independently selected from N, O and S, or a 6-membered heterocycle having 1, 2 or 3 ring nitrogen atoms, or 1 ring nitrogen atom and a ring oxygen or sulfur atom.

7. The compound of claim 4 wherein Z is a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen, wherein said fused ring has 2 to 5 heteroatoms, at least one of which is nitrogen.

8. The compound of claim 1, wherein Z is selected from the group consisting of thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,2,5-oxadiazolyl,

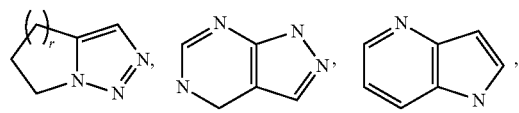

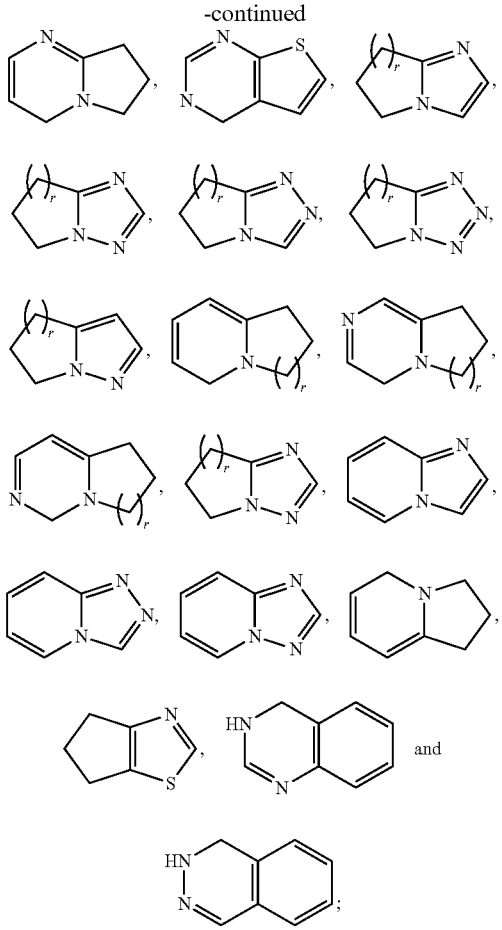

and r is 1 or 2.

9. The compound of claim 1, wherein each occurrence of $R^3$ is independently selected from the group consisting of
(1) $C_1$-$C_6$ alkyl optionally substituted with 1 to 5 halogen atoms,
(2) $C_3$-$C_6$ cycloalkyl, optionally substituted with 1 to 5 halogen atoms,
(3) oxo,
(4) halogen,
(5) —$OR^a$,
(7) —$C(O)R^a$,
(8) —$CO_2R^a$,
(9) —$NR^aR^b$,
(11) —$C(O)NR^aR^b$, and
(12) Z optionally substituted with 1 to 5 groups independently selected from $C_1$-$C_6$ alkyl and halogen.

10. The compound of claim 1, wherein each occurrence of $R^a$ is independently selected from the group consisting of:
(1) hydrogen,
(2) $C_1$-$C_6$ alkyl optionally substituted with 1 to 5 halogen atoms, and
(3) $C_3$-$C_6$ cycloalkyl.

11. A compound of Formula Ia, or an N-oxide thereof, or a pharmaceutically acceptable salt thereof, or a stereoisomer thereof, or a pharmaceutically acceptable salt of the stereoisomer thereof:

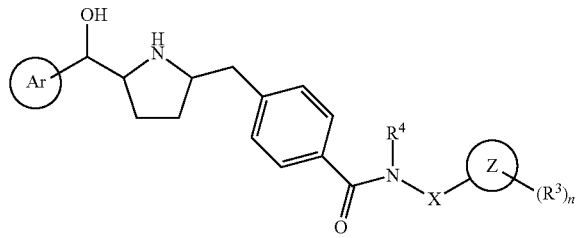

(Ia)

wherein:
n is 0, 1, 2, 3, 4, or 5;
Ar is phenyl or pyridyl;
X is $C_1$-$C_6$ alkanediyl;
Z is selected from the group consisting of:
  (1) phenyl,
  (2) 4 to 6-membered heterocyclic ring with from 1 to 4 heteroatoms selected from oxygen, sulfur and nitrogen,
  (3) benzene ring fused to a $C_5$-$C_{10}$ carbocyclic ring,
  (4) 5 or 6-membered heterocyclic ring with from 1 to 4 heteroatoms selected from oxygen, sulfur and nitrogen fused to a $C_5$-$C_{10}$ carbocyclic ring or a benzene ring, and
  (5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;
each occurrence of $R^3$ is independently selected from the group consisting of:
  (1) $C_1$-$C_6$ alkyl optionally substituted with 1 to 5 groups independently selected from halogen and —$OR^a$,
  (2) $C_5$-$C_6$ cycloalkyl, optionally substituted with 1 to 5 halogen atoms,
  (3) oxo,
  (4) halogen,
  (5) —$OR^a$,
  (7) —$C(O)R^a$,
  (8) —$CO_2R^a$,
  (9) —$NR^aR^b$,
  (11) —$C(O)NR^aR^b$, and
  (12) Z optionally substituted with 1 to 5 groups independently selected from $C_1$-$C_6$ alkyl and halogen;
$R^4$ is hydrogen, methyl or ethyl;
$R^a$ is selected from the group consisting of:
  (1) hydrogen,
  (2) $C_1$-$C_6$ alkyl optionally substituted with 1 to 5 halogen atoms, and
  (3) $C_3$-$C_6$ cycloalkyl; and
$R^b$ is selected from the group consisting of:
  (1) hydrogen, and
  (2) $C_1$-$C_6$ alkyl optionally substituted with 1 to 5 halogen atoms.

12. The compound of claim 11, wherein each occurrence of $R^3$ is independently selected from the group consisting of:
  (1) $C_1$-$C_4$ alkyl optionally substituted with 1 to 3 groups independently selected from halogen and —$OR^a$,
  (2) $C_3$-$C_6$ cycloalkyl, optionally substituted with 1 to 3 halogen atoms,
  (3) halogen,
  (4) —$OR^a$,
  (5) —$CO_2R^a$,
  (6) —$NR^aR^b$, and
  (7) Z optionally substituted with 1 to 5 groups independently selected from $C_1$-$C_4$ alkyl and halogen.

13. The compound of claim 1 sleeted from the group consisting of the compounds in Examples 1-137 of the specification.

14. A pharmaceutical composition comprising a compound of claim 1 and a pharmaceutically acceptable carrier.

* * * * *

UNITED STATES PATENT AND TRADEMARK OFFICE
CERTIFICATE OF CORRECTION

PATENT NO.          : 8,604,038 B2
APPLICATION NO.     : 13/392282
DATED               : December 10, 2013
INVENTOR(S)         : Edmondson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 100 days.

Signed and Sealed this
Twenty-second Day of September, 2015

Michelle K. Lee
*Director of the United States Patent and Trademark Office*